US007572619B2

(12) United States Patent
Hauser et al.

(10) Patent No.: US 7,572,619 B2
(45) Date of Patent: Aug. 11, 2009

(54) RECOMBINANT BLOOD CLOTTING FACTORS

(75) Inventors: Charlotte Hauser, Munich (DE); Andrea Hörster, Ebersberg (DE); Carola Schröder, Munich (DE); Michael Lehnerer, Munich (DE)

(73) Assignee: Octagene GmbH, Munich (DE)

( * ) Notice: Subject to any disclaimer, the term of this patent is extended or adjusted under 35 U.S.C. 154(b) by 0 days.

(21) Appl. No.: 10/239,498

(22) PCT Filed: Mar. 21, 2001

(86) PCT No.: PCT/EP01/03220

§ 371 (c)(1),
(2), (4) Date: Jul. 8, 2003

(87) PCT Pub. No.: WO01/70968

PCT Pub. Date: Sep. 27, 2001

(65) Prior Publication Data

US 2004/0023333 A1 Feb. 5, 2004

Related U.S. Application Data

(60) Provisional application No. 60/203,249, filed on May 8, 2000.

(30) Foreign Application Priority Data

Mar. 22, 2000 (EP) .................................. 00106225

(51) Int. Cl.
*C12N 9/64* (2006.01)
*C12N 15/63* (2006.01)
*C07H 21/04* (2006.01)
*C12H 1/20* (2006.01)
*C12P 21/00* (2006.01)
(52) U.S. Cl. .................. 435/226; 536/23.2; 435/320.1; 435/252.3; 435/71.1
(58) Field of Classification Search .................. 435/226
See application file for complete search history.

(56) References Cited

U.S. PATENT DOCUMENTS 5,422,260 A 6/1995 Kaufman et al.
5,445,953 A * 8/1995 Dorner et al. ................ 435/457

FOREIGN PATENT DOCUMENTS

| EP | 0 309 237 A | 3/1989 |
| WO | 86/06408 A | 11/1986 |
| WO | 87/04187 A | 7/1987 |
| WO | WO 91/07490 * | 5/1991 |
| WO | WO 91 11519 A | 8/1991 |
| WO | WO 98 12207 A | 3/1998 |
| WO | WO 00 49147 A | 8/2000 |

OTHER PUBLICATIONS

Galye et al, Identification of regions in interleukin-1 alpha important for activity. J Biol Chem. Oct 15, 1993;268(29):22105-11.*
Whisstock et al, Prediction of protein function from protein sequence and structure. Q Rev Biophys. Aug. 2003;36(3):307-40. Review.*
GenEmbl database Acc. No. l14087 Dorner et al Sep. 26, 1995 from US 5,445,953. Alignment with SEQ ID No. 8.*
NEBcutter USPTO in house restriction site analysis of GenEmbl database Acc. No. l14087 Dorner et al Sep. 26, 1995 from US 5,445,953.*
Herlitschka et al, High expression of a B-domain deleted factor VIII gene in a human hepatic cell line. J Biotechnol. May 13, 1998;61(3):165-73.*
Barrett et al, Trypsin In: Handbook of Proteolytic Enzymes. Academic Press 1998 pp. 168-169.*
Farbiszewski et al, Neutralization of heparin by basic proteins of tumor cells: studies in vitro with protein rich in 14C-arginine. Folia Haematol Int Mag Klin Morphol Blutforsch. 1981;108(3);428-32.*
Byun et al, Low molecular weight protamine: a potential nontoxic heparin antagonist. Thromb Res. Apr. 1, 1999;94(1):53-61.*
Juhasz et al, Mass spectrometric molecular-weight determination of highly acidic compounds of biological significance via their complexes with basic polypeptides. Proc Natl Acad Sci U S A. May 10, 1994;91(10);4333-7.*
Pal et al, Neutralization of heparin by histone and its subfractions. Thromb Res. Jul. 1, 1983;31(1):69-79.*
Graham Fl, et al.; Characteristics of a Human Cell Line Transformed by DNA From Human Adenovirus Type 5, Jul. 1997, 59-74, vol. 36.
Kenny D., et al.; The Critical Interaction of Glycoprotein (GP) Ib-beta with GPIX—A Genetic Cause of Bernard-Soulier Syndrome, Blood, May 1, 1999, 2968-2975, vol. 93 No. 9.
Kenny D., et al.; A Dinucleotide Deletion Results in Defective Membrane Anchoring and Circulating Soluble Glycoprotein Ib-alpha in a Novel Form of Bernard-Soulier Syndrome, Blood, Oct. 1, 1997, 2626-2633, vol. 90 No. 7.
Liu, M., et al.; A Domain Mutations in 65 Haemophilia A Families and Molecular Modeling of Dysfunctional Factor VIII Proteins, British Journal of Haematology, 1998, 1051-1060, vol. 103.
ATCC Catalogue: 293T/17; ATCC No. CRL-11268, 2004, available at www.atcc.org/SearchCatalogs/longview.cfm.

(Continued)

*Primary Examiner*—Sheridan Swope
(74) *Attorney, Agent, or Firm*—Wiley Rein LLP

(57) ABSTRACT

The present invention relates to an improved method for the production of recombinant human blood clotting factors, in particular of factor VIII and factor IX. An immortalized human cell line can be used to stably express viral transcription activator proteins and carrying a vector having a promoter functionally linked to a DNA sequence coding for a blood coagulating factor, provided that said promoter is not a viral promoter which is stimulated by said viral transcription activator proteins. The invention further relates to an immortalized human cell line carrying said vector, factor VIII muteins particularly suitable for the above production method; pharmaceutical compositions comprising such factor VIII muteins, and the use of such factor VIII muteins for preparing a medicament for treating hemophilia.

44 Claims, 10 Drawing Sheets

OTHER PUBLICATIONS

Moens U., et al., "Simian virus 40 large T-antigen, but not small T-antigen, trans-activates the human Cytomegalovirus major immediate early promoter." Virus Genes, vol. 23, No. 2, 2001, pp. 215-226.

Wion, Karen L., et al., "Distribution of factor VIII mRNA and antigen in human liver and other tissues," Nature, vol. 317, Oct. 24, 1985, pp. 726-729.

Wood, William I., et al., "Expression of active human factor VIII from recombinant DNA clones," Nature, vol. 312, Nov. 22, 1984, pp. 330-337.

Deposit—General Cell Collection ECACC No. 9612 1229, tsA201, Accession No. DSM ACC2494, Feb. 20, 2001.

European Search Report for EP 04 00 9279 dated Apr. 1, 2005.

* cited by examiner aga| agc ttc tcc cag aat tca aga cat caa gct tat cga tac cgt cga ggg gaa

R740  S  F  S  Q  N  S  R  H  Q  A  Y  R  Y  R  R  G  E1649 wt-B-domain          variable domain

Fig. 7
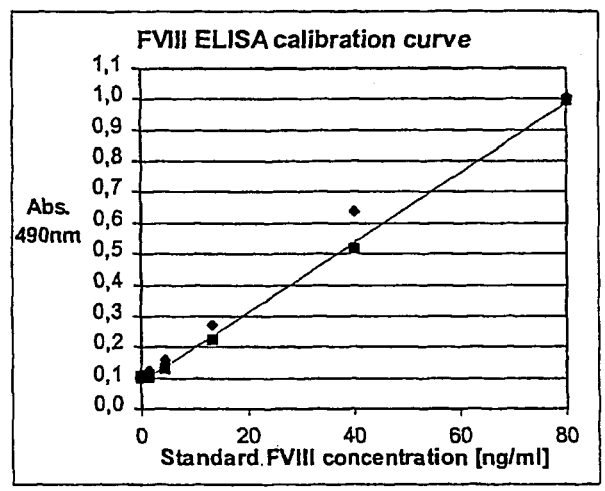
Fig. 7 A
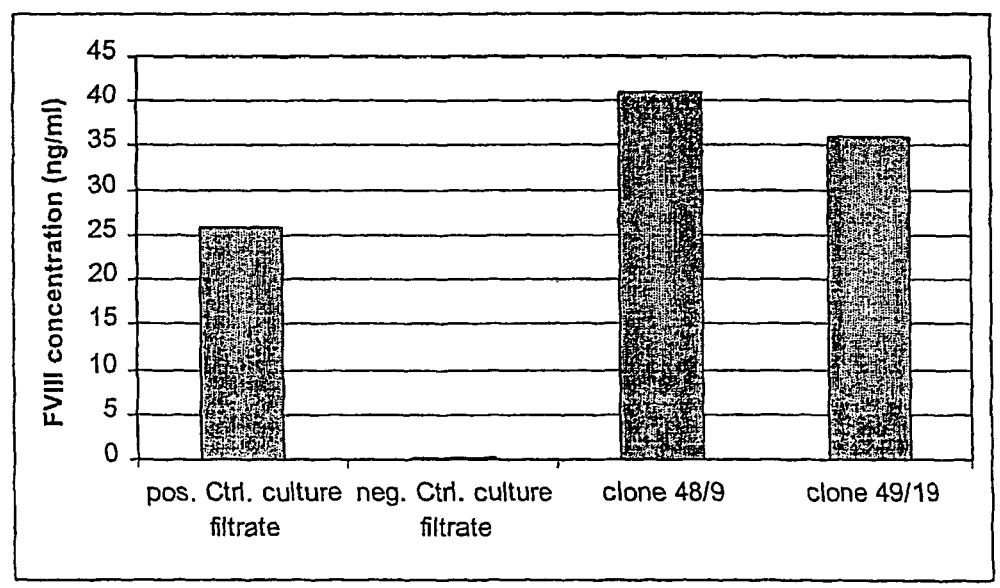
Fig. 7 B

SEQUENCE LISTING

```
<160> NUMBER OF SEQ ID NOS: 17

<210> SEQ ID NO 1
<211> LENGTH: 6996
<212> TYPE: DNA
<213> ORGANISM: Homo sapiens
<220> FEATURE:
<221> NAME/KEY: CDS
<222> LOCATION: (1)..(6996)

<400> SEQUENCE: 1 gcc acc aga aga tac tac ctg ggt gca gtg gaa ctg tca tgg gac tat      48
Ala Thr Arg Arg Tyr Tyr Leu Gly Ala Val Glu Leu Ser Trp Asp Tyr
 1               5                  10                  15 atg caa agt gat ctc ggt gag ctg cct gtg gac gca aga ttt cct cct      96
Met Gln Ser Asp Leu Gly Glu Leu Pro Val Asp Ala Arg Phe Pro Pro
            20                  25                  30 aga gtg cca aaa tct ttt cca ttc aac acc tca gtc gtg tac aaa aag     144
Arg Val Pro Lys Ser Phe Pro Phe Asn Thr Ser Val Val Tyr Lys Lys
        35                  40                  45 act ctg ttt gta gaa ttc acg gtt cac ctt ttc aac atc gct aag cca     192
Thr Leu Phe Val Glu Phe Thr Val His Leu Phe Asn Ile Ala Lys Pro
    50                  55                  60 agg cca ccc tgg atg ggt ctg cta ggt cct acc atc cag gct gag gtt     240
Arg Pro Pro Trp Met Gly Leu Leu Gly Pro Thr Ile Gln Ala Glu Val
65                  70                  75                  80
```

```
tat gat aca gtg gtc att aca ctt aag aac atg gct tcc cat cct gtc    288
Tyr Asp Thr Val Val Ile Thr Leu Lys Asn Met Ala Ser His Pro Val
                85                  90                  95 agt ctt cat gct gtt ggt gta tcc tac tgg aaa gct tct gag gga gct    336
Ser Leu His Ala Val Gly Val Ser Tyr Trp Lys Ala Ser Glu Gly Ala
        100                 105                 110 gaa tat gat gat cag acc agt caa agg gag aaa gaa gat gat aaa gtc    384
Glu Tyr Asp Asp Gln Thr Ser Gln Arg Glu Lys Glu Asp Asp Lys Val
            115                 120                 125 ttc cct ggt gga agc cat aca tat gtc tgg cag gtc ctg aaa gag aat    432
Phe Pro Gly Gly Ser His Thr Tyr Val Trp Gln Val Leu Lys Glu Asn
130                 135                 140 ggt cca atg gcc tct gac cca ctg tgc ctt acc tac tca tat ctt tct    480
Gly Pro Met Ala Ser Asp Pro Leu Cys Leu Thr Tyr Ser Tyr Leu Ser
145                 150                 155                 160 cat gtg gac ctg gta aaa gac ttg aat tca ggc ctc att gga gcc cta    528
His Val Asp Leu Val Lys Asp Leu Asn Ser Gly Leu Ile Gly Ala Leu
                165                 170                 175 cta gta tgt aga gaa ggg agt ctg gcc aag gaa aag aca cag acc ttg    576
Leu Val Cys Arg Glu Gly Ser Leu Ala Lys Glu Lys Thr Gln Thr Leu
            180                 185                 190 cac aaa ttt ata cta ctt ttt gct gta ttt gat gaa ggg aaa agt tgg    624
His Lys Phe Ile Leu Leu Phe Ala Val Phe Asp Glu Gly Lys Ser Trp
        195                 200                 205 cac tca gaa aca aag aac tcc ttg atg cag gat agg gat gct gca tct    672
His Ser Glu Thr Lys Asn Ser Leu Met Gln Asp Arg Asp Ala Ala Ser
210                 215                 220 gct cgg gcc tgg cct aaa atg cac aca gtc aat ggt tat gta aac agg    720
Ala Arg Ala Trp Pro Lys Met His Thr Val Asn Gly Tyr Val Asn Arg
225                 230                 235                 240 tct ctg cca ggt ctg att gga tgc cac agg aaa tca gtc tat tgg cat    768
Ser Leu Pro Gly Leu Ile Gly Cys His Arg Lys Ser Val Tyr Trp His
                245                 250                 255 gtg att gga atg ggc acc act cct gaa gtg cac tca ata ttc ctc gaa    816
Val Ile Gly Met Gly Thr Thr Pro Glu Val His Ser Ile Phe Leu Glu
            260                 265                 270 ggt cac aca ttt ctt gtg agg aac cat cgc cag gcg tcc ttg gaa atc    864
Gly His Thr Phe Leu Val Arg Asn His Arg Gln Ala Ser Leu Glu Ile
        275                 280                 285 tcg cca ata act ttc ctt act gct caa aca ctc ttg atg gac ctt gga    912
Ser Pro Ile Thr Phe Leu Thr Ala Gln Thr Leu Leu Met Asp Leu Gly
290                 295                 300 cag ttt cta ctg ttt tgt cat atc tct tcc cac caa cat gat ggc atg    960
Gln Phe Leu Leu Phe Cys His Ile Ser Ser His Gln His Asp Gly Met
305                 310                 315                 320 gaa gct tat gtc aaa gta gac agc tgt cca gag gaa ccc caa cta cga    1008
Glu Ala Tyr Val Lys Val Asp Ser Cys Pro Glu Glu Pro Gln Leu Arg
                325                 330                 335 atg aaa aat aat gaa gaa gcg gaa gac tat gat gat gat ctt act gat    1056
Met Lys Asn Asn Glu Glu Ala Glu Asp Tyr Asp Asp Asp Leu Thr Asp
            340                 345                 350 tct gaa atg gat gtg gtc agg ttt gat gat gac aac tct cct tcc ttt    1104
Ser Glu Met Asp Val Val Arg Phe Asp Asp Asp Asn Ser Pro Ser Phe
        355                 360                 365 atc caa att cgc tca gtt gcc aag aag cat cct aaa act tgg gta cat    1152
Ile Gln Ile Arg Ser Val Ala Lys Lys His Pro Lys Thr Trp Val His
370                 375                 380 tac att gct gct gaa gag gag gac tgg gac tat gct ccc tta gtc ctc    1200
Tyr Ile Ala Ala Glu Glu Glu Asp Trp Asp Tyr Ala Pro Leu Val Leu
```

-continued

```
                385                 390                 395                 400
gcc ccc gat gac aga agt tat aaa agt caa tat ttg aac aat ggc cct       1248
Ala Pro Asp Asp Arg Ser Tyr Lys Ser Gln Tyr Leu Asn Asn Gly Pro
                    405                 410                 415 cag cgg att ggt agg aag tac aaa aaa gtc cga ttt atg gca tac aca       1296
Gln Arg Ile Gly Arg Lys Tyr Lys Lys Val Arg Phe Met Ala Tyr Thr
                420                 425                 430 gat gaa acc ttt aag act cgt gaa gct att cag cat gaa tca gga atc       1344
Asp Glu Thr Phe Lys Thr Arg Glu Ala Ile Gln His Glu Ser Gly Ile
            435                 440                 445 ttg gga cct tta ctt tat ggg gaa gtt gga gac aca ctg ttg att ata       1392
Leu Gly Pro Leu Leu Tyr Gly Glu Val Gly Asp Thr Leu Leu Ile Ile
        450                 455                 460 ttt aag aat caa gca agc aga cca tat aac atc tac cct cac gga atc       1440
Phe Lys Asn Gln Ala Ser Arg Pro Tyr Asn Ile Tyr Pro His Gly Ile
465                 470                 475                 480 act gat gtc cgt cct ttg tat tca agg aga tta cca aaa ggt gta aaa       1488
Thr Asp Val Arg Pro Leu Tyr Ser Arg Arg Leu Pro Lys Gly Val Lys
                    485                 490                 495 cat ttg aag gat ttt cca att ctg cca gga gaa ata ttc aaa tat aaa       1536
His Leu Lys Asp Phe Pro Ile Leu Pro Gly Glu Ile Phe Lys Tyr Lys
                500                 505                 510 tgg aca gtg act gta gaa gat ggg cca act aaa tca gat cct cgg tgc       1584
Trp Thr Val Thr Val Glu Asp Gly Pro Thr Lys Ser Asp Pro Arg Cys
            515                 520                 525 ctg acc cgc tat tac tct agt ttc gtt aat atg gag aga gat cta gct       1632
Leu Thr Arg Tyr Tyr Ser Ser Phe Val Asn Met Glu Arg Asp Leu Ala
        530                 535                 540 tca gga ctc att ggc cct ctc ctc atc tgc tac aaa gaa tct gta gat       1680
Ser Gly Leu Ile Gly Pro Leu Leu Ile Cys Tyr Lys Glu Ser Val Asp
545                 550                 555                 560 caa aga gga aac cag ata atg tca gac aag agg aat gtc atc ctg ttt       1728
Gln Arg Gly Asn Gln Ile Met Ser Asp Lys Arg Asn Val Ile Leu Phe
                    565                 570                 575 tct gta ttt gat gag aac cga agc tgg tac ctc aca gag aat ata caa       1776
Ser Val Phe Asp Glu Asn Arg Ser Trp Tyr Leu Thr Glu Asn Ile Gln
                580                 585                 590 cgc ttt ctc ccc aat cca gct gga gtg cag ctt gag gat cca gag ttc       1824
Arg Phe Leu Pro Asn Pro Ala Gly Val Gln Leu Glu Asp Pro Glu Phe
            595                 600                 605 caa gcc tcc aac atc atg cac agc atc aat ggc tat gtt ttt gat agt       1872
Gln Ala Ser Asn Ile Met His Ser Ile Asn Gly Tyr Val Phe Asp Ser
        610                 615                 620 ttg cag ttg tca gtt tgt ttg cat gag gtg gca tac tgg tac att cta       1920
Leu Gln Leu Ser Val Cys Leu His Glu Val Ala Tyr Trp Tyr Ile Leu
625                 630                 635                 640 agc att gga gca cag act gac ttc ctt tct gtc ttc ttc tct gga tat       1968
Ser Ile Gly Ala Gln Thr Asp Phe Leu Ser Val Phe Phe Ser Gly Tyr
                    645                 650                 655 acc ttc aaa cac aaa atg gtc tat gaa gac aca ctc acc cta ttc cca       2016
Thr Phe Lys His Lys Met Val Tyr Glu Asp Thr Leu Thr Leu Phe Pro
                660                 665                 670 ttc tca gga gaa act gtc ttc atg tcg atg gaa aac cca ggt cta tgg       2064
Phe Ser Gly Glu Thr Val Phe Met Ser Met Glu Asn Pro Gly Leu Trp
            675                 680                 685 att ctg ggg tgc cac aac tca gac ttt cgg aac aga ggc atg acc gcc       2112
Ile Leu Gly Cys His Asn Ser Asp Phe Arg Asn Arg Gly Met Thr Ala
        690                 695                 700 tta ctg aag gtt tct agt tgt gac aag aac act ggt gat tat tac gag       2160
Leu Leu Lys Val Ser Ser Cys Asp Lys Asn Thr Gly Asp Tyr Tyr Glu
```

```
Leu Leu Lys Val Ser Ser Cys Asp Lys Asn Thr Gly Asp Tyr Tyr Glu
705                 710                 715                 720 gac agt tat gaa gat att tca gca tac ttg ctg agt aaa aac aat gcc        2208
Asp Ser Tyr Glu Asp Ile Ser Ala Tyr Leu Leu Ser Lys Asn Asn Ala
                725                 730                 735 att gaa cca aga agc ttc tcc cag aat tca aga cac cct agc act agg        2256
Ile Glu Pro Arg Ser Phe Ser Gln Asn Ser Arg His Pro Ser Thr Arg
        740                 745                 750 caa aag caa ttt aat gcc acc aca att cca gaa aat gac ata gag aag        2304
Gln Lys Gln Phe Asn Ala Thr Thr Ile Pro Glu Asn Asp Ile Glu Lys
    755                 760                 765 act gac cct tgg ttt gca cac aga aca cct atg cct aaa ata caa aat        2352
Thr Asp Pro Trp Phe Ala His Arg Thr Pro Met Pro Lys Ile Gln Asn
770                 775                 780 gtc tcc tct agt gat ttg ttg atg ctc ttg cga cag agt cct act cca        2400
Val Ser Ser Ser Asp Leu Leu Met Leu Leu Arg Gln Ser Pro Thr Pro
785                 790                 795                 800 cat ggg cta tcc tta tct gat ctc caa gaa gcc aaa tat gag act ttt        2448
His Gly Leu Ser Leu Ser Asp Leu Gln Glu Ala Lys Tyr Glu Thr Phe
                805                 810                 815 tct gat gat cca tca cct gga gca ata gac agt aat aac agc ctg tct        2496
Ser Asp Asp Pro Ser Pro Gly Ala Ile Asp Ser Asn Asn Ser Leu Ser
        820                 825                 830 gaa atg aca cac ttc agg cca cag ctc cat cac agt ggg gac atg gta        2544
Glu Met Thr His Phe Arg Pro Gln Leu His His Ser Gly Asp Met Val
    835                 840                 845 ttt acc cct gag tca ggc ctc caa tta aga tta aat gag aaa ctg ggg        2592
Phe Thr Pro Glu Ser Gly Leu Gln Leu Arg Leu Asn Glu Lys Leu Gly
850                 855                 860 aca act gca gca aca gag ttg aag aaa ctt gat ttc aaa gtt tct agt        2640
Thr Thr Ala Ala Thr Glu Leu Lys Lys Leu Asp Phe Lys Val Ser Ser
865                 870                 875                 880 aca tca aat aat ctg att tca aca att cca tca gac aat ttg gca gca        2688
Thr Ser Asn Asn Leu Ile Ser Thr Ile Pro Ser Asp Asn Leu Ala Ala
                885                 890                 895 ggt act gat aat aca agt tcc tta gga ccc cca agt atg cca gtt cat        2736
Gly Thr Asp Asn Thr Ser Ser Leu Gly Pro Pro Ser Met Pro Val His
        900                 905                 910 tat gat agt caa tta gat acc act cta ttt ggc aaa aag tca tct ccc        2784
Tyr Asp Ser Gln Leu Asp Thr Thr Leu Phe Gly Lys Lys Ser Ser Pro
    915                 920                 925 ctt act gag tct ggt gga cct ctg agc ttg agt gaa gaa aat aat gat        2832
Leu Thr Glu Ser Gly Gly Pro Leu Ser Leu Ser Glu Glu Asn Asn Asp
930                 935                 940 tca aag ttg tta gaa tca ggt tta atg aat agc caa gaa agt tca tgg        2880
Ser Lys Leu Leu Glu Ser Gly Leu Met Asn Ser Gln Glu Ser Ser Trp
945                 950                 955                 960 gga aaa aat gta tcg tca aca gag agt ggt agg tta ttt aaa ggg aaa        2928
Gly Lys Asn Val Ser Ser Thr Glu Ser Gly Arg Leu Phe Lys Gly Lys
                965                 970                 975 aga gct cat gga cct gct ttg ttg act aaa gat aat gcc tta ttc aaa        2976
Arg Ala His Gly Pro Ala Leu Leu Thr Lys Asp Asn Ala Leu Phe Lys
        980                 985                 990 gtt agc atc tct ttg tta aag aca aac aaa act tcc aat aat tca gca        3024
Val Ser Ile Ser Leu Leu Lys Thr Asn Lys Thr Ser Asn Asn Ser Ala
    995                 1000                1005 act aat aga aag act cac att gat ggc cca tca tta tta att gag aat        3072
Thr Asn Arg Lys Thr His Ile Asp Gly Pro Ser Leu Leu Ile Glu Asn
    1010                1015                1020
```

```
agt cca tca gtc tgg caa aat ata tta gaa agt gac act gag ttt aaa        3120
Ser Pro Ser Val Trp Gln Asn Ile Leu Glu Ser Asp Thr Glu Phe Lys
1025                1030                1035                1040 aaa gtg aca cct ttg att cat gac aga atg ctt atg gac aaa aat gct        3168
Lys Val Thr Pro Leu Ile His Asp Arg Met Leu Met Asp Lys Asn Ala
                1045                1050                1055 aca gct ttg agg cta aat cat atg tca aat aaa act act tca tca aaa        3216
Thr Ala Leu Arg Leu Asn His Met Ser Asn Lys Thr Thr Ser Ser Lys
    1060                1065                1070 aac atg gaa atg gtc caa cag aaa aaa gag ggc ccc att cca cca gat        3264
Asn Met Glu Met Val Gln Gln Lys Lys Glu Gly Pro Ile Pro Pro Asp
        1075                1080                1085 gca caa aat cca gat atg tcg ttc ttt aag atg cta ttc ttg cca gaa        3312
Ala Gln Asn Pro Asp Met Ser Phe Phe Lys Met Leu Phe Leu Pro Glu
1090                1095                1100 tca gca agg tgg ata caa agg act cat gga aag aac tct ctg aac tct        3360
Ser Ala Arg Trp Ile Gln Arg Thr His Gly Lys Asn Ser Leu Asn Ser
1105                1110                1115                1120 ggg caa ggc ccc agt cca aag caa tta gta tcc tta gga cca gaa aaa        3408
Gly Gln Gly Pro Ser Pro Lys Gln Leu Val Ser Leu Gly Pro Glu Lys
                1125                1130                1135 tct gtg gaa ggt cag aat ttc ttg tct gag aaa aac aaa gtg gta gta        3456
Ser Val Glu Gly Gln Asn Phe Leu Ser Glu Lys Asn Lys Val Val Val
            1140                1145                1150 gga aag ggt gaa ttt aca aag gac gta gga ctc aaa gag atg gtt ttt        3504
Gly Lys Gly Glu Phe Thr Lys Asp Val Gly Leu Lys Glu Met Val Phe
        1155                1160                1165 cca agc agc aga aac cta ttt ctt act aac ttg gat aat tta cat gaa        3552
Pro Ser Ser Arg Asn Leu Phe Leu Thr Asn Leu Asp Asn Leu His Glu
    1170                1175                1180 aat aat aca cac aat caa gaa aaa aaa att cag gaa gaa ata gaa aag        3600
Asn Asn Thr His Asn Gln Glu Lys Lys Ile Gln Glu Glu Ile Glu Lys
1185                1190                1195                1200 aag gaa aca tta atc caa gag aat gta gtt ttg cct cag ata cat aca        3648
Lys Glu Thr Leu Ile Gln Glu Asn Val Val Leu Pro Gln Ile His Thr
                1205                1210                1215 gtg act ggc act aag aat ttc atg aag aac ctt ttc tta ctg agc act        3696
Val Thr Gly Thr Lys Asn Phe Met Lys Asn Leu Phe Leu Leu Ser Thr
            1220                1225                1230 agg caa aat gta gaa ggt tca tat gag ggg gca tat gct cca gta ctt        3744
Arg Gln Asn Val Glu Gly Ser Tyr Glu Gly Ala Tyr Ala Pro Val Leu
        1235                1240                1245 caa gat ttt agg tca tta aat gat tca aca aat aga aca aag aaa cac        3792
Gln Asp Phe Arg Ser Leu Asn Asp Ser Thr Asn Arg Thr Lys Lys His
    1250                1255                1260 aca gct cat ttc tca aaa aaa ggg gag gaa gaa aac ttg gaa ggc ttg        3840
Thr Ala His Phe Ser Lys Lys Gly Glu Glu Glu Asn Leu Glu Gly Leu
1265                1270                1275                1280 gga aat caa acc aag caa att gta gag aaa tat gca tgc acc aca agg        3888
Gly Asn Gln Thr Lys Gln Ile Val Glu Lys Tyr Ala Cys Thr Thr Arg
                1285                1290                1295 ata tct cct aat aca agc cag cag aat ttt gtc acg caa cgt agt aag        3936
Ile Ser Pro Asn Thr Ser Gln Gln Asn Phe Val Thr Gln Arg Ser Lys
            1300                1305                1310 aga gct ttg aaa caa ttc aga ctc cca cta gaa gaa aca gaa ctt gaa        3984
Arg Ala Leu Lys Gln Phe Arg Leu Pro Leu Glu Glu Thr Glu Leu Glu
        1315                1320                1325 aaa agg ata att gtg gat gac acc tca acc cag tgg tcc aaa aac atg        4032
Lys Arg Ile Ile Val Asp Asp Thr Ser Thr Gln Trp Ser Lys Asn Met
    1330                1335                1340
```

```
aaa cat ttg acc ccg agc acc ctc aca cag ata gac tac aat gag aag   4080
Lys His Leu Thr Pro Ser Thr Leu Thr Gln Ile Asp Tyr Asn Glu Lys
1345                1350                1355                1360 gag aaa ggg gcc att act cag tct ccc tta tca gat tgc ctt acg agg   4128
Glu Lys Gly Ala Ile Thr Gln Ser Pro Leu Ser Asp Cys Leu Thr Arg
            1365                1370                1375 agt cat agc atc cct caa gca aat aga tct cca tta ccc att gca aag   4176
Ser His Ser Ile Pro Gln Ala Asn Arg Ser Pro Leu Pro Ile Ala Lys
        1380                1385                1390 gta tca tca ttt cca tct att aga cct ata tat ctg acc agg gtc cta   4224
Val Ser Ser Phe Pro Ser Ile Arg Pro Ile Tyr Leu Thr Arg Val Leu
    1395                1400                1405 ttc caa gac aac tct tct cat ctt cca gca gca tct tat aga aag aaa   4272
Phe Gln Asp Asn Ser Ser His Leu Pro Ala Ala Ser Tyr Arg Lys Lys
1410                1415                1420 gat tct ggg gtc caa gaa agc agt cat ttc tta caa gga gcc aaa aaa   4320
Asp Ser Gly Val Gln Glu Ser Ser His Phe Leu Gln Gly Ala Lys Lys
1425                1430                1435                1440 aat aac ctt tct tta gcc att cta acc ttg gag atg act ggt gat caa   4368
Asn Asn Leu Ser Leu Ala Ile Leu Thr Leu Glu Met Thr Gly Asp Gln
            1445                1450                1455 aga gag gtt ggc tcc ctg ggg aca agt gcc aca aat tca gtc aca tac   4416
Arg Glu Val Gly Ser Leu Gly Thr Ser Ala Thr Asn Ser Val Thr Tyr
        1460                1465                1470 aag aaa gtt gag aac act gtt ctc ccg aaa cca gac ttg ccc aaa aca   4464
Lys Lys Val Glu Asn Thr Val Leu Pro Lys Pro Asp Leu Pro Lys Thr
    1475                1480                1485 tct ggc aaa gtt gaa ttg ctt cca aaa gtt cac att tat cag aag gac   4512
Ser Gly Lys Val Glu Leu Leu Pro Lys Val His Ile Tyr Gln Lys Asp
1490                1495                1500 cta ttc cct acg gaa act agc aat ggg tct cct ggc cat ctg gat ctc   4560
Leu Phe Pro Thr Glu Thr Ser Asn Gly Ser Pro Gly His Leu Asp Leu
1505                1510                1515                1520 gtg gaa ggg agc ctt ctt cag gga aca gag gga gcg att aag tgg aat   4608
Val Glu Gly Ser Leu Leu Gln Gly Thr Glu Gly Ala Ile Lys Trp Asn
            1525                1530                1535 gaa gca aac aga cct gga aaa gtt ccc ttt ctg aga gta gca aca gaa   4656
Glu Ala Asn Arg Pro Gly Lys Val Pro Phe Leu Arg Val Ala Thr Glu
        1540                1545                1550 agc tct gca aag act ccc tcc aag cta ttg gat cct ctt gct tgg gat   4704
Ser Ser Ala Lys Thr Pro Ser Lys Leu Leu Asp Pro Leu Ala Trp Asp
    1555                1560                1565 aac cac tat ggt act cag ata cca aaa gaa gag tgg aaa tcc caa gag   4752
Asn His Tyr Gly Thr Gln Ile Pro Lys Glu Glu Trp Lys Ser Gln Glu
1570                1575                1580 aag tca cca gaa aaa aca gct ttt aag aaa aag gat acc att ttg tcc   4800
Lys Ser Pro Glu Lys Thr Ala Phe Lys Lys Lys Asp Thr Ile Leu Ser
1585                1590                1595                1600 ctg aac gct tgt gaa agc aat cat gca ata gca gca ata aat gag gga   4848
Leu Asn Ala Cys Glu Ser Asn His Ala Ile Ala Ala Ile Asn Glu Gly
            1605                1610                1615 caa aat aag ccc gaa ata gaa gtc acc tgg gca aag caa ggt agg act   4896
Gln Asn Lys Pro Glu Ile Glu Val Thr Trp Ala Lys Gln Gly Arg Thr
        1620                1625                1630 gaa agg ctg tgc tct caa aac cca cca gtc ttg aaa cgc cat caa cgg   4944
Glu Arg Leu Cys Ser Gln Asn Pro Pro Val Leu Lys Arg His Gln Arg
    1635                1640                1645 gaa ata act cgt act act ctt cag tca gat caa gag gaa att gac tat   4992
Glu Ile Thr Arg Thr Thr Leu Gln Ser Asp Gln Glu Glu Ile Asp Tyr
```

-continued

```
           1650                  1655                  1660
gat gat acc ata tca gtt gaa atg aag aag gaa gat ttt gac att tat      5040
Asp Asp Thr Ile Ser Val Glu Met Lys Lys Glu Asp Phe Asp Ile Tyr
1665                1670                1675                1680 gat gag gat gaa aat cag agc ccc cgc agc ttt caa aag aaa aca cga      5088
Asp Glu Asp Glu Asn Gln Ser Pro Arg Ser Phe Gln Lys Lys Thr Arg
                1685                1690                1695 cac tat ttt att gct gca gtg gag agg ctc tgg gat tat ggg atg agt      5136
His Tyr Phe Ile Ala Ala Val Glu Arg Leu Trp Asp Tyr Gly Met Ser
    1700                1705                1710 agc tcc cca cat gtt cta aga aac agg gct cag agt ggc agt gtc cct      5184
Ser Ser Pro His Val Leu Arg Asn Arg Ala Gln Ser Gly Ser Val Pro
        1715                1720                1725 cag ttc aag aaa gtt gtt ttc cag gaa ttt act gat ggc tcc ttt act      5232
Gln Phe Lys Lys Val Val Phe Gln Glu Phe Thr Asp Gly Ser Phe Thr
    1730                1735                1740 cag ccc tta tac cgt gga gaa cta aat gaa cat ttg gga ctc ctg ggg      5280
Gln Pro Leu Tyr Arg Gly Glu Leu Asn Glu His Leu Gly Leu Leu Gly
1745                1750                1755                1760 cca tat ata aga gca gaa gtt gaa gat aat atc atg gta act ttc aga      5328
Pro Tyr Ile Arg Ala Glu Val Glu Asp Asn Ile Met Val Thr Phe Arg
                1765                1770                1775 aat cag gcc tct cgt ccc tat tcc ttc tat tct agc ctt att tct tat      5376
Asn Gln Ala Ser Arg Pro Tyr Ser Phe Tyr Ser Ser Leu Ile Ser Tyr
    1780                1785                1790 gag gaa gat cag agg caa gga gca gaa cct aga aaa aac ttt gtc aag      5424
Glu Glu Asp Gln Arg Gln Gly Ala Glu Pro Arg Lys Asn Phe Val Lys
        1795                1800                1805 cct aat gaa acc aaa act tac ttt tgg aaa gtg caa cat cat atg gca      5472
Pro Asn Glu Thr Lys Thr Tyr Phe Trp Lys Val Gln His His Met Ala
    1810                1815                1820 ccc act aaa gat gag ttt gac tgc aaa gcc tgg gct tat ttc tct gat      5520
Pro Thr Lys Asp Glu Phe Asp Cys Lys Ala Trp Ala Tyr Phe Ser Asp
1825                1830                1835                1840 gtt gac ctg gaa aaa gat gtg cac tca ggc ctg att gga ccc ctt ctg      5568
Val Asp Leu Glu Lys Asp Val His Ser Gly Leu Ile Gly Pro Leu Leu
                1845                1850                1855 gtc tgc cac act aac aca ctg aac cct gct cat ggg aga caa gtg aca      5616
Val Cys His Thr Asn Thr Leu Asn Pro Ala His Gly Arg Gln Val Thr
    1860                1865                1870 gta cag gaa ttt gct ctg ttt ttc acc atc ttt gat gag acc aaa agc      5664
Val Gln Glu Phe Ala Leu Phe Phe Thr Ile Phe Asp Glu Thr Lys Ser
        1875                1880                1885 tgg tac ttc act gaa aat atg gaa aga aac tgc agg gct ccc tgc aat      5712
Trp Tyr Phe Thr Glu Asn Met Glu Arg Asn Cys Arg Ala Pro Cys Asn
    1890                1895                1900 atc cag atg gaa gat ccc act ttt aaa gag aat tat cgc ttc cat gca      5760
Ile Gln Met Glu Asp Pro Thr Phe Lys Glu Asn Tyr Arg Phe His Ala
1905                1910                1915                1920 atc aat ggc tac ata atg gat aca cta cct ggc tta gta atg gct cag      5808
Ile Asn Gly Tyr Ile Met Asp Thr Leu Pro Gly Leu Val Met Ala Gln
                1925                1930                1935 gat caa agg att cga tgg tat ctg ctc agc atg ggc agc aat gaa aac      5856
Asp Gln Arg Ile Arg Trp Tyr Leu Leu Ser Met Gly Ser Asn Glu Asn
    1940                1945                1950 atc cat tct att cat ttc agt gga cat gtg ttc act gta cga aaa aaa      5904
Ile His Ser Ile His Phe Ser Gly His Val Phe Thr Val Arg Lys Lys
        1955                1960                1965 gag gag tat aaa atg gca ctg tac aat ctc tat cca ggt gtt ttt gag      5952
```

```
Glu Glu Tyr Lys Met Ala Leu Tyr Asn Leu Tyr Pro Gly Val Phe Glu
    1970                1975                1980 aca gtg gaa atg tta cca tcc aaa gct gga att tgg cgg gtg gaa tgc    6000
Thr Val Glu Met Leu Pro Ser Lys Ala Gly Ile Trp Arg Val Glu Cys
1985                1990                1995                2000 ctt att ggc gag cat cta cat gct ggg atg agc aca ctt ttt ctg gtg    6048
Leu Ile Gly Glu His Leu His Ala Gly Met Ser Thr Leu Phe Leu Val
        2005                2010                2015 tac agc aat aag tgt cag act ccc ctg gga atg gct tct gga cac att    6096
Tyr Ser Asn Lys Cys Gln Thr Pro Leu Gly Met Ala Ser Gly His Ile
            2020                2025                2030 aga gat ttt cag att aca gct tca gga caa tat gga cag tgg gcc cca    6144
Arg Asp Phe Gln Ile Thr Ala Ser Gly Gln Tyr Gly Gln Trp Ala Pro
                2035                2040                2045 aag ctg gcc aga ctt cat tat tcc gga tca atc aat gcc tgg agc acc    6192
Lys Leu Ala Arg Leu His Tyr Ser Gly Ser Ile Asn Ala Trp Ser Thr
2050                2055                2060 aag gag ccc ttt tct tgg atc aag gtg gat ctg ttg gca cca atg att    6240
Lys Glu Pro Phe Ser Trp Ile Lys Val Asp Leu Leu Ala Pro Met Ile
2065                2070                2075                2080 att cac ggc atc aag acc cag ggt gcc cgt cag aag ttc tcc agc ctc    6288
Ile His Gly Ile Lys Thr Gln Gly Ala Arg Gln Lys Phe Ser Ser Leu
            2085                2090                2095 tac atc tct cag ttt atc atc atg tat agt ctt gat ggg aag aag tgg    6336
Tyr Ile Ser Gln Phe Ile Ile Met Tyr Ser Leu Asp Gly Lys Lys Trp
            2100                2105                2110 cag act tat cga gga aat tcc act gga acc tta atg gtc ttc ttt ggc    6384
Gln Thr Tyr Arg Gly Asn Ser Thr Gly Thr Leu Met Val Phe Phe Gly
            2115                2120                2125 aat gtg gat tca tct ggg ata aaa cac aat att ttt aac cct cca att    6432
Asn Val Asp Ser Ser Gly Ile Lys His Asn Ile Phe Asn Pro Pro Ile
        2130                2135                2140 att gct cga tac atc cgt ttg cac cca act cat tat agc att cgc agc    6480
Ile Ala Arg Tyr Ile Arg Leu His Pro Thr His Tyr Ser Ile Arg Ser
2145                2150                2155                2160 act ctt cgc atg gag ttg atg ggc tgt gat tta aat agt tgc agc atg    6528
Thr Leu Arg Met Glu Leu Met Gly Cys Asp Leu Asn Ser Cys Ser Met
            2165                2170                2175 cca ttg gga atg gag agt aaa gca ata tca gat gca cag att act gct    6576
Pro Leu Gly Met Glu Ser Lys Ala Ile Ser Asp Ala Gln Ile Thr Ala
            2180                2185                2190 tca tcc tac ttt acc aat atg ttt gcc acc tgg tct cct tca aaa gct    6624
Ser Ser Tyr Phe Thr Asn Met Phe Ala Thr Trp Ser Pro Ser Lys Ala
        2195                2200                2205 cga ctt cac ctc caa ggg agg agt aat gcc tgg aga cct cag gtg aat    6672
Arg Leu His Leu Gln Gly Arg Ser Asn Ala Trp Arg Pro Gln Val Asn
    2210                2215                2220 aat cca aaa gag tgg ctg caa gtg gac ttc cag aag aca atg aaa gtc    6720
Asn Pro Lys Glu Trp Leu Gln Val Asp Phe Gln Lys Thr Met Lys Val
2225                2230                2235                2240 aca gga gta act act cag gga gta aaa tct ctg ctt acc agc atg tat    6768
Thr Gly Val Thr Thr Gln Gly Val Lys Ser Leu Leu Thr Ser Met Tyr
            2245                2250                2255 gtg aag gag ttc ctc atc tcc agc agt caa gat ggc cat cag tgg act    6816
Val Lys Glu Phe Leu Ile Ser Ser Ser Gln Asp Gly His Gln Trp Thr
            2260                2265                2270 ctc ttt ttt cag aat ggc aaa gta aag gtt ttt cag gga aat caa gac    6864
Leu Phe Phe Gln Asn Gly Lys Val Lys Val Phe Gln Gly Asn Gln Asp
        2275                2280                2285
```

```
tcc ttc aca cct gtg gtg aac tct cta gac cca ccg tta ctg act cgc    6912
Ser Phe Thr Pro Val Val Asn Ser Leu Asp Pro Pro Leu Leu Thr Arg
    2290                2295                2300 tac ctt cga att cac ccc cag agt tgg gtg cac cag att gcc ctg agg    6960
Tyr Leu Arg Ile His Pro Gln Ser Trp Val His Gln Ile Ala Leu Arg
2305                2310                2315                2320 atg gag gtt ctg ggc tgc gag gca cag gac ctc tac                    6996
Met Glu Val Leu Gly Cys Glu Ala Gln Asp Leu Tyr
                2325                2330
```

<210> SEQ ID NO 2
<211> LENGTH: 2332
<212> TYPE: PRT
<213> ORGANISM: Homo sapiens

<400> SEQUENCE: 2

```
Ala Thr Arg Arg Tyr Tyr Leu Gly Ala Val Glu Leu Ser Trp Asp Tyr
 1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320
```

-continued

```
Glu Ala Tyr Val Lys Val Asp Ser Cys Pro Glu Pro Gln Leu Arg
            325                 330                 335
Met Lys Asn Asn Glu Glu Ala Glu Asp Tyr Asp Asp Leu Thr Asp
            340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
    515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
            610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
```

-continued

```
Ile Glu Pro Arg Ser Phe Ser Gln Asn Ser Arg His Pro Ser Thr Arg
            740                 745                 750

Gln Lys Gln Phe Asn Ala Thr Ile Pro Glu Asn Asp Ile Glu Lys
        755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu Asn
    1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
                1045                1050                1055

Thr Ala Leu Arg Leu Asn His Met Ser Asn Lys Thr Thr Ser Ser Lys
            1060                1065                1070

Asn Met Glu Met Val Gln Gln Lys Lys Glu Gly Pro Ile Pro Pro Asp
    1075                1080                1085

Ala Gln Asn Pro Asp Met Ser Phe Phe Lys Met Leu Phe Leu Pro Glu
    1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
                1125                1130                1135

Ser Val Glu Gly Gln Asn Phe Leu Ser Glu Lys Asn Lys Val Val Val
                1140                1145                1150

Gly Lys Gly Glu Phe Thr Lys Asp Val Gly Leu Lys Glu Met Val Phe
```

```
                    1155                1160                1165
Pro Ser Ser Arg Asn Leu Phe Leu Thr Asn Leu Asp Asn Leu His Glu
    1170                1175                1180

Asn Asn Thr His Asn Gln Glu Lys Lys Ile Gln Glu Glu Ile Glu Lys
1185                1190                1195                1200

Lys Glu Thr Leu Ile Gln Glu Asn Val Val Leu Pro Gln Ile His Thr
        1205                1210                1215

Val Thr Gly Thr Lys Asn Phe Met Lys Asn Leu Phe Leu Leu Ser Thr
        1220                1225                1230

Arg Gln Asn Val Glu Gly Ser Tyr Glu Gly Ala Tyr Ala Pro Val Leu
        1235                1240                1245

Gln Asp Phe Arg Ser Leu Asn Asp Ser Thr Asn Arg Thr Lys Lys His
        1250                1255                1260

Thr Ala His Phe Ser Lys Lys Gly Glu Glu Asn Leu Glu Gly Leu
1265                1270                1275                1280

Gly Asn Gln Thr Lys Gln Ile Val Glu Lys Tyr Ala Cys Thr Thr Arg
        1285                1290                1295

Ile Ser Pro Asn Thr Ser Gln Gln Asn Phe Val Thr Gln Arg Ser Lys
        1300                1305                1310

Arg Ala Leu Lys Gln Phe Arg Leu Pro Leu Glu Glu Thr Glu Leu Glu
        1315                1320                1325

Lys Arg Ile Ile Val Asp Asp Thr Ser Thr Gln Trp Ser Lys Asn Met
        1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
        1365                1370                1375

Ser His Ser Ile Pro Gln Ala Asn Arg Ser Pro Leu Pro Ile Ala Lys
        1380                1385                1390

Val Ser Ser Phe Pro Ser Ile Arg Pro Ile Tyr Leu Thr Arg Val Leu
        1395                1400                1405

Phe Gln Asp Asn Ser Ser His Leu Pro Ala Ala Ser Tyr Arg Lys Lys
        1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
            1445                1450                1455

Arg Glu Val Gly Ser Leu Gly Thr Ser Ala Thr Asn Ser Val Thr Tyr
        1460                1465                1470

Lys Lys Val Glu Asn Thr Val Leu Pro Lys Pro Asp Leu Pro Lys Thr
        1475                1480                1485

Ser Gly Lys Val Glu Leu Leu Pro Lys Val His Ile Tyr Gln Lys Asp
        1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
        1525                1530                1535

Glu Ala Asn Arg Pro Gly Lys Val Pro Phe Leu Arg Val Ala Thr Glu
        1540                1545                1550

Ser Ser Ala Lys Thr Pro Ser Lys Leu Leu Asp Pro Leu Ala Trp Asp
        1555                1560                1565

Asn His Tyr Gly Thr Gln Ile Pro Lys Glu Glu Trp Lys Ser Gln Glu
        1570                1575                1580
```

```
Lys Ser Pro Glu Lys Thr Ala Phe Lys Lys Asp Thr Ile Leu Ser
1585                1590                1595                1600

Leu Asn Ala Cys Glu Ser Asn His Ala Ile Ala Ala Ile Asn Glu Gly
                1605                1610                1615

Gln Asn Lys Pro Glu Ile Glu Val Thr Trp Ala Lys Gln Gly Arg Thr
            1620                1625                1630

Glu Arg Leu Cys Ser Gln Asn Pro Pro Val Leu Lys Arg His Gln Arg
        1635                1640                1645

Glu Ile Thr Arg Thr Thr Leu Gln Ser Asp Gln Glu Glu Ile Asp Tyr
    1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
                1685                1690                1695

His Tyr Phe Ile Ala Ala Val Glu Arg Leu Trp Asp Tyr Gly Met Ser
            1700                1705                1710

Ser Ser Pro His Val Leu Arg Asn Arg Ala Gln Ser Gly Ser Val Pro
        1715                1720                1725

Gln Phe Lys Lys Val Val Phe Gln Glu Phe Thr Asp Gly Ser Phe Thr
    1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
                1765                1770                1775

Asn Gln Ala Ser Arg Pro Tyr Ser Phe Tyr Ser Ser Leu Ile Ser Tyr
            1780                1785                1790

Glu Glu Asp Gln Arg Gln Gly Ala Glu Pro Arg Lys Asn Phe Val Lys
        1795                1800                1805

Pro Asn Glu Thr Lys Thr Tyr Phe Trp Lys Val Gln His His Met Ala
    1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
                1845                1850                1855

Val Cys His Thr Asn Thr Leu Asn Pro Ala His Gly Arg Gln Val Thr
            1860                1865                1870

Val Gln Glu Phe Ala Leu Phe Phe Thr Ile Phe Asp Glu Thr Lys Ser
        1875                1880                1885

Trp Tyr Phe Thr Glu Asn Met Glu Arg Asn Cys Arg Ala Pro Cys Asn
    1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
        1955                1960                1965

Glu Glu Tyr Lys Met Ala Leu Tyr Asn Leu Tyr Pro Gly Val Phe Glu
    1970                1975                1980

Thr Val Glu Met Leu Pro Ser Lys Ala Gly Ile Trp Arg Val Glu Cys
1985                1990                1995                2000
```

Leu Ile Gly Glu His Leu His Ala Gly Met Ser Thr Leu Phe Leu Val
            2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
            2035                2040                2045

Lys Leu Ala Arg Leu His Tyr Ser Gly Ser Ile Asn Ala Trp Ser Thr
            2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
            2100                2105                2110

Gln Thr Tyr Arg Gly Asn Ser Thr Gly Thr Leu Met Val Phe Phe Gly
            2115                2120                2125

Asn Val Asp Ser Ser Gly Ile Lys His Asn Ile Phe Asn Pro Pro Ile
            2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
            2165                2170                2175

Pro Leu Gly Met Glu Ser Lys Ala Ile Ser Asp Ala Gln Ile Thr Ala
            2180                2185                2190

Ser Ser Tyr Phe Thr Asn Met Phe Ala Thr Trp Ser Pro Ser Lys Ala
            2195                2200                2205

Arg Leu His Leu Gln Gly Arg Ser Asn Ala Trp Arg Pro Gln Val Asn
            2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
            2245                2250                2255

Val Lys Glu Phe Leu Ile Ser Ser Ser Gln Asp Gly His Gln Trp Thr
            2260                2265                2270

Leu Phe Phe Gln Asn Gly Lys Val Lys Val Phe Gln Gly Asn Gln Asp
            2275                2280                2285

Ser Phe Thr Pro Val Val Asn Ser Leu Asp Pro Pro Leu Leu Thr Arg
            2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
            2325                2330

<210> SEQ ID NO 3
<211> LENGTH: 8720
<212> TYPE: DNA
<213> ORGANISM: Artificial Sequence
<220> FEATURE:
<223> OTHER INFORMATION: Vector pTGF8-1
<220> FEATURE:
<221> NAME/KEY: CDS
<222> LOCATION: (676)..(5052)
<220> FEATURE:
<221> NAME/KEY: mat_peptide
<222> LOCATION: (733)..(5052)

<400> SEQUENCE: 3

-continued

```
cgcgttgaca ttgattattg actagttatt aatagtaatc aattacgggg tcattagttc    60
atagcccata tatggagttc cgcgttacat aacttacggt aaatggcccg cctggctgac   120
cgcccaacga cccccgccca ttgacgtcaa taatgacgta tgttcccata gtaacgccaa   180
tagggacttt ccattgacgt caatgggtgg agtatttacg gtaaactgcc cacttggcag   240
tacatcaagt gtatcatatg ccaagtacgc ccctattga cgtcaatgac ggtaaatggc   300
ccgcctggca ttatgcccag tacatgacct tatgggactt tcctacttgg cagtacatct   360
acgtattagt catcgctatt accatggtga tgcggttttg gcagtacatc aatgggcgtg   420
gatagcggtt tgactcacgg ggatttccaa gtctccaccc cattgacgtc aatgggagtt   480
tgttttggca ccaaaatcaa cgggactttc caaaatgtcg taacaactcc gccccattga   540
cgcaaatggg cggtaggcgt gtacggtggg aggtctatat aagcagagct ctctggctaa   600
ctagagaacc cactgcttac tggcttatcg aaattaatac gactcactat agggagaccc   660
aagcttgacc tcgag atg caa ata gag ctc tcc acc tgc ttc ttt ctg tgc   711
              Met Gln Ile Glu Leu Ser Thr Cys Phe Phe Leu Cys
                              -15                  -10
```

```
ctt ttg cga ttc tgc ttt agt gcc acc aga aga tac tac ctg ggt gca   759
Leu Leu Arg Phe Cys Phe Ser Ala Thr Arg Arg Tyr Tyr Leu Gly Ala
        -5              -1   1                   5
```

```
gtg gaa ctg tca tgg gac tat atg caa agt gat ctc ggt gag ctg cct   807
Val Glu Leu Ser Trp Asp Tyr Met Gln Ser Asp Leu Gly Glu Leu Pro
 10              15                  20                  25
```

```
gtg gac gca aga ttt cct cct aga gtg cca aaa tct ttt cca ttc aac   855
Val Asp Ala Arg Phe Pro Pro Arg Val Pro Lys Ser Phe Pro Phe Asn
             30                  35                  40
```

```
acc tca gtc gtg tac aaa aag act ctg ttt gta gaa ttc acg gat cac   903
Thr Ser Val Val Tyr Lys Lys Thr Leu Phe Val Glu Phe Thr Asp His
                 45                  50                  55
```

```
ctt ttc aac atc gct aag cca agg cca ccc tgg atg ggt ctg cta ggt   951
Leu Phe Asn Ile Ala Lys Pro Arg Pro Pro Trp Met Gly Leu Leu Gly
             60                  65                  70
```

```
cct acc atc cag gct gag gtt tat gat aca gtg gtc att aca ctt aag   999
Pro Thr Ile Gln Ala Glu Val Tyr Asp Thr Val Val Ile Thr Leu Lys
     75                  80                  85
```

```
aac atg gct tcc cat cct gtc agt ctt cat gct gtt ggt gta tcc tac  1047
Asn Met Ala Ser His Pro Val Ser Leu His Ala Val Gly Val Ser Tyr
 90                  95                 100                 105
```

```
tgg aaa gct tct gag gga gct gaa tat gat gat cag acc agt caa agg  1095
Trp Lys Ala Ser Glu Gly Ala Glu Tyr Asp Asp Gln Thr Ser Gln Arg
                110                 115                 120
```

```
gag aaa gaa gat gat aaa gtc ttc cct ggt gga agc cat aca tat gtc  1143
Glu Lys Glu Asp Asp Lys Val Phe Pro Gly Gly Ser His Thr Tyr Val
            125                 130                 135
```

```
tgg cag gtc ctg aaa gag aat ggt cca atg gcc tct gac cca ctg tgc  1191
Trp Gln Val Leu Lys Glu Asn Gly Pro Met Ala Ser Asp Pro Leu Cys
        140                 145                 150
```

```
ctt acc tac tca tat ctt tct cat gcg gac ctg gta aaa gac ttg aat  1239
Leu Thr Tyr Ser Tyr Leu Ser His Ala Asp Leu Val Lys Asp Leu Asn
    155                 160                 165
```

```
tca ggc ctc att gga gcc cta cta gta tgt aga gaa ggg agt ctg gcc  1287
Ser Gly Leu Ile Gly Ala Leu Leu Val Cys Arg Glu Gly Ser Leu Ala
170                 175                 180                 185
```

```
aag gaa aag aca cag acc ttg cac aaa ttt ata cta ctt ttt gct gta  1335
Lys Glu Lys Thr Gln Thr Leu His Lys Phe Ile Leu Leu Phe Ala Val
                190                 195                 200
```

```
ttt gat gaa ggg aaa agt tgg cac tca gaa aca aag aac tcc ttg atg  1383
```

```
                Phe Asp Glu Gly Lys Ser Trp His Ser Glu Thr Lys Asn Ser Leu Met
                            205                 210                 215 cag gat agg gat gct gca tct gct cgg gcc tgg cct aaa atg cac aca          1431
Gln Asp Arg Asp Ala Ala Ser Ala Arg Ala Trp Pro Lys Met His Thr
            220                 225                 230 gtc aat ggt tat gta aac agg tct ctg cca ggt ctg att gga tgc cac          1479
Val Asn Gly Tyr Val Asn Arg Ser Leu Pro Gly Leu Ile Gly Cys His
            235                 240                 245 agg aaa tca gtc tat tgg cat gtg att gga atg ggc acc act cct gaa          1527
Arg Lys Ser Val Tyr Trp His Val Ile Gly Met Gly Thr Thr Pro Glu
250                 255                 260                 265 gtg cac tca ata ttc ctc gaa ggt cac aca ttt ctt gtg agg aac cat          1575
Val His Ser Ile Phe Leu Glu Gly His Thr Phe Leu Val Arg Asn His
                270                 275                 280 cgc cag gcg tcc ttg gaa atc tcg cca ata act ttc ctt act gct caa          1623
Arg Gln Ala Ser Leu Glu Ile Ser Pro Ile Thr Phe Leu Thr Ala Gln
            285                 290                 295 aca ctc ttg atg gac ctt gga cag ttt cta ctg ttt tgt cat atc tct          1671
Thr Leu Leu Met Asp Leu Gly Gln Phe Leu Leu Phe Cys His Ile Ser
            300                 305                 310 tcc cac caa cat gat ggc atg gaa gct tat gtc aaa gta gac agc tgt          1719
Ser His Gln His Asp Gly Met Glu Ala Tyr Val Lys Val Asp Ser Cys
315                 320                 325 cca gag gaa ccc caa cta cga atg aaa aat aat gaa gaa gcg gaa gac          1767
Pro Glu Glu Pro Gln Leu Arg Met Lys Asn Asn Glu Glu Ala Glu Asp
330                 335                 340                 345 tat gat gat gat ctt act gat tct gaa atg gat gtg gtc agg ttt gat          1815
Tyr Asp Asp Asp Leu Thr Asp Ser Glu Met Asp Val Val Arg Phe Asp
                350                 355                 360 gat gac aac tct cct tcc ttt atc caa att cgc tca gtt gcc aag aag          1863
Asp Asp Asn Ser Pro Ser Phe Ile Gln Ile Arg Ser Val Ala Lys Lys
            365                 370                 375 cat cct aaa act tgg gta cat tac att gct gct gaa gag gag gac tgg          1911
His Pro Lys Thr Trp Val His Tyr Ile Ala Ala Glu Glu Glu Asp Trp
            380                 385                 390 gac tat gct ccc tta gtc ctc gcc ccc gat gac aga agt tat aaa agt          1959
Asp Tyr Ala Pro Leu Val Leu Ala Pro Asp Asp Arg Ser Tyr Lys Ser
395                 400                 405 caa tat ttg aac aat ggc cct cag cgg att ggt agg aag tac aaa aaa          2007
Gln Tyr Leu Asn Asn Gly Pro Gln Arg Ile Gly Arg Lys Tyr Lys Lys
410                 415                 420                 425 gtc cga ttt atg gca tac aca gat gaa acc ttt aag act cgt gaa gct          2055
Val Arg Phe Met Ala Tyr Thr Asp Glu Thr Phe Lys Thr Arg Glu Ala
                430                 435                 440 att cag cat gaa tca gga atc ttg gga cct tta ctt tat ggg gaa gtt          2103
Ile Gln His Glu Ser Gly Ile Leu Gly Pro Leu Leu Tyr Gly Glu Val
            445                 450                 455 gga gac aca ctg ttg att ata ttt aag aat caa gca agc aga cca tat          2151
Gly Asp Thr Leu Leu Ile Ile Phe Lys Asn Gln Ala Ser Arg Pro Tyr
            460                 465                 470 aac atc tac cct cac gga atc act gat gtc cgt cct ttg tat tca agg          2199
Asn Ile Tyr Pro His Gly Ile Thr Asp Val Arg Pro Leu Tyr Ser Arg
475                 480                 485 aga tta cca aaa ggt gta aaa cat ttg aag gat ttt cca att ctg cca          2247
Arg Leu Pro Lys Gly Val Lys His Leu Lys Asp Phe Pro Ile Leu Pro
490                 495                 500                 505 gga gaa ata ttc aaa tat aaa tgg aca gtg act gta gaa gat ggg cca          2295
Gly Glu Ile Phe Lys Tyr Lys Trp Thr Val Thr Val Glu Asp Gly Pro
                510                 515                 520
```

```
act aaa tca gat cct cgg tgc ctg acc cgc tat tac tct agt ttc gtt    2343
Thr Lys Ser Asp Pro Arg Cys Leu Thr Arg Tyr Tyr Ser Ser Phe Val
        525                 530                 535 aat atg gag aga gat cta gct tca gga ctc att ggc cct ctc ctc atc    2391
Asn Met Glu Arg Asp Leu Ala Ser Gly Leu Ile Gly Pro Leu Leu Ile
540                 545                 550 tgc tac aaa gaa tct gta gat caa aga gga aac cag ata atg tca gac    2439
Cys Tyr Lys Glu Ser Val Asp Gln Arg Gly Asn Gln Ile Met Ser Asp
            555                 560                 565 aag agg aat gtc atc ctg ttt tct gta ttt gat gag aac cga agc tgg    2487
Lys Arg Asn Val Ile Leu Phe Ser Val Phe Asp Glu Asn Arg Ser Trp
570                 575                 580                 585 tac ctc aca gag aat ata caa cgc ttt ctc ccc aat cca gct gga gtg    2535
Tyr Leu Thr Glu Asn Ile Gln Arg Phe Leu Pro Asn Pro Ala Gly Val
                590                 595                 600 cag ctt gag gat cca gag ttc caa gcc tcc aac atc atg cac agc atc    2583
Gln Leu Glu Asp Pro Glu Phe Gln Ala Ser Asn Ile Met His Ser Ile
        605                 610                 615 aat ggc tat gtt ttt gat agt ttg cag ttg tca gtt tgt ttg cat gag    2631
Asn Gly Tyr Val Phe Asp Ser Leu Gln Leu Ser Val Cys Leu His Glu
620                 625                 630 gtg gca tac tgg tac att cta agc att gga gca cag act gac ttc ctt    2679
Val Ala Tyr Trp Tyr Ile Leu Ser Ile Gly Ala Gln Thr Asp Phe Leu
            635                 640                 645 tct gtc ttc ttc tct gga tat acc ttc aaa cac aaa atg gtc tat gaa    2727
Ser Val Phe Phe Ser Gly Tyr Thr Phe Lys His Lys Met Val Tyr Glu
650                 655                 660                 665 gac aca ctc acc cta ttc cca ttc tca gga gaa act gtc ttc atg tcg    2775
Asp Thr Leu Thr Leu Phe Pro Phe Ser Gly Glu Thr Val Phe Met Ser
                670                 675                 680 atg gaa aac cca ggt cta tgg att ctg ggg tgc cac aac tca gac ttt    2823
Met Glu Asn Pro Gly Leu Trp Ile Leu Gly Cys His Asn Ser Asp Phe
        685                 690                 695 cgg aac aga ggc atg acc gcc tta ctg aag gtt tct agt tgt gac aag    2871
Arg Asn Arg Gly Met Thr Ala Leu Leu Lys Val Ser Ser Cys Asp Lys
700                 705                 710 aac act ggt gat tat tac gag gac agt tat gaa gat att tca gca tac    2919
Asn Thr Gly Asp Tyr Tyr Glu Asp Ser Tyr Glu Asp Ile Ser Ala Tyr
            715                 720                 725 ttg ctg agt aaa aac aat gcc att gaa cca aga agc ttc tcc cag aat    2967
Leu Leu Ser Lys Asn Asn Ala Ile Glu Pro Arg Ser Phe Ser Gln Asn
730                 735                 740                 745 tca aga cat caa gct tat cga tac cgt cga ggg gaa ata act cgt act    3015
Ser Arg His Gln Ala Tyr Arg Tyr Arg Arg Gly Glu Ile Thr Arg Thr
                750                 755                 760 act ctt cag tca gat caa gag gaa att gac tat gat gat acc ata tca    3063
Thr Leu Gln Ser Asp Gln Glu Glu Ile Asp Tyr Asp Asp Thr Ile Ser
        765                 770                 775 gtt gaa atg aag aag gaa gat ttt gac att tat gat gag gat gaa aat    3111
Val Glu Met Lys Lys Glu Asp Phe Asp Ile Tyr Asp Glu Asp Glu Asn
780                 785                 790 cag agc ccc cgc agc ttt caa aag aaa aca cga cac tat ttt att gct    3159
Gln Ser Pro Arg Ser Phe Gln Lys Lys Thr Arg His Tyr Phe Ile Ala
            795                 800                 805 gca gtg gag agg ctc tgg gat tat ggg atg agt agc tcc cca cat gtt    3207
Ala Val Glu Arg Leu Trp Asp Tyr Gly Met Ser Ser Ser Pro His Val
810                 815                 820                 825 cta aga aac agg gct cag agt ggc agt gtc cct cag ttc aag aaa gtt    3255
Leu Arg Asn Arg Ala Gln Ser Gly Ser Val Pro Gln Phe Lys Lys Val
                830                 835                 840
```

```
gtt ttc cag gaa ttt act gat ggc tcc ttt act cag ccc tta tac cgt       3303
Val Phe Gln Glu Phe Thr Asp Gly Ser Phe Thr Gln Pro Leu Tyr Arg
                845                 850                 855 gga gaa cta aat gaa cat ttg gga ctc ctg ggg cca tat ata aga gca       3351
Gly Glu Leu Asn Glu His Leu Gly Leu Leu Gly Pro Tyr Ile Arg Ala
            860                 865                 870 gaa gtt gaa gat aat atc atg gta act ttc aga aat cag gcc tct cgt       3399
Glu Val Glu Asp Asn Ile Met Val Thr Phe Arg Asn Gln Ala Ser Arg
875                 880                 885 ccc tat tcc ttc tat tct agc ctt att tct tat gag gaa gat cag agg       3447
Pro Tyr Ser Phe Tyr Ser Ser Leu Ile Ser Tyr Glu Glu Asp Gln Arg
890                 895                 900                 905 caa gga gca gaa cct aga aaa aac ttt gtc aag cct aat gaa acc aaa       3495
Gln Gly Ala Glu Pro Arg Lys Asn Phe Val Lys Pro Asn Glu Thr Lys
            910                 915                 920 act tac ttt tgg aaa gtg caa cat cat atg gca ccc act aaa gat gag       3543
Thr Tyr Phe Trp Lys Val Gln His His Met Ala Pro Thr Lys Asp Glu
                925                 930                 935 ttt gac tgc aaa gcc tgg gct tat ttc tct gat gtt gac ctg gaa aaa       3591
Phe Asp Cys Lys Ala Trp Ala Tyr Phe Ser Asp Val Asp Leu Glu Lys
                940                 945                 950 gat gtg cac tca ggc ctg att gga ccc ctt ctg gtc tgc cac act aac       3639
Asp Val His Ser Gly Leu Ile Gly Pro Leu Leu Val Cys His Thr Asn
            955                 960                 965 aca ctg aac cct gct cat ggg aga caa gtg aca gta cag gaa ttt gct       3687
Thr Leu Asn Pro Ala His Gly Arg Gln Val Thr Val Gln Glu Phe Ala
970                 975                 980                 985 ctg ttt ttc acc atc ttt gat gag acc aaa agc tgg tac ttc act gaa       3735
Leu Phe Phe Thr Ile Phe Asp Glu Thr Lys Ser Trp Tyr Phe Thr Glu
                990                 995                 1000 aat atg gaa aga aac tgc agg gct ccc tgc aat atc cag atg gaa gat       3783
Asn Met Glu Arg Asn Cys Arg Ala Pro Cys Asn Ile Gln Met Glu Asp
                1005                1010                1015 ccc act ttt aaa gag aat tat cgc ttc cat gca atc aat ggc tac ata       3831
Pro Thr Phe Lys Glu Asn Tyr Arg Phe His Ala Ile Asn Gly Tyr Ile
                1020                1025                1030 atg gat aca cta cct ggc tta gta atg gct cag gat caa agg att cga       3879
Met Asp Thr Leu Pro Gly Leu Val Met Ala Gln Asp Gln Arg Ile Arg
                1035                1040                1045 tgg tat ctg ctc agc atg ggc agc aat gaa aac atc cat tct att cat       3927
Trp Tyr Leu Leu Ser Met Gly Ser Asn Glu Asn Ile His Ser Ile His
1050                1055                1060                1065 ttc agt gga cat gtg ttc act gta cga aaa aaa gag gag tat aaa atg       3975
Phe Ser Gly His Val Phe Thr Val Arg Lys Lys Glu Glu Tyr Lys Met
                1070                1075                1080 gca ctg tac aat ctc tat cca ggt gtt ttt gag aca gtg gaa atg tta       4023
Ala Leu Tyr Asn Leu Tyr Pro Gly Val Phe Glu Thr Val Glu Met Leu
                1085                1090                1095 cca tcc aaa gct gga att tgg cgg gtg gaa tgc ctt att ggc gag cat       4071
Pro Ser Lys Ala Gly Ile Trp Arg Val Glu Cys Leu Ile Gly Glu His
            1100                1105                1110 cta cat gct ggg atg aac aca ctt ttt ctg gtg tac agc aat aag tgt       4119
Leu His Ala Gly Met Asn Thr Leu Phe Leu Val Tyr Ser Asn Lys Cys
            1115                1120                1125 cag act ccc ctg gga atg gct tct gga cac att aga gat ttt cag att       4167
Gln Thr Pro Leu Gly Met Ala Ser Gly His Ile Arg Asp Phe Gln Ile
1130                1135                1140                1145 aca gct tca gga caa tat gga cag tgg gcc cca aag ctg gcc aga ctt       4215
Thr Ala Ser Gly Gln Tyr Gly Gln Trp Ala Pro Lys Leu Ala Arg Leu
```

```
                    1150              1155              1160
cat tat tcc gga tca atc aat gcc tgg agc acc aag gag ccc ttt tct      4263
His Tyr Ser Gly Ser Ile Asn Ala Trp Ser Thr Lys Glu Pro Phe Ser
                1165              1170              1175 tgg atc aag gtg gat ctg ttg gca cca atg att att cac ggc atc aag      4311
Trp Ile Lys Val Asp Leu Leu Ala Pro Met Ile Ile His Gly Ile Lys
            1180              1185              1190 acc cag ggt gcc cgt cag aag ttc tcc agc ctc tac atc tct cag ttt      4359
Thr Gln Gly Ala Arg Gln Lys Phe Ser Ser Leu Tyr Ile Ser Gln Phe
        1195              1200              1205 atc atc atg tat agt ctt gat ggg aag aag tgg cag act tat cga gga      4407
Ile Ile Met Tyr Ser Leu Asp Gly Lys Lys Trp Gln Thr Tyr Arg Gly
1210              1215              1220              1225 aat tcc act gga acc tta atg gtc ttc ttt ggc aat gtg gat tca tct      4455
Asn Ser Thr Gly Thr Leu Met Val Phe Phe Gly Asn Val Asp Ser Ser
                1230              1235              1240 ggg ata aaa cac aat att ttt aac cct cca att att gct cga tac atc      4503
Gly Ile Lys His Asn Ile Phe Asn Pro Pro Ile Ile Ala Arg Tyr Ile
            1245              1250              1255 cgt ttg cac cca act cat tat agc att cgc agc act ctt cgc atg gag      4551
Arg Leu His Pro Thr His Tyr Ser Ile Arg Ser Thr Leu Arg Met Glu
        1260              1265              1270 ttg atg ggc tgt gat tta aat agt tgc agc atg cca ttg gga atg gag      4599
Leu Met Gly Cys Asp Leu Asn Ser Cys Ser Met Pro Leu Gly Met Glu
1275              1280              1285 agt aaa gca ata tca gat gca cag att act gct tca tcc tac ttt acc      4647
Ser Lys Ala Ile Ser Asp Ala Gln Ile Thr Ala Ser Ser Tyr Phe Thr
1290              1295              1300              1305 aat atg ttt gcc acc tgg tct cct tca aaa gct cga ctt cac ctc caa      4695
Asn Met Phe Ala Thr Trp Ser Pro Ser Lys Ala Arg Leu His Leu Gln
                1310              1315              1320 ggg agg agt aat gcc tgg aga cct cag gag aat aat cca aaa gag tgg      4743
Gly Arg Ser Asn Ala Trp Arg Pro Gln Glu Asn Asn Pro Lys Glu Trp
            1325              1330              1335 ctg caa gtg gac ttc cag aag aca atg aaa gtc aca gga gta act act      4791
Leu Gln Val Asp Phe Gln Lys Thr Met Lys Val Thr Gly Val Thr Thr
        1340              1345              1350 cag gga gta aaa tct ctg ctt acc agc atg tat gtg aag gag ttc ctc      4839
Gln Gly Val Lys Ser Leu Leu Thr Ser Met Tyr Val Lys Glu Phe Leu
1355              1360              1365 atc tcc agc agt caa gat ggc cat cag tgg acc ctc ttt ttt cag aat      4887
Ile Ser Ser Ser Gln Asp Gly His Gln Trp Thr Leu Phe Phe Gln Asn
1370              1375              1380              1385 ggc aaa gta aag gtt ttt cag gga aat caa gac tcc ttc aca cct gtg      4935
Gly Lys Val Lys Val Phe Gln Gly Asn Gln Asp Ser Phe Thr Pro Val
                1390              1395              1400 gtg aac tct cta gac cca ccg tta ctg act cgc tac ctt cga att cac      4983
Val Asn Ser Leu Asp Pro Pro Leu Leu Thr Arg Tyr Leu Arg Ile His
            1405              1410              1415 ccc cag agt tgg gtg cac cag att gcc ctg agg atg gag gtt ctg ggc      5031
Pro Gln Ser Trp Val His Gln Ile Ala Leu Arg Met Glu Val Leu Gly
        1420              1425              1430 tgc gag gca cag gac ctc tac tgagcggccg cgactctact agaggatctt        5082
Cys Glu Ala Gln Asp Leu Tyr
1435              1440 tgtgaaggaa ccttacttct gtggtgtgac ataattggac aaactaccta cagagattta    5142
aagctctaag gtaaatataa aattttttaag tgtataatgt gttaaactac tgattctaat   5202
tgtttgtgta ttttagattc caacctatgg aactgatgaa tgggagcagt ggtggaatgc    5262
```

```
ctttaatgag gaaaacctgt tttgctcaga agaaatgcca tctagtgatg atgaggctac   5322
tgctgactct caacattcta ctcctccaaa aaagaagaga aaggtagaag accccaagga   5382
ctttccttca gaattgctaa gttttttgag tcatgctgtg tttagtaata gaactcttgc   5442
ttgctttgct atttacacca caaaggaaaa agctgcactg ctatacaaga aaattatgga   5502
aaaatattct gtaacctttta taagtaggca taacagttat aatcataaca tactgttttt   5562
tcttactcca cacaggcata gagtgtctgc tattaataac tatgctcaaa aattgtgtac   5622
ctttagcttt ttaatttgta aaggggttaa taaggaatat ttgatgtata gtgccttgac   5682
tagagatcat aatcagccat accacatttg tagaggtttt acttgcttta aaaaacctcc   5742
cacacctccc cctgaacctg aaacataaaa tgaatgcaat tgttgttgtt aacttgttta   5802
ttgcagctta taatggttac aaataaagca atagcatcac aaatttcaca aataaagcat   5862
ttttttcact gcattctagt tgtggtttgt ccaaactcat caatgtatct tatcatgtct   5922
ggatccccgg gtaccctcta gagcgaatta attcactggc cgtcgtttta caacgtcgtg   5982
actgggaaaa ccctggcgtt acccaactta atcgccttgc agcacatccc cctttcgcca   6042
gctggcgtaa tagcgaagag gcccgcaccg atcgccttc caacagttg cgcagcctga   6102 atggcgaatg cgcctgatg cggtattttc tccttacgca tctgtgcggt atttcacacc   6162
gcatatggtg cactctcagt acaatctgct ctgatgccgc atagttaagc cagccccgac   6222
acccgccaac acccgctgac gcgccctgac gggcttgtct gctcccggca tccgcttaca   6282
gacaagctgt gaccgtctcc gggagctgca tgtgtcagag gttttcaccg tcatcaccga   6342
aacgcgcgag acgaaagggg gggtaccagc ttcgtagcta aacatcatg ttctgggata   6402 tcagcttcgt agctagaaca tcatgttctg gtaccccct cgtgatacgc ctattttat   6462 aggttaatgt catgataata atggtttctt agacgtcagg tggcactttt cggggaaatg   6522
tgcgcggaac ccctatttgt ttatttttct aaatacattc aaatatgtat ccgctcatga   6582
gacaataacc ctgataaatg cttcaataat attgaaaaag gaagagtatg agtattcaac   6642
atttccgtgt cgcccttatt cccttttttg cggcattttg ccttcctgtt tttgctcacc   6702
cagaaacgct ggtgaaagta aaagatgctg aagatcagtt gggtgcacga gtgggttaca   6762
tcgaactgga tctcaacagc ggtaagatcc ttgagagttt cgccccgaa gaacgttttc   6822 caatgatgag cacttttaaa gttctgctat gtggcgcggt attatcccgt attgacgccg   6882
ggcaagagca actcggtcgc cgcatacact attctcagaa tgacttggtt gagtactcac   6942
cagtcacaga aaagcatctt acggatggca tgacagtaag agaattatgc agtgctgcca   7002
taaccatgag tgataacact gcggccaact tacttctgac aacgatcgga ggaccgaagg   7062
agctaaccgc ttttttgcac aacatggggg atcatgtaac tcgccttgat cgttgggaac   7122
cggagctgaa tgaagccata ccaaacgacg agcgtgacac cacgatgcct gtagcaatgg   7182
caacaacgtt gcgcaaacta ttaactggcg aactacttac tctagcttcc cggcaacaat   7242
taatagactg gatggaggcg gataaagttg caggaccact tctgcgctcg gcccttccgg   7302
ctggctggtt tattgctgat aaatctggag ccggtgagcg tgggtctcgc ggtatcattg   7362
cagcactggg gccagatggt aagccctccc gtatcgtagt tatctacacg acggggagtc   7422
aggcaactat ggatgaacga atagacaga tcgctgagat aggtgcctca ctgattaagc   7482
attggtaact gtcagaccaa gtttactcat atatacttta gattgattta aaacttcatt   7542
tttaatttaa aaggatctag gtgaagatcc ttttgataa tctcatgacc aaaatccctt   7602
```

```
aacgtgagtt tcgttccac tgagcgtcag accccgtaga aaagatcaaa ggatcttctt    7662
gagatccttt ttttctgcgc gtaatctgct gcttgcaaac aaaaaaacca ccgctaccag    7722
cggtggtttg tttgccggat caagagctac caactctttt tccgaaggta actggcttca    7782
gcagagcgca gataccaaat actgtcttct agtgtagccg tagttaggcc accacttcaa    7842
gaactctgta gcaccgccta catacctcgc tctgctaatc ctgttaccag tggctgctgc    7902
cagtggcgat aagtcgtgtc ttaccgggtt ggactcaaga cgatagttac cggataaggc    7962
gcagcggtcg ggctgaacgg ggggttcgtg cacacagccc agcttggagc gaacgaccta    8022
caccgaactg agatacctac agcgtgagct atgagaaagc gccacgcttc ccgaagggag    8082
aaaggcggac aggtatccgg taagcggcag ggtcggaaca ggagagcgca cgagggagct    8142
tccaggggga aacgcctggt atctttatag tcctgtcggg tttcgccacc tctgacttga    8202
gcgtcgattt ttgtgatgct cgtcaggggg cggagccta tggaaaaacg ccagcaacgc     8262 ggcctttttta cggttcctgg cctttttgctg gccttttgct cacatgttct ttcctgcgtt    8322
atcccctgat tctgtggata accgtattac cgcctttgag tgagctgata ccgctcgccg    8382
cagccgaacg accgagcgca gcgagtcagt gagcgaggaa gcggaagagc gcccaatacg    8442
caaaccgcct ctccccgcgc gttggccgat tcattaatgc agctggcacg acaggtttcc    8502
cgactggaaa gcgggcagtg agcgcaacgc aattaatgtg agttagctca ctcattaggc    8562
accccaggct ttacacttta tgcttccggc tcgtatgttg tgtggaattg tgagcggata    8622
acaatttcac acaggaaaca gctatgacca tgattacgcc aagctctcta gagctctaga    8682
gctctagagc tctagagagc ttgcatgcct gcaggtcg                            8720
```

<210> SEQ ID NO 4
<211> LENGTH: 1459
<212> TYPE: PRT
<213> ORGANISM: Artificial Sequence
<220> FEATURE:
<223> OTHER INFORMATION: factor VIII protein encoded by pTGF8-1

<400> SEQUENCE: 4

```
Met Gln Ile Glu Leu Ser Thr Cys Phe Phe Leu Cys Leu Leu Arg Phe
            -15                 -10                  -5

Cys Phe Ser Ala Thr Arg Arg Tyr Tyr Leu Gly Ala Val Glu Leu Ser
     -1   1                   5                  10

Trp Asp Tyr Met Gln Ser Asp Leu Gly Glu Leu Pro Val Asp Ala Arg
         15                  20                  25

Phe Pro Pro Arg Val Pro Lys Ser Phe Pro Phe Asn Thr Ser Val Val
 30                  35                  40                  45

Tyr Lys Lys Thr Leu Phe Val Glu Phe Thr Asp His Leu Phe Asn Ile
             50                  55                  60

Ala Lys Pro Arg Pro Pro Trp Met Gly Leu Leu Gly Pro Thr Ile Gln
             65                  70                  75

Ala Glu Val Tyr Asp Thr Val Val Ile Thr Leu Lys Asn Met Ala Ser
         80                  85                  90

His Pro Val Ser Leu His Ala Val Gly Val Ser Tyr Trp Lys Ala Ser
     95                 100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                130                 135                 140

Lys Glu Asn Gly Pro Met Ala Ser Asp Pro Leu Cys Leu Thr Tyr Ser
```

```
                    145                 150                 155
Tyr Leu Ser His Ala Asp Leu Val Lys Asp Leu Asn Ser Gly Leu Ile
                160                 165                 170
Gly Ala Leu Leu Val Cys Arg Glu Gly Ser Leu Ala Lys Glu Lys Thr
            175                 180                 185
Gln Thr Leu His Lys Phe Ile Leu Leu Phe Ala Val Phe Asp Glu Gly
190                 195                 200                 205
Lys Ser Trp His Ser Glu Thr Lys Asn Ser Leu Met Gln Asp Arg Asp
                210                 215                 220
Ala Ala Ser Ala Arg Ala Trp Pro Lys Met His Thr Val Asn Gly Tyr
            225                 230                 235
Val Asn Arg Ser Leu Pro Gly Leu Ile Gly Cys His Arg Lys Ser Val
        240                 245                 250
Tyr Trp His Val Ile Gly Met Gly Thr Thr Pro Glu Val His Ser Ile
        255                 260                 265
Phe Leu Glu Gly His Thr Phe Leu Val Arg Asn His Arg Gln Ala Ser
270                 275                 280                 285
Leu Glu Ile Ser Pro Ile Thr Phe Leu Thr Ala Gln Thr Leu Leu Met
                290                 295                 300
Asp Leu Gly Gln Phe Leu Leu Phe Cys His Ile Ser Ser His Gln His
            305                 310                 315
Asp Gly Met Glu Ala Tyr Val Lys Val Asp Ser Cys Pro Glu Glu Pro
        320                 325                 330
Gln Leu Arg Met Lys Asn Asn Glu Glu Ala Glu Asp Tyr Asp Asp Asp
        335                 340                 345
Leu Thr Asp Ser Glu Met Asp Val Val Arg Phe Asp Asp Asn Ser
350                 355                 360                 365
Pro Ser Phe Ile Gln Ile Arg Ser Val Ala Lys Lys His Pro Lys Thr
                370                 375                 380
Trp Val His Tyr Ile Ala Ala Glu Glu Asp Trp Asp Tyr Ala Pro
            385                 390                 395
Leu Val Leu Ala Pro Asp Asp Arg Ser Tyr Lys Ser Gln Tyr Leu Asn
        400                 405                 410
Asn Gly Pro Gln Arg Ile Gly Arg Lys Tyr Lys Lys Val Arg Phe Met
        415                 420                 425
Ala Tyr Thr Asp Glu Thr Phe Lys Thr Arg Glu Ala Ile Gln His Glu
430                 435                 440                 445
Ser Gly Ile Leu Gly Pro Leu Leu Tyr Gly Glu Val Gly Asp Thr Leu
                450                 455                 460
Leu Ile Ile Phe Lys Asn Gln Ala Ser Arg Pro Tyr Asn Ile Tyr Pro
            465                 470                 475
His Gly Ile Thr Asp Val Arg Pro Leu Tyr Ser Arg Arg Leu Pro Lys
        480                 485                 490
Gly Val Lys His Leu Lys Asp Phe Pro Ile Leu Pro Gly Glu Ile Phe
        495                 500                 505
Lys Tyr Lys Trp Thr Val Thr Val Glu Asp Gly Pro Thr Lys Ser Asp
510                 515                 520                 525
Pro Arg Cys Leu Thr Arg Tyr Tyr Ser Ser Phe Val Asn Met Glu Arg
                530                 535                 540
Asp Leu Ala Ser Gly Leu Ile Gly Pro Leu Leu Ile Cys Tyr Lys Glu
            545                 550                 555
Ser Val Asp Gln Arg Gly Asn Gln Ile Met Ser Asp Lys Arg Asn Val
        560                 565                 570
```

```
Ile Leu Phe Ser Val Phe Asp Glu Asn Arg Ser Trp Tyr Leu Thr Glu
    575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620

Phe Asp Ser Leu Gln Leu Ser Val Cys Leu His Glu Val Ala Tyr Trp
                625                 630                 635

Tyr Ile Leu Ser Ile Gly Ala Gln Thr Asp Phe Leu Ser Val Phe Phe
                640                 645                 650

Ser Gly Tyr Thr Phe Lys His Lys Met Val Tyr Glu Asp Thr Leu Thr
    655                 660                 665

Leu Phe Pro Phe Ser Gly Glu Thr Val Phe Met Ser Met Glu Asn Pro
670                 675                 680                 685

Gly Leu Trp Ile Leu Gly Cys His Asn Ser Asp Phe Arg Asn Arg Gly
                690                 695                 700

Met Thr Ala Leu Leu Lys Val Ser Ser Cys Asp Lys Asn Thr Gly Asp
                705                 710                 715

Tyr Tyr Glu Asp Ser Tyr Glu Asp Ile Ser Ala Tyr Leu Leu Ser Lys
            720                 725                 730

Asn Asn Ala Ile Glu Pro Arg Ser Phe Ser Gln Asn Ser Arg His Gln
    735                 740                 745

Ala Tyr Arg Tyr Arg Arg Gly Glu Ile Thr Arg Thr Thr Leu Gln Ser
750                 755                 760                 765

Asp Gln Glu Glu Ile Asp Tyr Asp Asp Thr Ile Ser Val Glu Met Lys
                770                 775                 780

Lys Glu Asp Phe Asp Ile Tyr Asp Glu Asp Glu Asn Gln Ser Pro Arg
                785                 790                 795

Ser Phe Gln Lys Lys Thr Arg His Tyr Phe Ile Ala Ala Val Glu Arg
                800                 805                 810

Leu Trp Asp Tyr Gly Met Ser Ser Ser Pro His Val Leu Arg Asn Arg
    815                 820                 825

Ala Gln Ser Gly Ser Val Pro Gln Phe Lys Lys Val Val Phe Gln Glu
830                 835                 840                 845

Phe Thr Asp Gly Ser Phe Thr Gln Pro Leu Tyr Arg Gly Glu Leu Asn
                850                 855                 860

Glu His Leu Gly Leu Leu Gly Pro Tyr Ile Arg Ala Glu Val Glu Asp
                865                 870                 875

Asn Ile Met Val Thr Phe Arg Asn Gln Ala Ser Arg Pro Tyr Ser Phe
                880                 885                 890

Tyr Ser Ser Leu Ile Ser Tyr Glu Glu Asp Gln Arg Gln Gly Ala Glu
    895                 900                 905

Pro Arg Lys Asn Phe Val Lys Pro Asn Glu Thr Lys Thr Tyr Phe Trp
910                 915                 920                 925

Lys Val Gln His His Met Ala Pro Thr Lys Asp Glu Phe Asp Cys Lys
                930                 935                 940

Ala Trp Ala Tyr Phe Ser Asp Val Asp Leu Glu Lys Asp Val His Ser
                945                 950                 955

Gly Leu Ile Gly Pro Leu Leu Val Cys His Thr Asn Thr Leu Asn Pro
    960                 965                 970

Ala His Gly Arg Gln Val Thr Val Gln Glu Phe Ala Leu Phe Phe Thr
975                 980                 985
```

```
Ile Phe Asp Glu Thr Lys Ser Trp Tyr Phe Thr Glu Asn Met Glu Arg
990                 995                 1000                1005

Asn Cys Arg Ala Pro Cys Asn Ile Gln Met Glu Asp Pro Thr Phe Lys
            1010                1015                1020

Glu Asn Tyr Arg Phe His Ala Ile Asn Gly Tyr Ile Met Asp Thr Leu
        1025                1030                1035

Pro Gly Leu Val Met Ala Gln Asp Gln Arg Ile Arg Trp Tyr Leu Leu
    1040                1045                1050

Ser Met Gly Ser Asn Glu Asn Ile His Ser Ile His Phe Ser Gly His
    1055                1060                1065

Val Phe Thr Val Arg Lys Lys Glu Glu Tyr Lys Met Ala Leu Tyr Asn
1070                1075                1080                1085

Leu Tyr Pro Gly Val Phe Glu Thr Val Glu Met Leu Pro Ser Lys Ala
        1090                1095                1100

Gly Ile Trp Arg Val Glu Cys Leu Ile Gly Glu His Leu His Ala Gly
            1105                1110                1115

Met Asn Thr Leu Phe Leu Val Tyr Ser Asn Lys Cys Gln Thr Pro Leu
        1120                1125                1130

Gly Met Ala Ser Gly His Ile Arg Asp Phe Gln Ile Thr Ala Ser Gly
    1135                1140                1145

Gln Tyr Gly Gln Trp Ala Pro Lys Leu Ala Arg Leu His Tyr Ser Gly
1150                1155                1160                1165

Ser Ile Asn Ala Trp Ser Thr Lys Glu Pro Phe Ser Trp Ile Lys Val
            1170                1175                1180

Asp Leu Leu Ala Pro Met Ile Ile His Gly Ile Lys Thr Gln Gly Ala
        1185                1190                1195

Arg Gln Lys Phe Ser Ser Leu Tyr Ile Ser Gln Phe Ile Ile Met Tyr
    1200                1205                1210

Ser Leu Asp Gly Lys Lys Trp Gln Thr Tyr Arg Gly Asn Ser Thr Gly
    1215                1220                1225

Thr Leu Met Val Phe Phe Gly Asn Val Asp Ser Ser Gly Ile Lys His
1230                1235                1240                1245

Asn Ile Phe Asn Pro Pro Ile Ile Ala Arg Tyr Ile Arg Leu His Pro
            1250                1255                1260

Thr His Tyr Ser Ile Arg Ser Thr Leu Arg Met Glu Leu Met Gly Cys
        1265                1270                1275

Asp Leu Asn Ser Cys Ser Met Pro Leu Gly Met Glu Ser Lys Ala Ile
        1280                1285                1290

Ser Asp Ala Gln Ile Thr Ala Ser Ser Tyr Phe Thr Asn Met Phe Ala
    1295                1300                1305

Thr Trp Ser Pro Ser Lys Ala Arg Leu His Leu Gln Gly Arg Ser Asn
1310                1315                1320                1325

Ala Trp Arg Pro Gln Glu Asn Asn Pro Lys Glu Trp Leu Gln Val Asp
            1330                1335                1340

Phe Gln Lys Thr Met Lys Val Thr Gly Val Thr Thr Gln Gly Val Lys
        1345                1350                1355

Ser Leu Leu Thr Ser Met Tyr Val Lys Glu Phe Leu Ile Ser Ser Ser
        1360                1365                1370

Gln Asp Gly His Gln Trp Thr Leu Phe Phe Gln Asn Gly Lys Val Lys
    1375                1380                1385

Val Phe Gln Gly Asn Gln Asp Ser Phe Thr Pro Val Val Asn Ser Leu
1390                1395                1400                1405

Asp Pro Pro Leu Leu Thr Arg Tyr Leu Arg Ile His Pro Gln Ser Trp
```

-continued

```
                1410                1415                1420
Val His Gln Ile Ala Leu Arg Met Glu Val Leu Gly Cys Glu Ala Gln
            1425                1430                1435

Asp Leu Tyr
        1440

<210> SEQ ID NO 5
<211> LENGTH: 461
<212> TYPE: PRT
<213> ORGANISM: Homo sapiens

<400> SEQUENCE: 5

Met Gln Arg Val Asn Met Ile Met Ala Glu Ser Pro Gly Leu Ile Thr
  1               5                  10                  15

Ile Cys Leu Leu Gly Tyr Leu Leu Ser Ala Glu Cys Thr Val Phe Leu
                 20                  25                  30

Asp His Glu Asn Ala Asn Lys Ile Leu Asn Arg Pro Lys Arg Tyr Asn
             35                  40                  45

Ser Gly Lys Leu Glu Glu Phe Val Gln Gly Asn Leu Glu Arg Glu Cys
 50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335
```

```
Ala Asp Lys Glu Tyr Thr Asn Ile Phe Leu Lys Phe Gly Ser Gly Tyr
        340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
        450                 455                 460

<210> SEQ ID NO 6
<211> LENGTH: 5753
<212> TYPE: DNA
<213> ORGANISM: Artificial Sequence
<220> FEATURE:
<223> OTHER INFORMATION: pTGFG36

<400> SEQUENCE: 6
cgcgttgaca ttgattattg actagttatt aatagtaatc aattacgggg tcattagttc      60
atagcccata tatggagttc cgcgttacat aacttacggt aaatggcccg cctggctgac     120
cgcccaacga cccccgccca ttgacgtcaa taatgacgta tgttcccata gtaacgccaa     180
tagggacttt ccattgacgt caatgggtgg agtatttacg gtaaactgcc cacttggcag     240
tacatcaagt gtatcatatg ccaagtacgc cccctattga cgtcaatgac ggtaaatggc     300
ccgcctggca ttatgcccag tacatgacct tatgggactt tcctacttgg cagtacatct     360
acgtattagt catcgctatt accatggtga tgcggttttg gcagtacatc aatgggcgtg     420
gatagcggtt tgactcacgg ggatttccaa gtctccaccc cattgacgtc aatgggagtt     480
tgttttggca ccaaaatcaa cgggactttc caaaatgtcg taacaactcc gccccattga     540
cgcaaatggg cggtaggcgt gtacggtggg aggtctatat aagcagagct ctctggctaa     600
ctagagaacc cactgcttac tggcttatcg aaattaatac gactcactat agggagaccc     660
aagcttgcat gccaattccg caaaggttat gcagcgcgtg aacatgatca tggcagaatc     720
accaggcctc atcaccatct gccttttagg atatctactc agtgctgaat gtacagtttt     780
tcttgatcat gaaaacgcca acaaaattct gaatcggcca agaggtata attcaggtaa     840 attggaagag tttgttcaag gaaccttga gagagaatgt atggaagaaa agtgtagttt     900
tgaagaagca cgagaagttt ttgaaaacac tgaaagaaca actgaatttt ggaagcagta     960
tgttgatgga gatcagtgtg agtccaatcc atgtttaaat ggcggcagtt gcaaggatga    1020
cattaattcc tatgaatgtt ggtgtcccct tggatttgaa ggaaagaact gtgaattaga    1080
tgtaacatgt aacattaaga atggcagatg cgagcagttt tgtaaaaata gtgctgataa    1140
caaggtggtt tgctcctgta ctgagggata tcgacttgca gaaaaccaga gtcctgtga    1200 accagcagtg ccatttccat gtggaagagt ttctgtttca caaacttcta agctcacccg    1260
tgctgagact gttttttcctg atgtggacta tgtaaattct actgaagctg aaaccatttt    1320
ggataacatc actcaaagca cccaatcatt taatgacttc actcggggttg ttggtggaga    1380
```

```
agatgccaaa ccaggtcaat tcccttggca ggttgttttg aatggtaaag ttgatgcatt      1440
ctgtggaggc tctatcgtta atgaaaaatg gattgtaact gctgcccact gtgttgaaac      1500
tggtgttaaa attacagttg tcgcaggtga acataatatt gaggagacag aacatacaga      1560
gcaaaagcga aatgtgattc gaattattcc tcaccacaac tacaatgcag ctattaataa      1620
gtacaaccat gacattgccc ttctggaact ggacgaaccc ttagtgctaa acagctacgt      1680
tacacctatt tgcattgctg acaaggaata cacgaacatc ttcctcaaat tggatctgg       1740 ctatgtaagt ggctggggaa gagtcttcca caaagggaga tcagctttag ttcttcagta      1800
ccttagagtt ccacttgttg accgagccac atgtcttcga tctacaaagt tcaccatcta      1860
taacaacatg ttctgtgctg gcttccatga aggaggtaga gattcatgtc aaggagatag      1920
tgggggaccc catgttactg aagtggaagg gaccagtttc ttaactggaa ttattagctg      1980
gggtgaagag tgtgcaatga aaggcaaata tggaatatat accaaggtat cccggtatgt      2040
caactggatt aaggaaaaaa caaagctcac ttaatgggat cggtcgagcg gccgcgactc      2100
tactagagga tctttgtgaa ggaaccttac ttctgtggtg tgacataatt ggacaaacta      2160
cctacagaga tttaaagctc taaggtaaat ataaaatttt taagtgtata atgtgttaaa      2220
ctactgattc taattgtttg tgtattttag attccaacct atggaactga tgaatgggag      2280
cagtggtgga atgcctttaa tgaggaaaac ctgttttgct cagaagaaat gccatctagt      2340
gatgatgagg ctactgctga ctctcaacat tctactcctc caaaaaagaa gagaaaggta      2400
gaagacccca aggactttcc ttcagaattg ctaagttttt tgagtcatgc tgtgtttagt      2460
aatagaactc ttgcttgctt tgctatttac accacaaagg aaaaagctgc actgctatac      2520
aagaaaatta tggaaaaata ttctgtaacc tttataagta ggcataacag ttataatcat      2580
aacatactgt ttttttcttac tccacacagg catagagtgt ctgctattaa taactatgct      2640
caaaaattgt gtacctttag cttttttaatt tgtaaagggg ttaataagga atatttgatg      2700
tatagtgcct tgactagaga tcataatcag ccataccaca tttgtagagg ttttacttgc      2760
tttaaaaaac ctcccacacc tccccctgaa cctgaaacat aaaatgaatg caattgttgt      2820
tgttaacttg tttattgcag cttataatgg ttacaaataa agcaatagca tcacaaattt      2880
cacaaataaa gcatttttt cactgcattc tagttgtggt ttgtccaaac tcatcaatgt       2940
atcttatcat gtctggatcc ccgggtaccc tctagagcga attaattcac tggccgtcgt      3000
tttacaacgt cgtgactggg aaaaccctgg cgttacccaa cttaatcgcc ttgcagcaca      3060
tccccctttc gccagctggc gtaatagcga agaggcccgc accgatcgcc cttcccaaca      3120
gttgcgcagc ctgaatggcg aatggcgcct gatgcggtat tttctcctta cgcatctgtg      3180
cggtatttca caccgcatat ggtgcactct cagtacaatc tgctctgatg ccgcatagtt      3240
aagccagccc cgacacccgc caacacccgc tgacgcgccc tgacgggctt gtctgctccc      3300
ggcatccgct tacagacaag ctgtgaccgt ctccgggagc tgcatgtgtc agaggttttc      3360
accgtcatca ccgaaacgcg cgagacgaaa gggggtac cagcttcgta gctagaacat      3420
catgttctgg gatatcagct tcgtagctag aacatcatgt tctggtaccc cctcgtgat     3480 acgcctattt ttataggtta atgtcatgat aataatggtt tcttagacgt caggtggcac      3540
ttttcgggga atgtgcgcg gaaccccctat ttgttattt ttctaaatac attcaaatat       3600
gtatccgctc atgagacaat aaccctgata aatgcttcaa taatattgaa aaaggaagag      3660
tatgagtatt caacatttcc gtgtcgccct tattccctt tttgcggcat tttgccttcc       3720
```

-continued

```
tgttttttgct cacccagaaa cgctggtgaa agtaaaagat gctgaagatc agttgggtgc    3780
acgagtgggt tacatcgaac tggatctcaa cagcggtaag atccttgaga gttttcgccc    3840
cgaagaacgt tttccaatga tgagcacttt taaagttctg ctatgtggcg cggtattatc    3900
ccgtattgac gccgggcaag agcaactcgg tcgccgcata cactattctc agaatgactt    3960
ggttgagtac tcaccagtca cagaaaagca tcttacggat ggcatgacag taagagaatt    4020
atgcagtgct gccataacca tgagtgataa cactgcggcc aacttacttc tgacaacgat    4080
cggaggaccg aaggagctaa ccgcttttt  gcacaacatg ggggatcatg taactcgcct    4140
tgatcgttgg gaaccggagc tgaatgaagc cataccaaac gacgagcgtg acaccacgat    4200
gcctgtagca atggcaacaa cgttgcgcaa actattaact ggcgaactac ttactctagc    4260
ttcccggcaa caattaatag actggatgga ggcggataaa gttgcaggac cacttctgcg    4320
ctcggccctt ccggctggct ggtttattgc tgataaatct ggagccggtg agcgtgggtc    4380
tcgcggtatc attgcagcac tggggccaga tggtaagccc tcccgtatcg tagttatcta    4440
cacgacgggg agtcaggcaa ctatggatga acgaaataga cagatcgctg agataggtgc    4500
ctcactgatt aagcattggt aactgtcaga ccaagtttac tcatatatac tttagattga    4560
tttaaaactt cattttttaat ttaaaaggat ctaggtgaag atcctttttg ataatctcat    4620
gaccaaaatc ccttaacgtg agttttcgtt ccactgagcg tcagaccccg tagaaaagat    4680
caaaggatct cttgagatc  cttttttttct gcgcgtaatc tgctgcttgc aaacaaaaaa    4740
accaccgcta ccagcggtgg tttgtttgcc ggatcaagag ctaccaactc ttttttccgaa   4800
ggtaactggc ttcagcagag cgcagatacc aaatactgtt cttctagtgt agccgtagtt    4860
aggccaccac ttcaagaact ctgtagcacc gcctacatac ctcgctctgc taatcctgtt    4920
accagtggct gctgccagtg gcgataagtc gtgtcttacc gggttggact caagacgata    4980
gttaccggat aaggcgcagc ggtcgggctg aacggggggt tcgtgcacac agcccagctt    5040
ggagcgaacg acctacaccg aactgagata cctacagcgt gagctatgag aaagcgccac    5100
gcttcccgaa gggagaaagg cggacaggta tccggtaagc ggcagggtcg gaacaggaga    5160
gcgcacgagg gagcttccag ggggaaacgc ctggtatctt tatagtcctg tcgggtttcg    5220
ccacctctga cttgagcgtc gatttttgtg atgctcgtca ggggggcgga gcctatggaa    5280
aaacgccagc aacgcggcct ttttacggtt cctggccttt tgctggcctt ttgctcacat    5340
gttctttcct gcgttatccc ctgattctgt ggataaccgt attaccgcct ttgagtgagc    5400
tgataccgct cgccgcagcc gaacgaccga gcgcagcgag tcagtgagcg aggaagcgga    5460
agagcgccca atacgcaaac cgcctctccc cgcgcgttgg ccgattcatt aatgcagctg    5520
gcacgacagg tttcccgact ggaaagcggg cagtgagcgc aacgcaatta atgtgagtta    5580
gctcactcat taggcacccc aggctttaca ctttatgctt ccggctcgta tgttgtgtgg    5640
aattgtgagc ggataacaat ttcacacagg aaacagctat gaccatgatt acgccaagct    5700
ctctagagct ctagagctct agagctctag agagcttgca tgcctgcagg tcg           5753
```

<210> SEQ ID NO 7  
<211> LENGTH: 8  
<212> TYPE: PRT  
<213> ORGANISM: Artificial Sequence  
<220> FEATURE:  
<223> OTHER INFORMATION: B-domain linker peptide

<400> SEQUENCE: 7

Ser Phe Ser Gln Asn Ser Arg His

-continued

<210> SEQ ID NO 8
<211> LENGTH: 8
<212> TYPE: PRT
<213> ORGANISM: Artificial Sequence
<220> FEATURE:
<223> OTHER INFORMATION: B-domain linker peptide

<400> SEQUENCE: 8

Gln Ala Tyr Arg Tyr Arg Arg Gly
 1               5

<210> SEQ ID NO 9
<211> LENGTH: 16
<212> TYPE: PRT
<213> ORGANISM: Artificial Sequence
<220> FEATURE:
<223> OTHER INFORMATION: B-domain linker peptide

<400> SEQUENCE: 9

Ser Phe Ser Gln Asn Ser Arg His Gln Ala Tyr Arg Tyr Arg Arg Gly
 1               5                   10                  15

<210> SEQ ID NO 10
<211> LENGTH: 78
<212> TYPE: DNA
<213> ORGANISM: Homo sapiens

<400> SEQUENCE: 10
ggggtaccag cttcgtagct agaacatcat gttctgggat atcagcttcg tagctagaac     60
atcatgttct ggtacccc                                                   78

<210> SEQ ID NO 11
<211> LENGTH: 78
<212> TYPE: DNA
<213> ORGANISM: Homo sapiens

<400> SEQUENCE: 11
ggggtaccag aacatgatgt tctagctacg aagctgatat cccagaacat gatgttctag     60
ctacgaagct ggtacccc                                                   78

<210> SEQ ID NO 12
<211> LENGTH: 10698
<212> TYPE: DNA
<213> ORGANISM: Artificial Sequence
<220> FEATURE:
<223> OTHER INFORMATION: pTGF8-2hyg-s
<220> FEATURE:
<221> NAME/KEY: CDS
<222> LOCATION: (676)..(5052)
<220> FEATURE:
<221> NAME/KEY: mat_peptide
<222> LOCATION: (733)..(5052)

<400> SEQUENCE: 12
cgcgttgaca ttgattattg actagttatt aatagtaatc aattacgggg tcattagttc     60
atagcccata tatggagttc cgcgttacat aacttacggt aaatggcccg cctggctgac    120
cgcccaacga cccccgccca ttgacgtcaa taatgacgta tgttcccata gtaacgccaa    180
tagggacttt ccattgacgt caatgggtgg agtatttacg gtaaactgcc cacttggcag    240
tacatcaagt gtatcatatg ccaagtacgc cccctattga cgtcaatgac ggtaaatggc    300
ccgcctggca ttatgcccag tacatgacct tatgggactt tcctacttgg cagtacatct    360

-continued

```
acgtattagt catcgctatt accatggtga tgcggttttg gcagtacatc aatgggcgtg        420
gatagcggtt tgactcacgg ggatttccaa gtctccaccc cattgacgtc aatgggagtt        480
tgttttggca ccaaaatcaa cgggactttc caaaatgtcg taacaactcc gccccattga        540
cgcaaatggg cggtaggcgt gtacggtggg aggtctatat aagcagagct ctctggctaa        600
ctagagaacc cactgcttac tggcttatcg aaattaatac gactcactat agggagaccc        660
aagcttgacc tcgag atg caa ata gag ctc tcc acc tgc ttc ttt ctg tgc        711
             Met Gln Ile Glu Leu Ser Thr Cys Phe Phe Leu Cys
                        -15              -10 ctt ttg cga ttc tgc ttt agt gcc acc aga aga tac tac ctg ggt gca        759
Leu Leu Arg Phe Cys Phe Ser Ala Thr Arg Arg Tyr Tyr Leu Gly Ala
       -5                  -1  1              5 gtg gaa ctg tca tgg gac tat atg caa agt gat ctc ggt gag ctg cct        807
Val Glu Leu Ser Trp Asp Tyr Met Gln Ser Asp Leu Gly Glu Leu Pro
 10              15                  20                  25 gtg gac gca aga ttt cct cct aga gtg cca aaa tct ttt cca ttc aac        855
Val Asp Ala Arg Phe Pro Pro Arg Val Pro Lys Ser Phe Pro Phe Asn
             30                  35                  40 acc tca gtc gtg tac aaa aag act ctg ttt gta gaa ttc acg gat cac        903
Thr Ser Val Val Tyr Lys Lys Thr Leu Phe Val Glu Phe Thr Asp His
                 45                  50                  55 ctt ttc aac atc gct aag cca agg cca ccc tgg atg ggt ctg cta ggt        951
Leu Phe Asn Ile Ala Lys Pro Arg Pro Pro Trp Met Gly Leu Leu Gly
             60                  65                  70 cct acc atc cag gct gag gtt tat gat aca gtg gtc att aca ctt aag        999
Pro Thr Ile Gln Ala Glu Val Tyr Asp Thr Val Val Ile Thr Leu Lys
 75                  80                  85 aac atg gct tcc cat cct gtc agt ctt cat gct gtt ggt gta tcc tac       1047
Asn Met Ala Ser His Pro Val Ser Leu His Ala Val Gly Val Ser Tyr
 90                  95                 100                 105 tgg aaa gct tct gag gga gct gaa tat gat gat cag acc agt caa agg       1095
Trp Lys Ala Ser Glu Gly Ala Glu Tyr Asp Asp Gln Thr Ser Gln Arg
                110                 115                 120 gag aaa gaa gat gat aaa gtc ttc cct ggt gga agc cat aca tat gtc       1143
Glu Lys Glu Asp Asp Lys Val Phe Pro Gly Gly Ser His Thr Tyr Val
            125                 130                 135 tgg cag gtc ctg aaa gag aat ggt cca atg gcc tct gac cca ctg tgc       1191
Trp Gln Val Leu Lys Glu Asn Gly Pro Met Ala Ser Asp Pro Leu Cys
            140                 145                 150 ctt acc tac tca tat ctt tct cat gtg gac ctg gta aaa gac ttg aat       1239
Leu Thr Tyr Ser Tyr Leu Ser His Val Asp Leu Val Lys Asp Leu Asn
155                 160                 165 tca ggc ctc att gga gcc cta cta gta tgt aga gaa ggg agt ctg gcc       1287
Ser Gly Leu Ile Gly Ala Leu Leu Val Cys Arg Glu Gly Ser Leu Ala
170                 175                 180                 185 aag gaa aag aca cag acc ttg cac aaa ttt ata cta ctt ttt gct gta       1335
Lys Glu Lys Thr Gln Thr Leu His Lys Phe Ile Leu Leu Phe Ala Val
                190                 195                 200 ttt gat gaa ggg aaa agt tgg cac tca gaa aca aag aac tcc ttg atg       1383
Phe Asp Glu Gly Lys Ser Trp His Ser Glu Thr Lys Asn Ser Leu Met
            205                 210                 215 cag gat agg gat gct gca tct gct cgg gcc tgg cct aaa atg cac aca       1431
Gln Asp Arg Asp Ala Ala Ser Ala Arg Ala Trp Pro Lys Met His Thr
            220                 225                 230 gtc aat ggt tat gta aac agg tct ctg cca ggt ctg att gga tgc cac       1479
Val Asn Gly Tyr Val Asn Arg Ser Leu Pro Gly Leu Ile Gly Cys His
235                 240                 245
```

```
agg aaa tca gtc tat tgg cat gtg att gga atg ggc acc act cct gaa    1527
Arg Lys Ser Val Tyr Trp His Val Ile Gly Met Gly Thr Thr Pro Glu
250                 255                 260                 265 gtg cac tca ata ttc ctc gaa ggt cac aca ttt ctt gtg agg aac cat    1575
Val His Ser Ile Phe Leu Glu Gly His Thr Phe Leu Val Arg Asn His
            270                 275                 280 cgc cag gcg tcc ttg gaa atc tcg cca ata act ttc ctt act gct caa    1623
Arg Gln Ala Ser Leu Glu Ile Ser Pro Ile Thr Phe Leu Thr Ala Gln
        285                 290                 295 aca ctc ttg atg gac ctt gga cag ttt cta ctg ttt tgt cat atc tct    1671
Thr Leu Leu Met Asp Leu Gly Gln Phe Leu Leu Phe Cys His Ile Ser
    300                 305                 310 tcc cac caa cat gat ggc atg gaa gct tat gtc aaa gta gac agc tgt    1719
Ser His Gln His Asp Gly Met Glu Ala Tyr Val Lys Val Asp Ser Cys
315                 320                 325 cca gag gaa ccc caa cta cga atg aaa aat aat gaa gaa gcg gaa gac    1767
Pro Glu Glu Pro Gln Leu Arg Met Lys Asn Asn Glu Glu Ala Glu Asp
330                 335                 340                 345 tat gat gat gat ctt act gat tct gaa atg gat gtg gtc agg ttt gat    1815
Tyr Asp Asp Asp Leu Thr Asp Ser Glu Met Asp Val Val Arg Phe Asp
            350                 355                 360 gat gac aac tct cct tcc ttt atc caa att cgc tca gtt gcc aag aag    1863
Asp Asp Asn Ser Pro Ser Phe Ile Gln Ile Arg Ser Val Ala Lys Lys
        365                 370                 375 cat cct aaa act tgg gta cat tac att gct gct gaa gag gag gac tgg    1911
His Pro Lys Thr Trp Val His Tyr Ile Ala Ala Glu Glu Glu Asp Trp
    380                 385                 390 gac tat gct ccc tta gtc ctc gcc ccc gat gac aga agt tat aaa agt    1959
Asp Tyr Ala Pro Leu Val Leu Ala Pro Asp Asp Arg Ser Tyr Lys Ser
395                 400                 405 caa tat ttg aac aat ggc cct cag cgg att ggt agg aag tac aaa aaa    2007
Gln Tyr Leu Asn Asn Gly Pro Gln Arg Ile Gly Arg Lys Tyr Lys Lys
410                 415                 420                 425 gtc cga ttt atg gca tac aca gat gaa acc ttt aag act cgt gaa gct    2055
Val Arg Phe Met Ala Tyr Thr Asp Glu Thr Phe Lys Thr Arg Glu Ala
            430                 435                 440 att cag cat gaa tca gga atc ttg gga cct tta ctt tat ggg gaa gtt    2103
Ile Gln His Glu Ser Gly Ile Leu Gly Pro Leu Leu Tyr Gly Glu Val
        445                 450                 455 gga gac aca ctg ttg att ata ttt aag aat caa gca agc aga cca tat    2151
Gly Asp Thr Leu Leu Ile Ile Phe Lys Asn Gln Ala Ser Arg Pro Tyr
    460                 465                 470 aac atc tac cct cac gga atc act gat gtc cgt cct ttg tat tca agg    2199
Asn Ile Tyr Pro His Gly Ile Thr Asp Val Arg Pro Leu Tyr Ser Arg
475                 480                 485 aga tta cca aaa ggt gta aaa cat ttg aag gat ttt cca att ctg cca    2247
Arg Leu Pro Lys Gly Val Lys His Leu Lys Asp Phe Pro Ile Leu Pro
490                 495                 500                 505 gga gaa ata ttc aaa tat aaa tgg aca gtg act gta gaa gat ggg cca    2295
Gly Glu Ile Phe Lys Tyr Lys Trp Thr Val Thr Val Glu Asp Gly Pro
            510                 515                 520 act aaa tca gat cct cgg tgc ctg acc cgc tat tac tct agt ttc gtt    2343
Thr Lys Ser Asp Pro Arg Cys Leu Thr Arg Tyr Tyr Ser Ser Phe Val
        525                 530                 535 aat atg gag aga gat cta gct tca gga ctc att ggc cct ctc ctc atc    2391
Asn Met Glu Arg Asp Leu Ala Ser Gly Leu Ile Gly Pro Leu Leu Ile
    540                 545                 550 tgc tac aaa gaa tct gta gat caa aga gga aac cag ata atg tca gac    2439
Cys Tyr Lys Glu Ser Val Asp Gln Arg Gly Asn Gln Ile Met Ser Asp
555                 560                 565
```

```
aag agg aat gtc atc ctg ttt tct gta ttt gat gag aac cga agc tgg    2487
Lys Arg Asn Val Ile Leu Phe Ser Val Phe Asp Glu Asn Arg Ser Trp
570                 575                 580                 585 tac ctc aca gag aat ata caa cgc ttt ctc ccc aat cca gct gga gtg    2535
Tyr Leu Thr Glu Asn Ile Gln Arg Phe Leu Pro Asn Pro Ala Gly Val
                590                 595                 600 cag ctt gag gat cca gag ttc caa gcc tcc aac atc atg cac agc atc    2583
Gln Leu Glu Asp Pro Glu Phe Gln Ala Ser Asn Ile Met His Ser Ile
            605                 610                 615 aat ggc tat gtt ttt gat agt ttg cag ttg tca gtt tgt ttg cat gag    2631
Asn Gly Tyr Val Phe Asp Ser Leu Gln Leu Ser Val Cys Leu His Glu
        620                 625                 630 gtg gca tac tgg tac att cta agc att gga gca cag act gac ttc ctt    2679
Val Ala Tyr Trp Tyr Ile Leu Ser Ile Gly Ala Gln Thr Asp Phe Leu
    635                 640                 645 tct gtc ttc ttc tct gga tat acc ttc aaa cac aaa atg gtc tat gaa    2727
Ser Val Phe Phe Ser Gly Tyr Thr Phe Lys His Lys Met Val Tyr Glu
650                 655                 660                 665 gac aca ctc acc cta ttc cca ttc tca gga gaa act gtc ttc atg tcg    2775
Asp Thr Leu Thr Leu Phe Pro Phe Ser Gly Glu Thr Val Phe Met Ser
                670                 675                 680 atg gaa aac cca ggt cta tgg att ctg ggg tgc cac aac tca gac ttt    2823
Met Glu Asn Pro Gly Leu Trp Ile Leu Gly Cys His Asn Ser Asp Phe
            685                 690                 695 cgg aac aga ggc atg acc gcc tta ctg aag gtt tct agt tgt gac aag    2871
Arg Asn Arg Gly Met Thr Ala Leu Leu Lys Val Ser Ser Cys Asp Lys
        700                 705                 710 aac act ggt gat tat tac gag gac agt tat gaa gat att tca gca tac    2919
Asn Thr Gly Asp Tyr Tyr Glu Asp Ser Tyr Glu Asp Ile Ser Ala Tyr
    715                 720                 725 ttg ctg agt aaa aac aat gcc att gaa cca aga agc ttc tcc cag aat    2967
Leu Leu Ser Lys Asn Asn Ala Ile Glu Pro Arg Ser Phe Ser Gln Asn
730                 735                 740                 745 tca aga cat caa gct tat cga tac cgt cga ggg gaa ata act cgt act    3015
Ser Arg His Gln Ala Tyr Arg Tyr Arg Arg Gly Glu Ile Thr Arg Thr
                750                 755                 760 act ctt cag tca gat caa gag gaa att gac tat gat gat acc ata tca    3063
Thr Leu Gln Ser Asp Gln Glu Glu Ile Asp Tyr Asp Asp Thr Ile Ser
            765                 770                 775 gtt gaa atg aag aag gaa gat ttt gac att tat gat gag gat gaa aat    3111
Val Glu Met Lys Lys Glu Asp Phe Asp Ile Tyr Asp Glu Asp Glu Asn
        780                 785                 790 cag agc ccc cgc agc ttt caa aag aaa aca cga cac tat ttt att gct    3159
Gln Ser Pro Arg Ser Phe Gln Lys Lys Thr Arg His Tyr Phe Ile Ala
    795                 800                 805 gca gtg gag agg ctc tgg gat tat ggg atg agt agc tcc cca cat gtt    3207
Ala Val Glu Arg Leu Trp Asp Tyr Gly Met Ser Ser Ser Pro His Val
810                 815                 820                 825 cta aga aac agg gct cag agt ggc agt gtc cct cag ttc aag aaa gtt    3255
Leu Arg Asn Arg Ala Gln Ser Gly Ser Val Pro Gln Phe Lys Lys Val
                830                 835                 840 gtt ttc cag gaa ttt act gat ggc tcc ttt act cag ccc tta tac cgt    3303
Val Phe Gln Glu Phe Thr Asp Gly Ser Phe Thr Gln Pro Leu Tyr Arg
            845                 850                 855 gga gaa cta aat gaa cat ttg gga ctc ctg ggg cca tat ata aga gca    3351
Gly Glu Leu Asn Glu His Leu Gly Leu Leu Gly Pro Tyr Ile Arg Ala
        860                 865                 870 gaa gtt gaa gat aat atc atg gta act ttc aga aat cag gcc tct cgt    3399
Glu Val Glu Asp Asn Ile Met Val Thr Phe Arg Asn Gln Ala Ser Arg
```

```
                875                 880                 885
ccc tat tcc ttc tat tct agc ctt att tct tat gag gaa gat cag agg     3447
Pro Tyr Ser Phe Tyr Ser Ser Leu Ile Ser Tyr Glu Glu Asp Gln Arg
890                 895                 900                 905 caa gga gca gaa cct aga aaa aac ttt gtc aag cct aat gaa acc aaa     3495
Gln Gly Ala Glu Pro Arg Lys Asn Phe Val Lys Pro Asn Glu Thr Lys
            910                 915                 920 act tac ttt tgg aaa gtg caa cat cat atg gca ccc act aaa gat gag     3543
Thr Tyr Phe Trp Lys Val Gln His His Met Ala Pro Thr Lys Asp Glu
                925                 930                 935 ttt gac tgc aaa gcc tgg gct tat ttc tct gat gtt gac ctg gaa aaa     3591
Phe Asp Cys Lys Ala Trp Ala Tyr Phe Ser Asp Val Asp Leu Glu Lys
            940                 945                 950 gat gtg cac tca ggc ctg att gga ccc ctt ctg gtc tgc cac act aac     3639
Asp Val His Ser Gly Leu Ile Gly Pro Leu Leu Val Cys His Thr Asn
                955                 960                 965 aca ctg aac cct gct cat ggg aga caa gtg aca gta cag gaa ttt gct     3687
Thr Leu Asn Pro Ala His Gly Arg Gln Val Thr Val Gln Glu Phe Ala
970                 975                 980                 985 ctg ttt ttc acc atc ttt gat gag acc aaa agc tgg tac ttc act gaa     3735
Leu Phe Phe Thr Ile Phe Asp Glu Thr Lys Ser Trp Tyr Phe Thr Glu
                990                 995                 1000 aat atg gaa aga aac tgc agg gct ccc tgc aat atc cag atg gaa gat     3783
Asn Met Glu Arg Asn Cys Arg Ala Pro Cys Asn Ile Gln Met Glu Asp
                1005                1010                1015 ccc act ttt aaa gag aat tat cgc ttc cat gca atc aat ggc tac ata     3831
Pro Thr Phe Lys Glu Asn Tyr Arg Phe His Ala Ile Asn Gly Tyr Ile
            1020                1025                1030 atg gat aca cta cct ggc tta gta atg gct cag gat caa agg att cga     3879
Met Asp Thr Leu Pro Gly Leu Val Met Ala Gln Asp Gln Arg Ile Arg
            1035                1040                1045 tgg tat ctg ctc agc atg ggc agc aat gaa aac atc cat tct att cat     3927
Trp Tyr Leu Leu Ser Met Gly Ser Asn Glu Asn Ile His Ser Ile His
1050                1055                1060                1065 ttc agt gga cat gtg ttc act gta cga aaa aaa gag gag tat aaa atg     3975
Phe Ser Gly His Val Phe Thr Val Arg Lys Lys Glu Glu Tyr Lys Met
                1070                1075                1080 gca ctg tac aat ctc tat cca ggt gtt ttt gag aca gtg gaa atg tta     4023
Ala Leu Tyr Asn Leu Tyr Pro Gly Val Phe Glu Thr Val Glu Met Leu
            1085                1090                1095 cca tcc aaa gct gga att tgg cgg gtg gaa tgc ctt att ggc gag cat     4071
Pro Ser Lys Ala Gly Ile Trp Arg Val Glu Cys Leu Ile Gly Glu His
            1100                1105                1110 cta cat gct ggg atg agc aca ctt ttt ctg gtg tac agc aat aag tgt     4119
Leu His Ala Gly Met Ser Thr Leu Phe Leu Val Tyr Ser Asn Lys Cys
            1115                1120                1125 cag act ccc ctg gga atg gct tct gga cac att aga gat ttt cag att     4167
Gln Thr Pro Leu Gly Met Ala Ser Gly His Ile Arg Asp Phe Gln Ile
1130                1135                1140                1145 aca gct tca gga caa tat gga cag tgg gcc cca aag ctg gcc aga ctt     4215
Thr Ala Ser Gly Gln Tyr Gly Gln Trp Ala Pro Lys Leu Ala Arg Leu
            1150                1155                1160 cat tat tcc gga tca atc aat gcc tgg agc acc aag gag ccc ttt tct     4263
His Tyr Ser Gly Ser Ile Asn Ala Trp Ser Thr Lys Glu Pro Phe Ser
            1165                1170                1175 tgg atc aag gtg gat ctg ttg gca cca atg att att cac ggc atc aag     4311
Trp Ile Lys Val Asp Leu Leu Ala Pro Met Ile Ile His Gly Ile Lys
            1180                1185                1190 acc cag ggt gcc cgt cag aag ttc tcc agc ctc tac atc tct cag ttt     4359
```

```
                                    -continued

Thr Gln Gly Ala Arg Gln Lys Phe Ser Ser Leu Tyr Ile Ser Gln Phe
    1195                1200                1205 atc atc atg tat agt ctt gat ggg aag aag tgg cag act tat cga gga    4407
Ile Ile Met Tyr Ser Leu Asp Gly Lys Lys Trp Gln Thr Tyr Arg Gly
1210                1215                1220                1225 aat tcc act gga acc tta atg gtc ttc ttt ggc aat gtg gat tca tct    4455
Asn Ser Thr Gly Thr Leu Met Val Phe Phe Gly Asn Val Asp Ser Ser
                1230                1235                1240 ggg ata aaa cac aat att ttt aac cct cca att att gct cga tac atc    4503
Gly Ile Lys His Asn Ile Phe Asn Pro Pro Ile Ile Ala Arg Tyr Ile
            1245                1250                1255 cgt ttg cac cca act cat tat agc att cgc agc act ctt cgc atg gag    4551
Arg Leu His Pro Thr His Tyr Ser Ile Arg Ser Thr Leu Arg Met Glu
        1260                1265                1270 ttg atg ggc tgt gat tta aat agt tgc agc atg cca ttg gga atg gag    4599
Leu Met Gly Cys Asp Leu Asn Ser Cys Ser Met Pro Leu Gly Met Glu
    1275                1280                1285 agt aaa gca ata tca gat gca cag att act gct tca tcc tac ttt acc    4647
Ser Lys Ala Ile Ser Asp Ala Gln Ile Thr Ala Ser Ser Tyr Phe Thr
1290                1295                1300                1305 aat atg ttt gcc acc tgg tct cct tca aaa gct cga ctt cac ctc caa    4695
Asn Met Phe Ala Thr Trp Ser Pro Ser Lys Ala Arg Leu His Leu Gln
                1310                1315                1320 ggg agg agt aat gcc tgg aga cct cag gtg aat aat cca aaa gag tgg    4743
Gly Arg Ser Asn Ala Trp Arg Pro Gln Val Asn Asn Pro Lys Glu Trp
            1325                1330                1335 ctg caa gtg gac ttc cag aag aca atg aaa gtc aca gga gta act act    4791
Leu Gln Val Asp Phe Gln Lys Thr Met Lys Val Thr Gly Val Thr Thr
        1340                1345                1350 cag gga gta aaa tct ctg ctt acc agc atg tat gtg aag gag ttc ctc    4839
Gln Gly Val Lys Ser Leu Leu Thr Ser Met Tyr Val Lys Glu Phe Leu
    1355                1360                1365 atc tcc agc agt caa gat ggc cat cag tgg acc ctc ttt ttt cag aat    4887
Ile Ser Ser Ser Gln Asp Gly His Gln Trp Thr Leu Phe Phe Gln Asn
1370                1375                1380                1385 ggc aaa gta aag gtt ttt cag gga aat caa gac tcc ttc aca cct gtg    4935
Gly Lys Val Lys Val Phe Gln Gly Asn Gln Asp Ser Phe Thr Pro Val
                1390                1395                1400 gtg aac tct cta gac cca ccg tta ctg act cgc tac ctt cga att cac    4983
Val Asn Ser Leu Asp Pro Pro Leu Leu Thr Arg Tyr Leu Arg Ile His
            1405                1410                1415 ccc cag agt tgg gtg cac cag att gcc ctg agg atg gag gtt ctg ggc    5031
Pro Gln Ser Trp Val His Gln Ile Ala Leu Arg Met Glu Val Leu Gly
        1420                1425                1430 tgc gag gca cag gac ctc tac tgagcggccg cgactctact agaggatctt       5082
Cys Glu Ala Gln Asp Leu Tyr
    1435                1440 tgtgaaggaa ccttacttct gtggtgtgac ataattggac aaactaccta cagagattta  5142
aagctctaag gtaaatataa aatttttaag tgtataatgt gttaaactac tgattctaat  5202
tgtttgtgta ttttagattc caacctatgg aactgatgaa tgggagcagt ggtggaatgc  5262
ctttaatgag gaaaacctgt tttgctcaga agaaatgcca tctagtgatg atgaggctac  5322
tgctgactct caacattcta ctcctccaaa aagaagagaa aagtagaag acccaaggaa   5382 cttccttca gaattgctaa gttttttgag tcatgctgtg tttagtaata gaactcttgc   5442
ttgctttgct atttcacca caaaggaaaa agctgcactg ctatacaaga aaattatgga   5502 aaaatattc gtaaccttta taagtaggca taacagttat aatcataaca tactgttttt   5562
```

```
tcttactcca cacaggcata gagtgtctgc tattaataac tatgctcaaa aattgtgtac   5622
ctttagcttt ttaatttgta aaggggttaa taaggaatat ttgatgtata gtgccttgac   5682
tagagatcat aatcagccat accacatttg tagaggtttt acttgcttta aaaaacctcc   5742
cacacctccc cctgaacctg aaacataaaa tgaatgcaat tgttgttgtt aacttgttta   5802
ttgcagctta taatggttac aaataaagca atagcatcac aaatttcaca aataaagcat   5862
tttttccact gcattctagt tgtggtttgt ccaaactcat caatgtatct tatcatgtct   5922 ggatccccg aacgccagca agacgtagcc cagcgcgtcg ccccgagat gcgccgcgtg    5982 cggctgctgg agatggcgga cgcgatggat atgttctgcc aagggttggt ttgcgcattc   6042
acagttctcc gcaagaattg attggctcca attcttggag tggtgaatcc gttagcgagg   6102
tgccgccctg cttcatcccc gtggcccgtt gctcgcgttt gctggcggtg tccccggaag   6162
aaatatattt gcatgtcttt agttctatga tgacacaaac cccgcccagc gtcttgtcat   6222
tggcgaattc gaacacgcag atgcagtcgg ggcggcgcgg tccgaggtcc acttcgcata   6282
ttaaggtgac gcgtgtggcc tcgaacaccg agcgaccctg cagcgacccg cttaacagcg   6342
tcaacagcgt gccgcagatc agcttgatat gaaaaagcct gaactcaccg cgacgtctgt   6402
cgagaagttt ctgatcgaaa agttcgacag cgtctccgac ctgatgcagc tctcggaggg   6462
cgaagaatct cgtgctttca gcttcgatgt aggagggcgt ggatatgtcc tgcgggtaaa   6522
tagctgcgcc gatggtttct acaaagatcg ttatgtttat cggcactttg catcggccgc   6582
gctcccgatt ccggaagtgc ttgacattgg ggaattcagc gagagcctga cctattgcat   6642
ctcccgccgt gcacagggtg tcacgttgca agacctgcct gaaaccgaac tgcccgctgt   6702
tctgcagccg gtcgcggagg ccatggatgc gatcgctgcg gccgatctta gccagacgag   6762
cgggttcggc ccattcggac cgcaaggaat cggtcaatac actacatggc gtgatttcat   6822
atgcgcgatt gctgatcccc atgtgtatca ctggcaaact gtgatggacg acaccgtcag   6882
tgcgtccgtc gcgcaggctc tcgatgagct gatgctttgg gccgaggact gccccgaagt   6942
ccggcacctc gtgcacgcgg atttcggctc caacaatgtc ctgacggaca atggccgcat   7002
aacagcggtc attgactgga gcgaggcgat gttcggggat tcccaatacg aggtcgccaa   7062
catcttcttc tggaggccgt ggttggcttg tatggagcag cagacgcgct acttcgagcg   7122
gaggcatccg gagcttgcag gatcgccgcg gctccgggcg tatatgctcc gcattggtct   7182
tgaccaactc tatcagagct tggttgacgg caatttcgat gatgcagctt gggcgcaggg   7242
tcgatgcgac gcaatcgtcc gatccggagc cgggactgtc gggcgtacac aaatcgcccg   7302
cagaagcgcg gccgtctgga ccgatggctg tgtagaagta ctcgccgata gtggaaaccg   7362
acgccccagc actcgtccgg atcggagat gggggaggct aactgaaaca cggaaggaga   7422
caataccgga aggaacccgc gctatgacgg caataaaaag acagaataaa acgcacgggt   7482
gttgggtcgt ttgttcataa acgcggggtt cggtcccagg ctggcactc tgtcgatacc    7542 ccaccgagac cccattgggg ccaatacgcc cgcgtttctt ccttttcccc accccacccc   7602
ccaagttcgg gtgaaggccc agggctcgca gccaacgtcg gggcggcagg ccctgccata   7662
gccactggcc ccgtgggtta gggacggggt ccccatggg gaatggttta tggttcgtgg    7722
gggttattat tttgggcgtt gcgtgggtc aggtccacga ctggactgag cagacagacc    7782
catggttttt ggatggcctg gcatggacc gcatgtactg gcgcgacacg aacaccgggc    7842
gtctgtggct gccaaacacc cccgacccc aaaaaccacc gcgcggattt ctggcgtgcc    7902
aagctgggta ccctctagag cgaattaatt cactggccgt cgttttacaa cgtcgtgact   7962
```

```
gggaaaaccc tggcgttacc caacttaatc gccttgcagc acatccccct ttcgccagct      8022
ggcataatag cgaagaggcc cgcaccgatc gcccttccca acagttgcgc agcctgaatg      8082
gcgaatggcg cctgatgcgg tattttctcc ttacgcatct gtgcggtatt tcacaccgca      8142
tatggtgcac tctcagtaca atctgctctg atgccgcata gttaagccag ccccgacacc      8202
cgccaacacc cgctgacgcg ccctgacggg cttgtctgct cccggcatcc gcttacagac      8262
aagctgtgac cgtctccggg agctgcatgt gtcagaggtt ttcaccgtca tcaccgaaac      8322
gcgcgagacg aaaggggggg taccagcttc gtagctagaa catcatgttc tgggatatca      8382
gcttcgtagc tagaacatca tgttctggta cccccctcgt gatacgccta ttttttatagg     8442
ttaatgtcat gataataatg gtttcttaga cgtcaggtgg cacttttcgg ggaaatgtgc      8502
gcggaaccc  tatttgttta ttttctaaa  tacattcaaa tatgtatccg ctcatgagac      8562
ataaccctg  ataaatgctt caataatatt gaaaaaggaa gagtatgagt attcaacatt      8622
tccgtgtcgc ccttattccc ttttttgcgg cattttgcct tcctgttttt gctcacccag      8682
aaacgctggt gaaagtaaaa gatgctgaag atcagttggg tgcacgagtg ggttacatcg      8742
aactggatct caacagcggt aagatccttg agagttttcg ccccgaagaa cgttttccaa      8802
tgatgagcac ttttaaagtt ctgctatgtg gcgcggtatt atcccgtatt gacgccgggc      8862
aagagcaact cggtcgccgc atacactatt ctcagaatga cttggttgag tactcaccag      8922
tcacagaaaa gcatcttacg gatggcatga cagtaagaga attatgcagt gctgccataa      8982
ccatgagtga taacactgcg gccaacttac ttctgacaac gatcggagga ccgaaggagc      9042
taaccgcttt tttgcacaac atgggggatc atgtaactcg ccttgatcgt tgggaaccgg      9102
agctgaatga agccatacca aacgacgagc gtgacaccac gatgcctgta gcaatggcaa      9162
caacgttgcg caaactatta actggcgaac tacttactct agcttcccgg caacaattaa      9222
tagactggat ggaggcggat aaagttgcag gaccacttct gcgctcggcc cttccggctg      9282
gctggtttat tgctgataaa tctggagccg gtgagcgtgg gtctcgcggt atcattgcag      9342
cactggggcc agatggtaag ccctcccgta tcgtagttat ctacacgacg gggagtcagg      9402
caactatgga tgaacgaaat agacagatcg ctgagatagg tgcctcactg attaagcatt      9462
ggtaactgtc agaccaagtt tactcatata ctttagat   tgatttaaaa cttcattttt      9522
aatttaaaag gatctaggtg aagatccttt ttgataatct catgaccaaa atcccttaac      9582
gtgagttttc gttccactga gcgtcagacc ccgtagaaaa gatcaaagga tcttcttgag      9642
atcctttttt tctgcgcgta atctgctgct tgcaaacaaa aaaccaccg  ctaccagcgg      9702
tggtttgttt gccggatcaa gagctaccaa ctctttttcc gaaggtaact ggcttcagca      9762
gagcgcagat accaaatact gttcttctag tgtagccgta gttaggccac cacttcaaga      9822
actctgtagc accgcctaca tacctcgctc tgctaatcct gttaccagtg ctgctgccag     9882
gtggcgataa gtcgtgtctt accgggttgg actcaagacg atagttaccg gataaggcgc      9942
agcggtcggg ctgaacgggg ggttcgtgca cacagcccag cttggagcga acgacctaca     10002
ccgaactgag atacctacag cgtgagctat gagaaagcgc cacgcttccc gaagggagaa     10062
aggcggacag gtatccggta agcggcaggg tcggaacagg agagcgcacg agggagcttc     10122
cagggggaaa cgcctggtat ctttatagtc ctgtcgggtt tcgccacctc tgacttgagc     10182
gtcgatttt  gtgatgctcg tcagggggc ggagcctatg gaaaaacgcc agcaacgcgg      10242
ccttttacg  gttcctggcc ttttgctggc cttttgctca catgttcttt cctgcgttat      10302
```

```
cccctgattc tgtggataac cgtattaccg cctttgagtg agctgatacc gctcgccgca    10362
gccgaacgac cgagcgcagc gagtcagtga gcgaggaagc ggaagagcgc ccaatacgca    10422
aaccgcctct ccccgcgcgt tggccgattc attaatgcag ctggcacgac aggtttcccg    10482 actgaaagc gggcagtgag cgcaacgcaa ttaatgtgag ttagctcact cattaggcac    10542
cccaggcttt acactttatg cttccggctc gtatgttgtg tggaattgtg agcggataac    10602
aatttcacac aggaaacagc tatgaccatg attacgccaa gctctctaga gctctagagc    10662
tctagagctc tagagagctt gcatgcctgc aggtcg                              10698
```

<210> SEQ ID NO 13
<211> LENGTH: 1459
<212> TYPE: PRT
<213> ORGANISM: Artificial Sequence
<220> FEATURE:
<223> OTHER INFORMATION: pTGF8-2hyg-s

<400> SEQUENCE: 13

```
Met Gln Ile Glu Leu Ser Thr Cys Phe Phe Leu Cys Leu Leu Arg Phe
             -15                 -10                  -5

Cys Phe Ser Ala Thr Arg Arg Tyr Tyr Leu Gly Ala Val Glu Leu Ser
     -1   1                   5                  10

Trp Asp Tyr Met Gln Ser Asp Leu Gly Glu Leu Pro Val Asp Ala Arg
         15                  20                  25

Phe Pro Pro Arg Val Pro Lys Ser Phe Pro Phe Asn Thr Ser Val Val
 30                  35                  40                  45

Tyr Lys Lys Thr Leu Phe Val Glu Phe Thr Asp His Leu Phe Asn Ile
                 50                  55                  60

Ala Lys Pro Arg Pro Pro Trp Met Gly Leu Leu Gly Pro Thr Ile Gln
             65                  70                  75

Ala Glu Val Tyr Asp Thr Val Val Ile Thr Leu Lys Asn Met Ala Ser
         80                  85                  90

His Pro Val Ser Leu His Ala Val Gly Val Ser Tyr Trp Lys Ala Ser
     95                 100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                130                 135                 140

Lys Glu Asn Gly Pro Met Ala Ser Asp Pro Leu Cys Leu Thr Tyr Ser
            145                 150                 155

Tyr Leu Ser His Val Asp Leu Val Lys Asp Leu Asn Ser Gly Leu Ile
        160                 165                 170

Gly Ala Leu Leu Val Cys Arg Glu Gly Ser Leu Ala Lys Glu Lys Thr
    175                 180                 185

Gln Thr Leu His Lys Phe Ile Leu Leu Phe Ala Val Phe Asp Glu Gly
190                 195                 200                 205

Lys Ser Trp His Ser Glu Thr Lys Asn Ser Leu Met Gln Asp Arg Asp
                210                 215                 220

Ala Ala Ser Ala Arg Ala Trp Pro Lys Met His Thr Val Asn Gly Tyr
            225                 230                 235

Val Asn Arg Ser Leu Pro Gly Leu Ile Gly Cys His Arg Lys Ser Val
        240                 245                 250

Tyr Trp His Val Ile Gly Met Gly Thr Thr Pro Glu Val His Ser Ile
    255                 260                 265

Phe Leu Glu Gly His Thr Phe Leu Val Arg Asn His Arg Gln Ala Ser
```

-continued

```
                270                 275                 280                 285
Leu Glu Ile Ser Pro Ile Thr Phe Leu Thr Ala Gln Thr Leu Leu Met
                290                 295                 300
Asp Leu Gly Gln Phe Leu Leu Phe Cys His Ile Ser Ser His Gln His
                305                 310                 315
Asp Gly Met Glu Ala Tyr Val Lys Val Asp Ser Cys Pro Glu Glu Pro
                320                 325                 330
Gln Leu Arg Met Lys Asn Asn Glu Glu Ala Glu Asp Tyr Asp Asp Asp
                335                 340                 345
Leu Thr Asp Ser Glu Met Asp Val Val Arg Phe Asp Asp Asn Ser
350                 355                 360                 365
Pro Ser Phe Ile Gln Ile Arg Ser Val Ala Lys Lys His Pro Lys Thr
                370                 375                 380
Trp Val His Tyr Ile Ala Ala Glu Glu Asp Trp Asp Tyr Ala Pro
                385                 390                 395
Leu Val Leu Ala Pro Asp Asp Arg Ser Tyr Lys Ser Gln Tyr Leu Asn
                400                 405                 410
Asn Gly Pro Gln Arg Ile Gly Arg Lys Tyr Lys Lys Val Arg Phe Met
                415                 420                 425
Ala Tyr Thr Asp Glu Thr Phe Lys Thr Arg Glu Ala Ile Gln His Glu
430                 435                 440                 445
Ser Gly Ile Leu Gly Pro Leu Leu Tyr Gly Glu Val Gly Asp Thr Leu
                450                 455                 460
Leu Ile Ile Phe Lys Asn Gln Ala Ser Arg Pro Tyr Asn Ile Tyr Pro
                465                 470                 475
His Gly Ile Thr Asp Val Arg Pro Leu Tyr Ser Arg Arg Leu Pro Lys
                480                 485                 490
Gly Val Lys His Leu Lys Asp Phe Pro Ile Leu Pro Gly Glu Ile Phe
                495                 500                 505
Lys Tyr Lys Trp Thr Val Thr Val Glu Asp Gly Pro Thr Lys Ser Asp
510                 515                 520                 525
Pro Arg Cys Leu Thr Arg Tyr Tyr Ser Ser Phe Val Asn Met Glu Arg
                530                 535                 540
Asp Leu Ala Ser Gly Leu Ile Gly Pro Leu Leu Ile Cys Tyr Lys Glu
                545                 550                 555
Ser Val Asp Gln Arg Gly Asn Gln Ile Met Ser Asp Lys Arg Asn Val
                560                 565                 570
Ile Leu Phe Ser Val Phe Asp Glu Asn Arg Ser Trp Tyr Leu Thr Glu
575                 580                 585
Asn Ile Gln Arg Phe Leu Pro Asn Pro Ala Gly Val Gln Leu Glu Asp
590                 595                 600                 605
Pro Glu Phe Gln Ala Ser Asn Ile Met His Ser Ile Asn Gly Tyr Val
                610                 615                 620
Phe Asp Ser Leu Gln Leu Ser Val Cys Leu His Glu Val Ala Tyr Trp
                625                 630                 635
Tyr Ile Leu Ser Ile Gly Ala Gln Thr Asp Phe Leu Ser Val Phe Phe
                640                 645                 650
Ser Gly Tyr Thr Phe Lys His Lys Met Val Tyr Glu Asp Thr Leu Thr
                655                 660                 665
Leu Phe Pro Phe Ser Gly Glu Thr Val Phe Met Ser Met Glu Asn Pro
670                 675                 680                 685
Gly Leu Trp Ile Leu Gly Cys His Asn Ser Asp Phe Arg Asn Arg Gly
                690                 695                 700
```

-continued

```
Met Thr Ala Leu Leu Lys Val Ser Ser Cys Asp Lys Asn Thr Gly Asp
        705                 710                 715

Tyr Tyr Glu Asp Ser Tyr Glu Asp Ile Ser Ala Tyr Leu Leu Ser Lys
        720                 725                 730

Asn Asn Ala Ile Glu Pro Arg Ser Phe Ser Gln Asn Ser Arg His Gln
735                 740                 745

Ala Tyr Arg Tyr Arg Arg Gly Glu Ile Thr Arg Thr Thr Leu Gln Ser
750                 755                 760                 765

Asp Gln Glu Glu Ile Asp Tyr Asp Asp Thr Ile Ser Val Glu Met Lys
                770                 775                 780

Lys Glu Asp Phe Asp Ile Tyr Asp Glu Asp Glu Asn Gln Ser Pro Arg
            785                 790                 795

Ser Phe Gln Lys Lys Thr Arg His Tyr Phe Ile Ala Ala Val Glu Arg
        800                 805                 810

Leu Trp Asp Tyr Gly Met Ser Ser Ser Pro His Val Leu Arg Asn Arg
        815                 820                 825

Ala Gln Ser Gly Ser Val Pro Gln Phe Lys Lys Val Val Phe Gln Glu
830                 835                 840                 845

Phe Thr Asp Gly Ser Phe Thr Gln Pro Leu Tyr Arg Gly Glu Leu Asn
                850                 855                 860

Glu His Leu Gly Leu Leu Gly Pro Tyr Ile Arg Ala Glu Val Glu Asp
            865                 870                 875

Asn Ile Met Val Thr Phe Arg Asn Gln Ala Ser Arg Pro Tyr Ser Phe
        880                 885                 890

Tyr Ser Ser Leu Ile Ser Tyr Glu Glu Asp Gln Arg Gln Gly Ala Glu
        895                 900                 905

Pro Arg Lys Asn Phe Val Lys Pro Asn Glu Thr Lys Thr Tyr Phe Trp
910                 915                 920                 925

Lys Val Gln His His Met Ala Pro Thr Lys Asp Glu Phe Asp Cys Lys
                930                 935                 940

Ala Trp Ala Tyr Phe Ser Asp Val Asp Leu Glu Lys Asp Val His Ser
            945                 950                 955

Gly Leu Ile Gly Pro Leu Leu Val Cys His Thr Asn Thr Leu Asn Pro
        960                 965                 970

Ala His Gly Arg Gln Val Thr Val Gln Glu Phe Ala Leu Phe Phe Thr
        975                 980                 985

Ile Phe Asp Glu Thr Lys Ser Trp Tyr Phe Thr Glu Asn Met Glu Arg
990                 995                 1000                1005

Asn Cys Arg Ala Pro Cys Asn Ile Gln Met Glu Asp Pro Thr Phe Lys
                1010                1015                1020

Glu Asn Tyr Arg Phe His Ala Ile Asn Gly Tyr Ile Met Asp Thr Leu
            1025                1030                1035

Pro Gly Leu Val Met Ala Gln Asp Gln Arg Ile Arg Trp Tyr Leu Leu
        1040                1045                1050

Ser Met Gly Ser Asn Glu Asn Ile His Ser Ile His Phe Ser Gly His
        1055                1060                1065

Val Phe Thr Val Arg Lys Lys Glu Glu Tyr Lys Met Ala Leu Tyr Asn
1070                1075                1080                1085

Leu Tyr Pro Gly Val Phe Glu Thr Val Glu Met Leu Pro Ser Lys Ala
                1090                1095                1100

Gly Ile Trp Arg Val Glu Cys Leu Ile Gly Glu His Leu His Ala Gly
            1105                1110                1115
```

Met Ser Thr Leu Phe Leu Val Tyr Ser Asn Lys Cys Gln Thr Pro Leu
    1120                1125                1130

Gly Met Ala Ser Gly His Ile Arg Asp Phe Gln Ile Thr Ala Ser Gly
    1135                1140                1145

Gln Tyr Gly Gln Trp Ala Pro Lys Leu Ala Arg Leu His Tyr Ser Gly
1150                1155                1160                1165

Ser Ile Asn Ala Trp Ser Thr Lys Glu Pro Phe Ser Trp Ile Lys Val
            1170                1175                1180

Asp Leu Leu Ala Pro Met Ile Ile His Gly Ile Lys Thr Gln Gly Ala
            1185                1190                1195

Arg Gln Lys Phe Ser Ser Leu Tyr Ile Ser Gln Phe Ile Ile Met Tyr
    1200                1205                1210

Ser Leu Asp Gly Lys Lys Trp Gln Thr Tyr Arg Gly Asn Ser Thr Gly
    1215                1220                1225

Thr Leu Met Val Phe Phe Gly Asn Val Asp Ser Ser Gly Ile Lys His
1230                1235                1240                1245

Asn Ile Phe Asn Pro Pro Ile Ile Ala Arg Tyr Ile Arg Leu His Pro
            1250                1255                1260

Thr His Tyr Ser Ile Arg Ser Thr Leu Arg Met Glu Leu Met Gly Cys
    1265                1270                1275

Asp Leu Asn Ser Cys Ser Met Pro Leu Gly Met Glu Ser Lys Ala Ile
    1280                1285                1290

Ser Asp Ala Gln Ile Thr Ala Ser Ser Tyr Phe Thr Asn Met Phe Ala
    1295                1300                1305

Thr Trp Ser Pro Ser Lys Ala Arg Leu His Leu Gln Gly Arg Ser Asn
1310                1315                1320                1325

Ala Trp Arg Pro Gln Val Asn Asn Pro Lys Glu Trp Leu Gln Val Asp
            1330                1335                1340

Phe Gln Lys Thr Met Lys Val Thr Gly Val Thr Thr Gln Gly Val Lys
    1345                1350                1355

Ser Leu Leu Thr Ser Met Tyr Val Lys Glu Phe Leu Ile Ser Ser Ser
    1360                1365                1370

Gln Asp Gly His Gln Trp Thr Leu Phe Phe Gln Asn Gly Lys Val Lys
    1375                1380                1385

Val Phe Gln Gly Asn Gln Asp Ser Phe Thr Pro Val Val Asn Ser Leu
1390                1395                1400                1405

Asp Pro Pro Leu Leu Thr Arg Tyr Leu Arg Ile His Pro Gln Ser Trp
            1410                1415                1420

Val His Gln Ile Ala Leu Arg Met Glu Val Leu Gly Cys Glu Ala Gln
    1425                1430                1435

Asp Leu Tyr
    1440

<210> SEQ ID NO 14
<211> LENGTH: 10698
<212> TYPE: DNA
<213> ORGANISM: Artificial Sequence
<220> FEATURE:
<223> OTHER INFORMATION: pTGF8-3
<220> FEATURE:
<221> NAME/KEY: CDS
<222> LOCATION: (676)..(5052)
<220> FEATURE:
<221> NAME/KEY: mat_peptide
<222> LOCATION: (733)..(5052)

<400> SEQUENCE: 14

-continued

```
cgcgttgaca ttgattattg actagttatt aatagtaatc aattacgggg tcattagttc      60
atagcccata tatggagttc cgcgttacat aacttacggt aaatggcccg cctggctgac     120
cgcccaacga cccccgccca ttgacgtcaa taatgacgta tgttcccata gtaacgccaa     180
tagggacttt ccattgacgt caatgggtgg agtatttacg gtaaactgcc cacttggcag     240
tacatcaagt gtatcatatg ccaagtacgc cccctattga cgtcaatgac ggtaaatggc     300
ccgcctggca ttatgcccag tacatgacct tatgggactt tcctacttgg cagtacatct     360
acgtattagt catcgctatt accatggtga tgcggttttg gcagtacatc aatgggcgtg     420
gatagcggtt tgactcacgg ggatttccaa gtctccaccc cattgacgtc aatgggagtt     480
tgttttggca ccaaaatcaa cgggactttc caaaatgtcg taacaactcc gccccattga     540
cgcaaatggg cggtaggcgt gtacggtggg aggtctatat aagcagagct ctctggctaa     600
ctagagaacc cactgcttac tggcttatcg aaattaatac gactcactat agggagaccc     660
```
aagcttgacc tcgag atg caa ata gag ctc tcc acc tgc ttc ttt ctg tgc     711
                  Met Gln Ile Glu Leu Ser Thr Cys Phe Phe Leu Cys
                                -15                      -10 ctt ttg cga ttc tgc ttt agt gcc acc aga aga tac tac ctg ggt gca     759
Leu Leu Arg Phe Cys Phe Ser Ala Thr Arg Arg Tyr Tyr Leu Gly Ala
        -5              -1   1                   5 gtg gaa ctg tca tgg gac tat atg caa agt gat ctc ggt gag ctg cct     807
Val Glu Leu Ser Trp Asp Tyr Met Gln Ser Asp Leu Gly Glu Leu Pro
 10              15                  20                      25 gtg gac gca aga ttt cct cct aga gtg cca aaa tct ttt cca ttc aac     855
Val Asp Ala Arg Phe Pro Pro Arg Val Pro Lys Ser Phe Pro Phe Asn
             30                  35                  40 acc tca gtc gtg tac aaa aag act ctg ttt gta gaa ttc acg gat cac     903
Thr Ser Val Val Tyr Lys Lys Thr Leu Phe Val Glu Phe Thr Asp His
                 45                  50                  55 ctt ttc aac atc gct aag cca agg cca ccc tgg atg ggt ctg cta ggt     951
Leu Phe Asn Ile Ala Lys Pro Arg Pro Pro Trp Met Gly Leu Leu Gly
             60                  65                  70 cct acc atc cag gct gag gtt tat gat aca gtg gtc att aca ctt aag     999
Pro Thr Ile Gln Ala Glu Val Tyr Asp Thr Val Val Ile Thr Leu Lys
 75                  80                  85 aac atg gct tcc cat cct gtc agt ctt cat gct gtt ggt gta tcc tac    1047
Asn Met Ala Ser His Pro Val Ser Leu His Ala Val Gly Val Ser Tyr
 90                  95                 100                 105 tgg aaa gct tct gag gga gct gaa tat gat gat cag acc agt caa agg    1095
Trp Lys Ala Ser Glu Gly Ala Glu Tyr Asp Asp Gln Thr Ser Gln Arg
                110                 115                 120 gag aaa gaa gat gat aaa gtc ttc cct ggt gga agc cat aca tat gtc    1143
Glu Lys Glu Asp Asp Lys Val Phe Pro Gly Gly Ser His Thr Tyr Val
                125                 130                 135 tgg cag gtc ctg aaa gag aat ggt cca atg gcc tct gac cca ctg tgc    1191
Trp Gln Val Leu Lys Glu Asn Gly Pro Met Ala Ser Asp Pro Leu Cys
            140                 145                 150 ctt acc tac tca tat ctt tct cat gcg gac ctg gta aaa gac ttg aat    1239
Leu Thr Tyr Ser Tyr Leu Ser His Ala Asp Leu Val Lys Asp Leu Asn
    155                 160                 165 tca ggc ctc att gga gcc cta cta gta tgt aga gaa ggg agt ctg gcc    1287
Ser Gly Leu Ile Gly Ala Leu Leu Val Cys Arg Glu Gly Ser Leu Ala
170                 175                 180                 185 aag gaa aag aca cag acc ttg cac aaa ttt ata cta ctt ttt gct gta    1335
Lys Glu Lys Thr Gln Thr Leu His Lys Phe Ile Leu Leu Phe Ala Val
                190                 195                 200 ttt gat gaa ggg aaa agt tgg cac tca gaa aca aag aac tcc ttg atg    1383
Phe Asp Glu Gly Lys Ser Trp His Ser Glu Thr Lys Asn Ser Leu Met

```
                Phe Asp Glu Gly Lys Ser Trp His Ser Glu Thr Lys Asn Ser Leu Met
                                205                 210                 215 cag gat agg gat gct gca tct gct cgg gcc tgg cct aaa atg cac aca          1431
Gln Asp Arg Asp Ala Ala Ser Ala Arg Ala Trp Pro Lys Met His Thr
            220                 225                 230 gtc aat ggt tat gta aac agg tct ctg cca ggt ctg att gga tgc cac          1479
Val Asn Gly Tyr Val Asn Arg Ser Leu Pro Gly Leu Ile Gly Cys His
    235                 240                 245 agg aaa tca gtc tat tgg cat gtg att gga atg ggc acc act cct gaa          1527
Arg Lys Ser Val Tyr Trp His Val Ile Gly Met Gly Thr Thr Pro Glu
250                 255                 260                 265 gtg cac tca ata ttc ctc gaa ggt cac aca ttt ctt gtg agg aac cat          1575
Val His Ser Ile Phe Leu Glu Gly His Thr Phe Leu Val Arg Asn His
                270                 275                 280 cgc cag gcg tcc ttg gaa atc tcg cca ata act ttc ctt act gct caa          1623
Arg Gln Ala Ser Leu Glu Ile Ser Pro Ile Thr Phe Leu Thr Ala Gln
            285                 290                 295 aca ctc ttg atg gac ctt gga cag ttt cta ctg ttt tgt cat atc tct          1671
Thr Leu Leu Met Asp Leu Gly Gln Phe Leu Leu Phe Cys His Ile Ser
        300                 305                 310 tcc cac caa cat gat ggc atg gaa gct tat gtc aaa gta gac agc tgt          1719
Ser His Gln His Asp Gly Met Glu Ala Tyr Val Lys Val Asp Ser Cys
315                 320                 325 cca gag gaa ccc caa cta cga atg aaa aat aat gaa gaa gcg gaa gac          1767
Pro Glu Glu Pro Gln Leu Arg Met Lys Asn Asn Glu Glu Ala Glu Asp
330                 335                 340                 345 tat gat gat gat ctt act gat tct gaa atg gat gtg gtc agg ttt gat          1815
Tyr Asp Asp Asp Leu Thr Asp Ser Glu Met Asp Val Val Arg Phe Asp
                350                 355                 360 gat gac aac tct cct tcc ttt atc caa att cgc tca gtt gcc aag aag          1863
Asp Asp Asn Ser Pro Ser Phe Ile Gln Ile Arg Ser Val Ala Lys Lys
            365                 370                 375 cat cct aaa act tgg gta cat tac att gct gct gaa gag gag gac tgg          1911
His Pro Lys Thr Trp Val His Tyr Ile Ala Ala Glu Glu Glu Asp Trp
        380                 385                 390 gac tat gct ccc tta gtc ctc gcc ccc gat gac aga agt tat aaa agt          1959
Asp Tyr Ala Pro Leu Val Leu Ala Pro Asp Asp Arg Ser Tyr Lys Ser
395                 400                 405 caa tat ttg aac aat ggc cct cag cgg att ggt agg aag tac aaa aaa          2007
Gln Tyr Leu Asn Asn Gly Pro Gln Arg Ile Gly Arg Lys Tyr Lys Lys
410                 415                 420                 425 gtc cga ttt atg gca tac aca gat gaa acc ttt aag act cgt gaa gct          2055
Val Arg Phe Met Ala Tyr Thr Asp Glu Thr Phe Lys Thr Arg Glu Ala
                430                 435                 440 att cag cat gaa tca gga atc ttg gga cct tta ctt tat ggg gaa gtt          2103
Ile Gln His Glu Ser Gly Ile Leu Gly Pro Leu Leu Tyr Gly Glu Val
            445                 450                 455 gga gac aca ctg ttg att ata ttt aag aat caa gca agc aga cca tat          2151
Gly Asp Thr Leu Leu Ile Ile Phe Lys Asn Gln Ala Ser Arg Pro Tyr
        460                 465                 470 aac atc tac cct cac gga atc act gat gtc cgt cct ttg tat tca agg          2199
Asn Ile Tyr Pro His Gly Ile Thr Asp Val Arg Pro Leu Tyr Ser Arg
475                 480                 485 aga tta cca aaa ggt gta aaa cat ttg aag gat ttt cca att ctg cca          2247
Arg Leu Pro Lys Gly Val Lys His Leu Lys Asp Phe Pro Ile Leu Pro
490                 495                 500                 505 gga gaa ata ttc aaa tat aaa tgg aca gtg act gta gaa gat ggg cca          2295
Gly Glu Ile Phe Lys Tyr Lys Trp Thr Val Thr Val Glu Asp Gly Pro
                510                 515                 520
```

```
act aaa tca gat cct cgg tgc ctg acc cgc tat tac tct agt ttc gtt    2343
Thr Lys Ser Asp Pro Arg Cys Leu Thr Arg Tyr Tyr Ser Ser Phe Val
        525                 530                 535 aat atg gag aga gat cta gct tca gga ctc att ggc cct ctc ctc atc    2391
Asn Met Glu Arg Asp Leu Ala Ser Gly Leu Ile Gly Pro Leu Leu Ile
540                 545                 550 tgc tac aaa gaa tct gta gat caa aga gga aac cag ata atg tca gac    2439
Cys Tyr Lys Glu Ser Val Asp Gln Arg Gly Asn Gln Ile Met Ser Asp
555                 560                 565 aag agg aat gtc atc ctg ttt tct gta ttt gat gag aac cga agc tgg    2487
Lys Arg Asn Val Ile Leu Phe Ser Val Phe Asp Glu Asn Arg Ser Trp
570                 575                 580                 585 tac ctc aca gag aat ata caa cgc ttt ctc ccc aat cca gct gga gtg    2535
Tyr Leu Thr Glu Asn Ile Gln Arg Phe Leu Pro Asn Pro Ala Gly Val
                590                 595                 600 cag ctt gag gat cca gag ttc caa gcc tcc aac atc atg cac agc atc    2583
Gln Leu Glu Asp Pro Glu Phe Gln Ala Ser Asn Ile Met His Ser Ile
            605                 610                 615 aat ggc tat gtt ttt gat agt ttg cag ttg tca gtt tgt ttg cat gag    2631
Asn Gly Tyr Val Phe Asp Ser Leu Gln Leu Ser Val Cys Leu His Glu
        620                 625                 630 gtg gca tac tgg tac att cta agc att gga gca cag act gac ttc ctt    2679
Val Ala Tyr Trp Tyr Ile Leu Ser Ile Gly Ala Gln Thr Asp Phe Leu
    635                 640                 645 tct gtc ttc ttc tct gga tat acc ttc aaa cac aaa atg gtc tat gaa    2727
Ser Val Phe Phe Ser Gly Tyr Thr Phe Lys His Lys Met Val Tyr Glu
650                 655                 660                 665 gac aca ctc acc cta ttc cca ttc tca gga gaa act gtc ttc atg tcg    2775
Asp Thr Leu Thr Leu Phe Pro Phe Ser Gly Glu Thr Val Phe Met Ser
                670                 675                 680 atg gaa aac cca ggt cta tgg att ctg ggg tgc cac aac tca gac ttt    2823
Met Glu Asn Pro Gly Leu Trp Ile Leu Gly Cys His Asn Ser Asp Phe
            685                 690                 695 cgg aac aga ggc atg acc gcc tta ctg aag gtt tct agt tgt gac aag    2871
Arg Asn Arg Gly Met Thr Ala Leu Leu Lys Val Ser Ser Cys Asp Lys
        700                 705                 710 aac act ggt gat tat tac gag gac agt tat gaa gat att tca gca tac    2919
Asn Thr Gly Asp Tyr Tyr Glu Asp Ser Tyr Glu Asp Ile Ser Ala Tyr
    715                 720                 725 ttg ctg agt aaa aac aat gcc att gaa cca aga agc ttc tcc cag aat    2967
Leu Leu Ser Lys Asn Asn Ala Ile Glu Pro Arg Ser Phe Ser Gln Asn
730                 735                 740                 745 tca aga cat caa gct tat cga tac cgt cga ggg gaa ata act cgt act    3015
Ser Arg His Gln Ala Tyr Arg Tyr Arg Arg Gly Glu Ile Thr Arg Thr
                750                 755                 760 act ctt cag tca gat caa gag gaa att gac tat gat gat acc ata tca    3063
Thr Leu Gln Ser Asp Gln Glu Glu Ile Asp Tyr Asp Asp Thr Ile Ser
            765                 770                 775 gtt gaa atg aag aag gaa gat ttt gac att tat gat gag gat gaa aat    3111
Val Glu Met Lys Lys Glu Asp Phe Asp Ile Tyr Asp Glu Asp Glu Asn
        780                 785                 790 cag agc ccc cgc agc ttt caa aag aaa aca cga cac tat ttt att gct    3159
Gln Ser Pro Arg Ser Phe Gln Lys Lys Thr Arg His Tyr Phe Ile Ala
    795                 800                 805 gca gtg gag agg ctc tgg gat tat ggg atg agt agc tcc cca cat gtt    3207
Ala Val Glu Arg Leu Trp Asp Tyr Gly Met Ser Ser Ser Pro His Val
810                 815                 820                 825 cta aga aac agg gct cag agt ggc agt gtc cct cag ttc aag aaa gtt    3255
Leu Arg Asn Arg Ala Gln Ser Gly Ser Val Pro Gln Phe Lys Lys Val
                830                 835                 840
```

```
gtt ttc cag gaa ttt act gat ggc tcc ttt act cag ccc tta tac cgt      3303
Val Phe Gln Glu Phe Thr Asp Gly Ser Phe Thr Gln Pro Leu Tyr Arg
            845                 850                 855 gga gaa cta aat gaa cat ttg gga ctc ctg ggg cca tat ata aga gca      3351
Gly Glu Leu Asn Glu His Leu Gly Leu Leu Gly Pro Tyr Ile Arg Ala
        860                 865                 870 gaa gtt gaa gat aat atc atg gta act ttc aga aat cag gcc tct cgt      3399
Glu Val Glu Asp Asn Ile Met Val Thr Phe Arg Asn Gln Ala Ser Arg
    875                 880                 885 ccc tat tcc ttc tat tct agc ctt att tct tat gag gaa gat cag agg      3447
Pro Tyr Ser Phe Tyr Ser Ser Leu Ile Ser Tyr Glu Glu Asp Gln Arg
890                 895                 900                 905 caa gga gca gaa cct aga aaa aac ttt gtc aag cct aat gaa acc aaa      3495
Gln Gly Ala Glu Pro Arg Lys Asn Phe Val Lys Pro Asn Glu Thr Lys
                910                 915                 920 act tac ttt tgg aaa gtg caa cat cat atg gca ccc act aaa gat gag      3543
Thr Tyr Phe Trp Lys Val Gln His His Met Ala Pro Thr Lys Asp Glu
            925                 930                 935 ttt gac tgc aaa gcc tgg gct tat ttc tct gat gtt gac ctg gaa aaa      3591
Phe Asp Cys Lys Ala Trp Ala Tyr Phe Ser Asp Val Asp Leu Glu Lys
        940                 945                 950 gat gtg cac tca ggc ctg att gga ccc ctt ctg gtc tgc cac act aac      3639
Asp Val His Ser Gly Leu Ile Gly Pro Leu Leu Val Cys His Thr Asn
    955                 960                 965 aca ctg aac cct gct cat ggg aga caa gtg aca gta cag gaa ttt gct      3687
Thr Leu Asn Pro Ala His Gly Arg Gln Val Thr Val Gln Glu Phe Ala
970                 975                 980                 985 ctg ttt ttc acc atc ttt gat gag acc aaa agc tgg tac ttc act gaa      3735
Leu Phe Phe Thr Ile Phe Asp Glu Thr Lys Ser Trp Tyr Phe Thr Glu
                990                 995                 1000 aat atg gaa aga aac tgc agg gct ccc tgc aat atc cag atg gaa gat      3783
Asn Met Glu Arg Asn Cys Arg Ala Pro Cys Asn Ile Gln Met Glu Asp
            1005                1010                1015 ccc act ttt aaa gag aat tat cgc ttc cat gca atc aat ggc tac ata      3831
Pro Thr Phe Lys Glu Asn Tyr Arg Phe His Ala Ile Asn Gly Tyr Ile
        1020                1025                1030 atg gat aca cta cct ggc tta gta atg gct cag gat caa agg att cga      3879
Met Asp Thr Leu Pro Gly Leu Val Met Ala Gln Asp Gln Arg Ile Arg
    1035                1040                1045 tgg tat ctg ctc agc atg ggc agc aat gaa aac atc cat tct att cat      3927
Trp Tyr Leu Leu Ser Met Gly Ser Asn Glu Asn Ile His Ser Ile His
1050                1055                1060                1065 ttc agt gga cat gtg ttc act gta cga aaa aaa gag gag tat aaa atg      3975
Phe Ser Gly His Val Phe Thr Val Arg Lys Lys Glu Glu Tyr Lys Met
                1070                1075                1080 gca ctg tac aat ctc tat cca ggt gtt ttt gag aca gtg gaa atg tta      4023
Ala Leu Tyr Asn Leu Tyr Pro Gly Val Phe Glu Thr Val Glu Met Leu
            1085                1090                1095 cca tcc aaa gct gga att tgg cgg gtg gaa tgc ctt att ggc gag cat      4071
Pro Ser Lys Ala Gly Ile Trp Arg Val Glu Cys Leu Ile Gly Glu His
        1100                1105                1110 cta cat gct ggg atg agc aca ctt ttt ctg gtg tac agc aat aag tgt      4119
Leu His Ala Gly Met Ser Thr Leu Phe Leu Val Tyr Ser Asn Lys Cys
    1115                1120                1125 cag act ccc ctg gga atg gct tct gga cac att aga gat ttt cag att      4167
Gln Thr Pro Leu Gly Met Ala Ser Gly His Ile Arg Asp Phe Gln Ile
1130                1135                1140                1145 aca gct tca gga caa tat gga cag tgg gcc cca aag ctg gcc aga ctt      4215
Thr Ala Ser Gly Gln Tyr Gly Gln Trp Ala Pro Lys Leu Ala Arg Leu
```

-continued

```
                       1150                      1155                      1160
cat tat tcc gga tca atc aat gcc tgg agc acc aag gag ccc ttt tct           4263
His Tyr Ser Gly Ser Ile Asn Ala Trp Ser Thr Lys Glu Pro Phe Ser
            1165                      1170                      1175 tgg atc aag gtg gat ctg ttg gca cca atg att att cac ggc atc aag           4311
Trp Ile Lys Val Asp Leu Leu Ala Pro Met Ile Ile His Gly Ile Lys
            1180                      1185                      1190 acc cag ggt gcc cgt cag aag ttc tcc agc ctc tac atc tct cag ttt           4359
Thr Gln Gly Ala Arg Gln Lys Phe Ser Ser Leu Tyr Ile Ser Gln Phe
            1195                      1200                      1205 atc atc atg tat agt ctt gat ggg aag aag tgg cag act tat cga gga           4407
Ile Ile Met Tyr Ser Leu Asp Gly Lys Lys Trp Gln Thr Tyr Arg Gly
1210                      1215                      1220                      1225 aat tcc act gga acc tta atg gtc ttc ttt ggc aat gtg gat tca tct           4455
Asn Ser Thr Gly Thr Leu Met Val Phe Phe Gly Asn Val Asp Ser Ser
                        1230                      1235                      1240 ggg ata aaa cac aat att ttt aac cct cca att att gct cga tac atc           4503
Gly Ile Lys His Asn Ile Phe Asn Pro Pro Ile Ile Ala Arg Tyr Ile
            1245                      1250                      1255 cgt ttg cac cca act cat tat agc att cgc agc act ctt cgc atg gag           4551
Arg Leu His Pro Thr His Tyr Ser Ile Arg Ser Thr Leu Arg Met Glu
            1260                      1265                      1270 ttg atg ggc tgt gat tta aat agt tgc agc atg cca ttg gga atg gag           4599
Leu Met Gly Cys Asp Leu Asn Ser Cys Ser Met Pro Leu Gly Met Glu
            1275                      1280                      1285 agt aaa gca ata tca gat gca cag att act gct tca tcc tac ttt acc           4647
Ser Lys Ala Ile Ser Asp Ala Gln Ile Thr Ala Ser Ser Tyr Phe Thr
1290                      1295                      1300                      1305 aat atg ttt gcc acc tgg tct cct tca aaa gct cga ctt cac ctc caa           4695
Asn Met Phe Ala Thr Trp Ser Pro Ser Lys Ala Arg Leu His Leu Gln
                        1310                      1315                      1320 ggg agg agt aat gcc tgg aga cct cag gag aat aat cca aaa gag tgg           4743
Gly Arg Ser Asn Ala Trp Arg Pro Gln Glu Asn Asn Pro Lys Glu Trp
            1325                      1330                      1335 ctg caa gtg gac ttc cag aag aca atg aaa gtc aca gga gta act act           4791
Leu Gln Val Asp Phe Gln Lys Thr Met Lys Val Thr Gly Val Thr Thr
            1340                      1345                      1350 cag gga gta aaa tct ctg ctt acc agc atg tat gtg aag gag ttc ctc           4839
Gln Gly Val Lys Ser Leu Leu Thr Ser Met Tyr Val Lys Glu Phe Leu
            1355                      1360                      1365 atc tcc agc agt caa gat ggc cat cag tgg acc ctc ttt ttt cag aat           4887
Ile Ser Ser Ser Gln Asp Gly His Gln Trp Thr Leu Phe Phe Gln Asn
1370                      1375                      1380                      1385 ggc aaa gta aag gtt ttt cag gga aat caa gac tcc ttc aca cct gtg           4935
Gly Lys Val Lys Val Phe Gln Gly Asn Gln Asp Ser Phe Thr Pro Val
                        1390                      1395                      1400 gtg aac tct cta gac cca ccg tta ctg act cgc tac ctt cga att cac           4983
Val Asn Ser Leu Asp Pro Pro Leu Leu Thr Arg Tyr Leu Arg Ile His
            1405                      1410                      1415 ccc cag agt tgg gtg cac cag att gcc ctg agg atg gag gtt ctg ggc           5031
Pro Gln Ser Trp Val His Gln Ile Ala Leu Arg Met Glu Val Leu Gly
            1420                      1425                      1430 tgc gag gca cag gac ctc tac tgagcggccg cgactctact agaggatctt              5082
Cys Glu Ala Gln Asp Leu Tyr
            1435                      1440 tgtgaaggaa ccttacttct gtggtgtgac ataattggac aaactaccta cagagattta        5142
aagctctaag gtaaatataa aatttttaag tgtataatgt gttaaactac tgattctaat        5202
tgtttgtgta ttttagattc caacctatgg aactgatgaa tgggagcagt ggtggaatgc        5262
```

```
ctttaatgag gaaaacctgt tttgctcaga agaaatgcca tctagtgatg atgaggctac    5322
tgctgactct caacattcta ctcctccaaa aaagaagaga aaggtagaag accccaagga    5382
ctttccttca gaattgctaa gttttttgag tcatgctgtg tttagtaata gaactcttgc    5442
ttgctttgct atttacacca caaaggaaaa agctgcactg ctatacaaga aaattatgga    5502
aaaatattct gtaacctttta taagtaggca taacagttat aatcataaca tactgttttt    5562
tcttactcca cacaggcata gagtgtctgc tattaataac tatgctcaaa aattgtgtac    5622
ctttagcttt ttaatttgta aaggggttaa taaggaatat ttgatgtata gtgccttgac    5682
tagagatcat aatcagccat accacatttg tagaggtttt acttgcttta aaaaacctcc    5742
cacacctccc cctgaacctg aaacataaaa tgaatgcaat tgttgttgtt aacttgttta    5802
ttgcagctta taatggttac aaataaagca atagcatcac aaatttcaca aataaagcat    5862
ttttttcact gcattctagt tgtggtttgt ccaaactcat caatgtatct tatcatgtct    5922 ggatccccg aacgccagca agacgtagcc cagcgcgtcg gccccgagat gcgccgcgtg    5982
cggctgctgg agatggcgga cgcgatggat atgttctgcc aagggttggt ttgcgcattc    6042
acagttctcc gcaagaattg attggctcca attcttggag tggtgaatcc gttagcgagg    6102
tgccgccctg cttcatcccc gtggcccgtt gctcgcgttt gctggcggtg tccccggaag    6162
aaatatattt gcatgtcttt agttctatga tgacacaaac cccgcccagc gtcttgtcat    6222
tggcgaattc gaacacgcag atgcagtcgg ggcggcgcgg tccgaggtcc acttcgcata    6282
ttaaggtgac gcgtgtggcc tcgaacaccg agcgaccctg cagcgacccg cttaacagcg    6342
tcaacagcgt gccgcagatc agcttgatat gaaaaagcct gaactcaccg cgacgtctgt    6402
cgagaagttt ctgatcgaaa agttcgacag cgtctccgac ctgatgcagc tctcggaggg    6462
cgaagaatct cgtgctttca gcttcgatgt aggagggcgt ggatatgtcc tgcgggtaaa    6522
tagctgcgcc gatggtttct acaaagatcg ttatgtttat cggcactttg catcggccgc    6582
gctcccgatt ccggaagtgc ttgacattgg ggaattcagc gagagcctga cctattgcat    6642
ctcccgccgt gcacagggtg tcacgttgca agacctgcct gaaaccgaac tgcccgctgt    6702
tctgcagccg gtcgcggagg ccatggatgc gatcgctgcg gccgatctta gccagacgag    6762
cgggttcggc ccattcggac cgcaaggaat cggtcaatac actacatggc gtgatttcat    6822
atgcgcgatt gctgatcccc atgtgtatca ctggcaaact gtgatggacg acaccgtcag    6882
tgcgtccgtc gcgcaggctc tcgatgagct gatgctttgg gccgaggact gccccgaagt    6942
ccggcacctc gtgcacgcgg atttcggctc caacaatgtc ctgacggaca atggccgcat    7002
aacagcggtc attgactgga gcgaggcgat gttcggggat tcccaatacg aggtcgccaa    7062
catcttcttc tggaggccgt ggttggcttg tatgagcag cagacgcgct acttcgagcg    7122
gaggcatccg gagcttgcag gatcgccgcg gctccgggcg tatatgctcc gcattggtct    7182
tgaccaactc tatcagagct tggttgacgg caatttcgat gatgcagctt gggcgcaggg    7242
tcgatgcgac gcaatcgtcc gatccggagc cgggactgtc gggcgtacac aaatcgcccg    7302
cagaagcgcg gccgtctgga ccgatggctg tgtagaagta ctcgccgata gtggaaaccg    7362
acgccccagc actcgtccgg atcgggagat ggggaggct aactgaaaca cggaaggaga    7422
caataccgga aggaacccgc gctatgacgg caataaaaag acagaataaa acgcacgggt    7482
gttgggtcgt ttgttcataa acgcggggtt cggtcccagg gctggcactc tgtcgatacc    7542
ccaccgagac cccattgggg ccaatacgcc cgcgtttctt cctttttccc accccacccc    7602
```

-continued

```
ccaagttcgg gtgaaggccc agggctcgca gccaacgtcg gggcggcagg ccctgccata    7662
gccactggcc ccgtgggtta gggacggggt cccccatggg aatggttta tggttcgtgg     7722
gggttattat tttgggcgtt gcgtggggtc aggtccacga ctggactgag cagacagacc    7782
catgttttt ggatggcctg gcatggacc gcatgtactg gcgcgacacg aacaccgggc      7842
gtctgtggct gccaaacacc cccgaccccc aaaaaccacc gcgcggattt ctggcgtgcc    7902
aagctgggta ccctctagag cgaattaatt cactggccgt cgttttacaa cgtcgtgact    7962
gggaaaaccc tggcgttacc caacttaatc gccttgcagc acatcccct ttcgccagct     8022
ggcgtaatag cgaagaggcc cgcaccgatc gcccttccca acagttgcgc agcctgaatg    8082
gcgaatggcg cctgatgcgg tattttctcc ttacgcatct gtgcggtatt tcacaccgca    8142
tatggtgcac tctcagtaca atctgctctg atgccgcata gttaagccag ccccgacacc    8202
cgccaacacc cgctgacgcg ccctgacggg cttgtctgct cccggcatcc gcttacagac    8262
aagctgtgac cgtctcccgg agctgcatgt gtcagaggtt ttcaccgtca tcaccgaaac    8322
gcgcgagacg aaaggggggg taccagcttc gtagctagaa catcatgttc tgggatatca    8382
gcttcgtagc tagaacatca tgttctggta ccccccctcgt gatacgccta ttttatagg    8442
ttaatgtcat gataataatg gtttcttaga cgtcaggtgg cacttttcgg ggaaatgtgc    8502
gcggaaccccc tatttgttta ttttttctaaa tacattcaaa tatgtatccg ctcatgagac   8562
aataaccctg ataaatgctt caataatatt gaaaaaggaa gagtatgagt attcaacatt    8622
tccgtgtcgc ccttattccc ttttttgcgg cattttgcct tcctgttttt gctcacccag    8682
aaacgctggt gaaagtaaaa gatgctgaag atcagttggg tgcacgagtg ggttacatcg    8742
aactggatct caacagcggt aagatccttg agagttttcg ccccgaagaa cgttttccaa    8802
tgatgagcac ttttaaagtt ctgctatgtg gcgcggtatt atcccgtatt gacgccgggc    8862
aagagcaact cggtcgccgc atacactatt ctcagaatga cttggttgag tactcaccag    8922
tcacagaaaa gcatcttacg gatggcatga cagtaagaga attatgcagt gctgccataa    8982
ccatgagtga taacactgcg gccaacttac ttctgacaac gatcggagga ccgaaggagc    9042
taaccgcttt tttgcacaac atgggggatc atgtaactcg ccttgatcgt tgggaaccgg    9102
agctgaatga agccatacca aacgacgagc gtgacaccac gatgcctgta gcaatggcaa    9162
caacgttgcg caaactatta actggcgaac tacttactct agcttcccgg caacaattaa    9222
tagactggat ggaggcggat aaagttgcag gaccacttct gcgctcggcc cttccggctg    9282
gctggtttat tgctgataaa tctggagccg gtgagcgtgg gtctcgcggt atcattgcag    9342
cactggggcc agatggtaag ccctcccgta tcgtagttat ctacacgacg gggagtcagg    9402
caactatgga tgaacgaaat agacagatcg ctgagatagg tgcctcactg attaagcatt    9462
ggtaactgtc agaccaagtt tactcatata ctttagat tgatttaaaa cttcattttt       9522
aatttaaaag gatctaggtg aagatccttt ttgataatct catgaccaaa atcccttaac    9582
gtgagttttc gttccactga gcgtcagacc ccgtagaaaa gatcaaagga tcttcttgag    9642
atcctttttt tctgcgcgta atctgctgct tgcaaacaaa aaaaccaccg ctaccagcgg    9702
tggtttgttt gccggatcaa gagctaccaa ctctttttcc gaaggtaact ggcttcagca    9762
gagcgcagat accaaatact gttcttctag tgtagccgta gttaggccac cacttcaaga    9822
actctgtagc accgcctaca tacctcgctc tgctaatcct gttaccagtg gctgctgcca    9882
gtggcgataa gtcgtgtctt accgggttgg actcaagacg atagttaccg gataaggcgc    9942
agcggtcggg ctgaacgggg ggttcgtgca cacagcccag cttggagcga acgacctaca   10002
```

-continued

```
ccgaactgag atacctacag cgtgagctat gagaaagcgc cacgcttccc gaagggagaa    10062
aggcggacag gtatccggta agcggcaggg tcggaacagg agagcgcacg agggagcttc    10122 caggggaaa cgcctggtat ctttatagtc ctgtcgggtt tcgccacctc tgacttgagc     10182
gtcgattttt gtgatgctcg tcagggggc ggagcctatg gaaaaacgcc agcaacgcgg     10242 ccttttacg gttcctggcc ttttgctggc cttttgctca catgttcttt cctgcgttat     10302 ccctgattc tgtggataac cgtattaccg cctttgagtg agctgatacc gctcgccgca     10362
gccgaacgac cgagcgcagc gagtcagtga gcgaggaagc ggaagagcgc ccaatacgca    10422
aaccgcctct ccccgcgcgt tggccgattc attaatgcag ctggcacgac aggtttcccg    10482
actggaaagc gggcagtgag cgcaacgcaa ttaatgtgag ttagctcact cattaggcac    10542
cccaggcttt acactttatg cttccggctc gtatgttgtg tggaattgtg agcggataac    10602
aatttcacac aggaaacagc tatgaccatg attacgccaa gctctctaga gctctagagc    10662
tctagagctc tagagagctt gcatgcctgc aggtcg                              10698
```

<210> SEQ ID NO 15
<211> LENGTH: 1459
<212> TYPE: PRT
<213> ORGANISM: Artificial Sequence
<220> FEATURE:
<223> OTHER INFORMATION: pTGF8-3

<400> SEQUENCE: 15

```
Met Gln Ile Glu Leu Ser Thr Cys Phe Phe Leu Cys Leu Leu Arg Phe
         -15                 -10                  -5

Cys Phe Ser Ala Thr Arg Arg Tyr Tyr Leu Gly Ala Val Glu Leu Ser
     -1   1               5                  10

Trp Asp Tyr Met Gln Ser Asp Leu Gly Glu Leu Pro Val Asp Ala Arg
             15                  20                  25

Phe Pro Pro Arg Val Pro Lys Ser Phe Pro Phe Asn Thr Ser Val Val
         30                  35                  40                  45

Tyr Lys Lys Thr Leu Phe Val Glu Phe Thr Asp His Leu Phe Asn Ile
                 50                  55                  60

Ala Lys Pro Arg Pro Pro Trp Met Gly Leu Leu Gly Pro Thr Ile Gln
             65                  70                  75

Ala Glu Val Tyr Asp Thr Val Val Ile Thr Leu Lys Asn Met Ala Ser
         80                  85                  90

His Pro Val Ser Leu His Ala Val Gly Val Ser Tyr Trp Lys Ala Ser
     95                  100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                 130                 135                 140

Lys Glu Asn Gly Pro Met Ala Ser Asp Pro Leu Cys Leu Thr Tyr Ser
             145                 150                 155

Tyr Leu Ser His Ala Asp Leu Val Lys Asp Leu Asn Ser Gly Leu Ile
         160                 165                 170

Gly Ala Leu Leu Val Cys Arg Glu Gly Ser Leu Ala Lys Glu Lys Thr
     175                 180                 185

Gln Thr Leu His Lys Phe Ile Leu Leu Phe Ala Val Phe Asp Glu Gly
190                 195                 200                 205

Lys Ser Trp His Ser Glu Thr Lys Asn Ser Leu Met Gln Asp Arg Asp
                 210                 215                 220
```

```
Ala Ala Ser Ala Arg Ala Trp Pro Lys Met His Thr Val Asn Gly Tyr
        225                 230                 235

Val Asn Arg Ser Leu Pro Gly Leu Ile Gly Cys His Arg Lys Ser Val
        240                 245                 250

Tyr Trp His Val Ile Gly Met Gly Thr Thr Pro Glu Val His Ser Ile
        255                 260                 265

Phe Leu Glu Gly His Thr Phe Leu Val Arg Asn His Arg Gln Ala Ser
270                 275                 280                 285

Leu Glu Ile Ser Pro Ile Thr Phe Leu Thr Ala Gln Thr Leu Leu Met
                290                 295                 300

Asp Leu Gly Gln Phe Leu Leu Phe Cys His Ile Ser Ser His Gln His
                305                 310                 315

Asp Gly Met Glu Ala Tyr Val Lys Val Asp Ser Cys Pro Glu Glu Pro
        320                 325                 330

Gln Leu Arg Met Lys Asn Asn Glu Ala Glu Asp Tyr Asp Asp Asp
        335                 340                 345

Leu Thr Asp Ser Glu Met Asp Val Val Arg Phe Asp Asp Asn Ser
350                 355                 360                 365

Pro Ser Phe Ile Gln Ile Arg Ser Val Ala Lys Lys His Pro Lys Thr
                370                 375                 380

Trp Val His Tyr Ile Ala Ala Glu Glu Asp Trp Asp Tyr Ala Pro
        385                 390                 395

Leu Val Leu Ala Pro Asp Asp Arg Ser Tyr Lys Ser Gln Tyr Leu Asn
        400                 405                 410

Asn Gly Pro Gln Arg Ile Gly Arg Lys Tyr Lys Lys Val Arg Phe Met
        415                 420                 425

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Glu Val Gly Asp Thr Leu
                450                 455                 460

Leu Ile Ile Phe Lys Asn Gln Ala Ser Arg Pro Tyr Asn Ile Tyr Pro
                465                 470                 475

His Gly Ile Thr Asp Val Arg Pro Leu Tyr Ser Arg Arg Leu Pro Lys
        480                 485                 490

Gly Val Lys His Leu Lys Asp Phe Pro Ile Leu Pro Gly Glu Ile Phe
        495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
                530                 535                 540

Asp Leu Ala Ser Gly Leu Ile Gly Pro Leu Leu Ile Cys Tyr Lys Glu
                545                 550                 555

Ser Val Asp Gln Arg Gly Asn Gln Ile Met Ser Asp Lys Arg Asn Val
        560                 565                 570

Ile Leu Phe Ser Val Phe Asp Glu Asn Arg Ser Trp Tyr Leu Thr Glu
575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620

Phe Asp Ser Leu Gln Leu Ser Val Cys Leu His Glu Val Ala Tyr Trp
        625                 630                 635
```

-continued

```
Tyr Ile Leu Ser Ile Gly Ala Gln Thr Asp Phe Leu Ser Val Phe Phe
            640             645                 650

Ser Gly Tyr Thr Phe Lys His Lys Met Val Tyr Glu Asp Thr Leu Thr
            655             660                 665

Leu Phe Pro Phe Ser Gly Glu Thr Val Phe Met Ser Met Glu Asn Pro
670             675                 680                 685

Gly Leu Trp Ile Leu Gly Cys His Asn Ser Asp Phe Arg Asn Arg Gly
            690             695                 700

Met Thr Ala Leu Leu Lys Val Ser Ser Cys Asp Lys Asn Thr Gly Asp
            705             710                 715

Tyr Tyr Glu Asp Ser Tyr Glu Asp Ile Ser Ala Tyr Leu Leu Ser Lys
            720             725                 730

Asn Asn Ala Ile Glu Pro Arg Ser Phe Ser Gln Asn Ser Arg His Gln
            735             740                 745

Ala Tyr Arg Tyr Arg Arg Gly Glu Ile Thr Arg Thr Thr Leu Gln Ser
750             755                 760                 765

Asp Gln Glu Glu Ile Asp Tyr Asp Asp Thr Ile Ser Val Glu Met Lys
            770             775                 780

Lys Glu Asp Phe Asp Ile Tyr Asp Glu Asp Glu Asn Gln Ser Pro Arg
            785             790                 795

Ser Phe Gln Lys Lys Thr Arg His Tyr Phe Ile Ala Ala Val Glu Arg
            800             805                 810

Leu Trp Asp Tyr Gly Met Ser Ser Ser Pro His Val Leu Arg Asn Arg
            815             820                 825

Ala Gln Ser Gly Ser Val Pro Gln Phe Lys Lys Val Val Phe Gln Glu
830             835                 840                 845

Phe Thr Asp Gly Ser Phe Thr Gln Pro Leu Tyr Arg Gly Glu Leu Asn
            850             855                 860

Glu His Leu Gly Leu Leu Gly Pro Tyr Ile Arg Ala Glu Val Glu Asp
            865             870                 875

Asn Ile Met Val Thr Phe Arg Asn Gln Ala Ser Arg Pro Tyr Ser Phe
            880             885                 890

Tyr Ser Ser Leu Ile Ser Tyr Glu Glu Asp Gln Arg Gln Gly Ala Glu
            895             900                 905

Pro Arg Lys Asn Phe Val Lys Pro Asn Glu Thr Lys Thr Tyr Phe Trp
910             915                 920                 925

Lys Val Gln His His Met Ala Pro Thr Lys Asp Glu Phe Asp Cys Lys
            930             935                 940

Ala Trp Ala Tyr Phe Ser Asp Val Asp Leu Glu Lys Asp Val His Ser
            945             950                 955

Gly Leu Ile Gly Pro Leu Leu Val Cys His Thr Asn Thr Leu Asn Pro
            960             965                 970

Ala His Gly Arg Gln Val Thr Val Gln Glu Phe Ala Leu Phe Phe Thr
            975             980                 985

Ile Phe Asp Glu Thr Lys Ser Trp Tyr Phe Thr Glu Asn Met Glu Arg
990             995                 1000                1005

Asn Cys Arg Ala Pro Cys Asn Ile Gln Met Glu Asp Pro Thr Phe Lys
            1010            1015                1020

Glu Asn Tyr Arg Phe His Ala Ile Asn Gly Tyr Ile Met Asp Thr Leu
            1025            1030                1035

Pro Gly Leu Val Met Ala Gln Asp Gln Arg Ile Arg Trp Tyr Leu Leu
            1040            1045                1050

Ser Met Gly Ser Asn Glu Asn Ile His Ser Ile His Phe Ser Gly His
```

```
                1055                1060                1065
Val Phe Thr Val Arg Lys Lys Glu Glu Tyr Lys Met Ala Leu Tyr Asn
1070                1075                1080                1085

Leu Tyr Pro Gly Val Phe Glu Thr Val Glu Met Leu Pro Ser Lys Ala
                1090                1095                1100

Gly Ile Trp Arg Val Glu Cys Leu Ile Gly Glu His Leu His Ala Gly
                1105                1110                1115

Met Ser Thr Leu Phe Leu Val Tyr Ser Asn Lys Cys Gln Thr Pro Leu
                1120                1125                1130

Gly Met Ala Ser Gly His Ile Arg Asp Phe Gln Ile Thr Ala Ser Gly
                1135                1140                1145

Gln Tyr Gly Gln Trp Ala Pro Lys Leu Ala Arg Leu His Tyr Ser Gly
1150                1155                1160                1165

Ser Ile Asn Ala Trp Ser Thr Lys Glu Pro Phe Ser Trp Ile Lys Val
                1170                1175                1180

Asp Leu Leu Ala Pro Met Ile Ile His Gly Ile Lys Thr Gln Gly Ala
                1185                1190                1195

Arg Gln Lys Phe Ser Ser Leu Tyr Ile Ser Gln Phe Ile Ile Met Tyr
                1200                1205                1210

Ser Leu Asp Gly Lys Lys Trp Gln Thr Tyr Arg Gly Asn Ser Thr Gly
                1215                1220                1225

Thr Leu Met Val Phe Phe Gly Asn Val Asp Ser Ser Gly Ile Lys His
1230                1235                1240                1245

Asn Ile Phe Asn Pro Pro Ile Ile Ala Arg Tyr Ile Arg Leu His Pro
                1250                1255                1260

Thr His Tyr Ser Ile Arg Ser Thr Leu Arg Met Glu Leu Met Gly Cys
                1265                1270                1275

Asp Leu Asn Ser Cys Ser Met Pro Leu Gly Met Glu Ser Lys Ala Ile
                1280                1285                1290

Ser Asp Ala Gln Ile Thr Ala Ser Ser Tyr Phe Thr Asn Met Phe Ala
                1295                1300                1305

Thr Trp Ser Pro Ser Lys Ala Arg Leu His Leu Gln Gly Arg Ser Asn
1310                1315                1320                1325

Ala Trp Arg Pro Gln Glu Asn Asn Pro Lys Glu Trp Leu Gln Val Asp
                1330                1335                1340

Phe Gln Lys Thr Met Lys Val Thr Gly Val Thr Thr Gln Gly Val Lys
                1345                1350                1355

Ser Leu Leu Thr Ser Met Tyr Val Lys Glu Phe Leu Ile Ser Ser Ser
                1360                1365                1370

Gln Asp Gly His Gln Trp Thr Leu Phe Phe Gln Asn Gly Lys Val Lys
                1375                1380                1385

Val Phe Gln Gly Asn Gln Asp Ser Phe Thr Pro Val Val Asn Ser Leu
1390                1395                1400                1405

Asp Pro Pro Leu Leu Thr Arg Tyr Leu Arg Ile His Pro Gln Ser Trp
                1410                1415                1420

Val His Gln Ile Ala Leu Arg Met Glu Val Leu Gly Cys Glu Ala Gln
                1425                1430                1435

Asp Leu Tyr
        1440

<210> SEQ ID NO 16
<211> LENGTH: 43
<212> TYPE: DNA
<213> ORGANISM: Artificial Sequence
```

```
-continued

<220> FEATURE:
<223> OTHER INFORMATION: primer

<400> SEQUENCE: 16
ggaattccgc aaaggttatg cagcgcgtga acatgatcat ggc         43

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
cgcggatcca ttaagtgagc tttgtttttt ccttaatcc              39
```

RECOMBINANT BLOOD CLOTTING FACTORS

This application is national stage entry of PCT/EP01/03220, filed Mar. 21, 2001, which claims priority to EP/0016225.6, filed Mar. 22, 2000 and U.S. provisional application No. 60/203,249, filed May 8, 2000, each of which are specifically incorporated herein by reference.

The present invention relates to an improved method for the production of recombinant human blood clotting factors, in particular of factor VIII and factor IX, utilizing an immortalized human cell line stably expressing viral transcription activator proteins and carrying a vector having a promoter functionally linked to a DNA sequence coding for a blood coagulating factor, provided that said promoter is not a viral promoter which is stimulated by said viral transcription activator proteins; an immortalized human cell line carrying said vector; factor VIII muteins particularly suitable for the above production method; pharmaceutical compositions comprising such factor VIII muteins and the use of such factor VIII muteins for preparing a medicament for treating hemophilia.

SUMMARY OF THE RELATED ART

Hemophiliacs are suffering from hemorrhagic morbidity caused by the disturbed function of protein components of the blood coagulation cascade. Dependent on the affected clotting factor two types of hemophilia can be distinguished. Both have in common the inhibited conversion of soluble brinogen to an insoluble fibrin-clot. They are recessive X-chromosomally-linked genetic diseases affecting mainly the male population.

Hemophilia A affects 1-2 individuals per 10.000 males. It is caused by the deficiency or absence of factor VIII, a very large glycoprotein (Mr approximately 330 kDa (Furie B., Furie B. C., *Cell* (1988) 53, 505-518)), which represents an important element of the blood coagulation cascade. The polypeptide sequence can be subdivided in three regions, an N-terminal region consisting of the so-called A1 and A2-domains, a central B-domain region and a C-terminal region composed of the A3, C1 and C2 domains. In the blood coagulation factor VIII occurs as an inactive precursor. It is bound tightly and non-covalently to von Willebrand Factor (vWF), which acts as a stabilizing carrier protein. Proteolytical cleavage of factor VIII by thrombin at three specific positions (740, 372, 1689) leads to its dissociation from vWF and releases the procoagulant function within the cascade. In its active form factor VIII functions as a cofactor for factor IXa, thereby accelerating the proteolytic activation of factor X by several orders of magnitude.

Hemophilia B occurs in about 1 of 25,000 males. It is characterized by the deficiency of the serine protease factor IX (Christmas factor). This 415 amino-acid polypeptide is synthesized in the liver as a 56 kDa glycoprotein. In order to attain its proper function a posttranslational carboxylation step is required which only occurs in the presence of vitamin K.

Treatment of both types of bleeding disorder traditionally involves infusions of human plasma-derived protein concentrates of factor VIII or factor IX. Although this method represents an efficient therapy for hemophiliacs it carries the risk of transmission of various infectious agents, such as viruses causing hepatitis or AIDS, or thromboembolic factors. Alternatively several recombinant DNA techniques for the production of clotting factors have been described. For this purpose the corresponding cDNAs of wild type factor VIII and factor IX have been isolated and cloned into suitable expression vectors (EP-A-160457; WO-A-86/01961, U.S. Pat. Nos. 4,770,999, 5,521,070 and 5,521,070).

In the case of factor VIII recombinant expression of subunits for the production of complexes showing coagulant activity is known in the art (e.g., from EP-A-150735, EP-A-232112, EP-A-0500734, WO-91/07490, WO-95/13300 U.S. Pat. Nos. 5,045,455 and 5,789,203). Moreover, the expression of truncated cDNA-versions partially or entirely lacking the sequence coding for the highly glycosylated B-domain have been described (e.g. in WO-86/06101, WO-87/04187, WO-87/07144, WO-88/00381, EP-A-251843, EP-A-253455, EP-A-254076, U.S. Pat. Nos. 4,868,112 and 4,980,456, EP-A-294910, EP-A-265778, EP-A-303540 and WO-91/09122). More recently a variety of selected point mutations have been introduced to inhibit proteolytic inactivation of factor VIII by activated protein C or to reduce the immunogenicity resulting in the formation of inhibitory antibodies by the treated patients (e.g., U.S. Pat. Nos. 5,859,204, 5,422,260 and 5,451,521, WO-97/49725 and WO-99/29848).

The recombinant clotting factors were usually isolated from the medium of stably transfected eukaryotic and preferably mammalian cell lines. It was, however, general practice to employ non-human cell lines in the production methods disclosed in the references mentioned herein before in order to exclude the risk of copurifying some infectious agents which may be harbored and expressed by human cells.

However, especially for factor VIII, the use of non-human cell lines encountered certain disadvantages. For example unsatisfactory secretion levels of the expressed protein into the medium have been reported. This may be due to slight differences within different types of mammalian cells concerning intracellular pathways for protein translation and modification, which also might have an effect on the biological activity of the expressed polypeptide. Apart from this, there were concerns that the therapeutic proteins purified from non-human expression systems are contaminated with cellular components which can give rise to antigenic reactions in the patients.

Moreover, proteins expressed by non-human expression systems may have non-human glycosylation patterns giving rise to antigenic reactions in the patient. However, biological stability and efficacy of clotting factors is substantially influenced by their N-glycosylation pattern. Peripheral and terminal monosaccharides are especially important because they are detected by specific receptors from cells which are responsible for their degradation. Clotting factors carry sialic acid residues as terminal monosaccharides. Modification of sialic acids in the antennae of glycoproteins, as for example clotting factors, can result in heterogenous glycosylation patterns. Thus, biological stability and efficacy are affected when modification occurs. Hence, it is an important consideration in the production of recombinant clotting factors to evaluate the influence of glycosylation from non-human production cell lines versus human cell lines. Generally speaking, it seems plausible that human cell lines are more qualified for the production of recombinant clotting factors than non-human cell-lines. The reason for this assumption is that extraneous oligosaccharide will not likely be incorporated into the oligosaccharide moiety during synthesis of recombinant factors.

On the other hand, general methods for high level protein expression of a desired gene comprising immortalized, stably transfected mammalian cell lines expressing viral transcription activator proteins have been made available for some time (e.g. U.S. Pat. No. 5,712,119). Further these cell lines are transformed with a vector construct where a suitable viral transcription promoter is operatively associated with a DNA sequence defining a gene of interest, the transcription activator proteins activate the viral transcription promoter and hence initiate the expression of the gene of interest. Again, there were concerns that the transcription activator proteins expressed by these cell lines may give rise to contaminations in the target therapeutic protein.

In view of the above there was still a need for an effective production method for human blood clotting factors.

Surprisingly, it was found that a non-contaminated blood clotting factor can be obtained with the above mentioned immortalized human cell lines. In particular, the immortalized cell lines—if carrying a vector having a promoter functionally linked to a DNA sequence coding for the blood clotting factor and despite the fact that the promoter is not a viral promoter which is stimulated by said viral transcription activator proteins—are capable of expressing the blood clotting factor. In combination with suitable protein purification and virus-inactivation protocols this method provides an effective system to produce safe and highly active recombinant blood clotting factors for therapeutic applications in humans. Moreover, particular factor VIII muteins were found which are exceptionally stable against proteolytic inactivation and thus allow to be subjected to vigorous virus inactivation protocols.

SUMMARY OF THE INVENTION

The present invention provides (1) a method for the production of recombinant human blood clotting factor which comprises (a) culturing an immortalized human cell line stably expressing at least one viral transcription activator protein and carrying a vector having a promoter functionally linked to a DNA sequence coding for the human blood clotting factor, provided that said promoter is not a viral promoter which is stimulated by said at least one viral transcription activator protein, and (b) isolating the blood clotting factor from the culture broth;

(2) a preferred embodiment of the method defined in (1) above, wherein the human blood clotting factor is factor VIII or a mutein thereof;

(3) a preferred embodiment of the method defined in (2) above, wherein the factor VIII is a mutein having at least one of the following mutations:

(a) Val at position 162 has been replaced by another neutral amino acid residue, (b) Ser at position 2011 has been replaced by another hydrophilic amino acid residue, (c) Val at position 2223 has been replaced by an acidic amino acid residue, and (d) the B-domain between positions Arg740 and Glu1649 has been replaced by an Arg-rich linker peptide comprising 10 to 25, preferably 14 to 20 amino acid residues, wherein said factor VIII numbering is relative to the mature wild-type factor VIII sequence shown in SEQ ID NO: 2;

(4) a preferred embodiment of the method defined in (1) above, wherein the human blood clotting factor is factor IX or a mutein thereof;

(5) an immortalized human cell line carrying a vector coding for a human blood clotting factor as defined in (1) to (4) above;

(6) a factor VIII mutein as defined in (3) above;

(7) a DNA sequence coding for the factor VIII mutein as defined in (6) above;

(8) a vector comprising the DNA as defined in (7) above;

(9) a vector as defined in (8) above which is a gene transfer vector;

(10) a host cell being transformed with a vector as defined in (8) above and/or comprising a DNA sequence as defined in (7) above;

(11) a pharmaceutical composition comprising the factor VIII mutein as defined in (6) above or a gene transfer vector as defined in (9) above;

(12) the use of the factor VIII mutein as defined in (6) above or a gene transfer vector as defined in (9) above for preparing a medicament for treating hemophilia; and

(13) a method for treating hemophilia which comprises administering human hemophiliacs a factor VIII mutein as defined in (6) above or a gene transfer vector as defined in (9) above.

DESCRIPTION OF THE FIGURES

FIG. 7A shows the calibration curve of FVIII ELISA as described in Example 5.

FIG. 7B depicts the results of the determination of recombinant FVIII concentrations in different culture filtrates as described in Example 5.

DETAILED DESCRIPTION OF THE INVENTION

Figure 1:
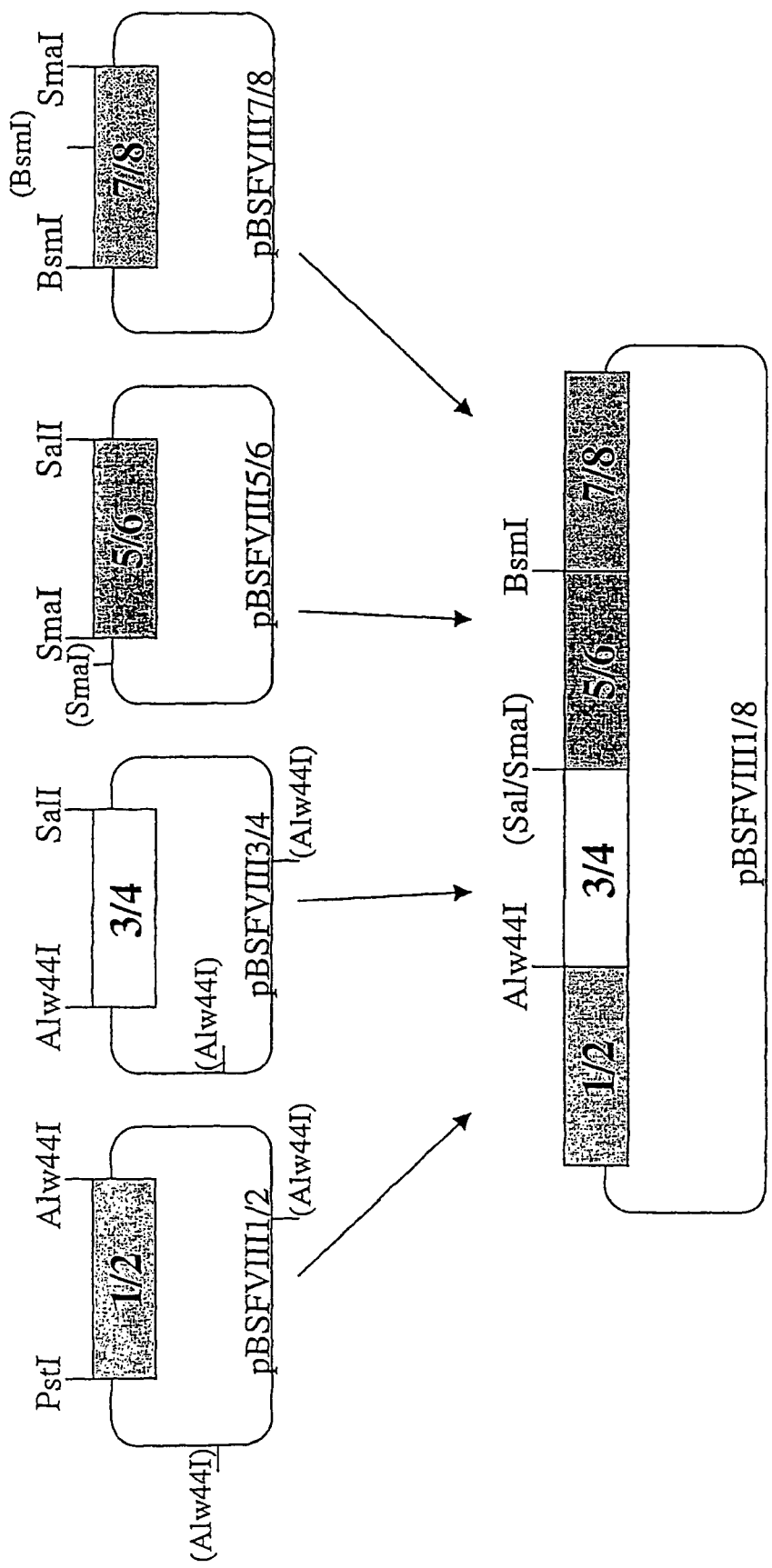
FIG. 1 shows the fragments utilized for the construction of factor VIII with a deleted B-domain (Example 1).

"Functionally linked" refers to configurations of the vector where the promoter is located within the vector in such a manner that it can stimulate transcription of the DNA sequence coding for the human blood clotting factor. "Not functionally linked" refers to a configuration where the promoter is so remotely located from the expressed gene sequence of the blood clotting factor that it cannot stimulate its transcription.

"Gene" refers to a DNA sequence encoding a polypeptide optionally including leader and trailer sequences and introns and exons.

"Vector" refers to any genetic construct, such as plasmid, phage, cosmid, etc., which is capable of replication when associated with the proper control elements. The term includes cloning and expression vehicles. "Carrying a vector" includes both, the stable and transient incorporation of a functional DNA segments into the host cell. The stable incorporation is, however, preferred.

"Gene transfer vector" in accordance with the present invention includes a vector suitable for gene therapy. Such vector comprises functional sequences for the desired purpose as known in the art.

The term "mature" refers to the molecular structure of a given protein directly after its cellular secretion (i.e., lacking its N-terminal export-signal polypeptide).

"Promoter" refers to a region of regulatory DNA sequences for the control of transcription of a gene to which RNA polymerases bind.

"Therapeutically effective dose" of the pharmaceutical composition of the invention refers to a dose effective for treatment or prophylaxis, for example, a dose that yields effective treatment or reduction of the symptoms of hemophilia. The determination of a therapeutically effective dose is within the purview of one skilled in the art.

"Encodes" or "encoding" refers to a property of the nucleic acid sequence being transcribed (in case of DNA) or translated (in case of mRNA) into a polypeptide in vitro or in vivo when placed under the control of an appropriate regulatory sequence.

For the purpose of this application "express", "expressing" or "expression" refers to the transcription and translation of a gene encoding a protein.

The present invention as described in (1) to (13) above is hereinafter described in more detail. In accordance with embodiment (1) of the invention of the present application the promoter functionally linked to the DNA sequence coding for the human blood clotting factor is not a viral promoter which is stimulated by the at least one viral transcription activator protein expressed by the immortalized human cell line.

The immortalized human cell line preferably is an immortalized kidney, bladder, liver, lung, cardiac muscle, smooth muscle, ovary or gastrointestinal cell. More preferably the immortalized human cell line is derived from an embryonic human kidney cell and most preferably it is cell line 293 T (ECACC: tsa201, ref. 96121229; DSM ACC2494)

The at least one transcription activator protein expressed by the immortalized cell line includes Simian virus T antigen, adenovirus E1A or E1B proteins, a protein encoded by the bovine papilloma virus early region DNA sequence and herpes virus IE proteins. Preferably the immortalized cell expresses at least two viral transcription activator proteins, e.g., a temperature sensitive SV40 T antigen and adenovirus E1A protein (such as the above cell line 293 T).

The promoter functionally linked to the DNA sequence coding for the human blood clotting factor preferably includes
(i) viral promoters being not stimulated by the activator protein expressed by the immortalized cell as defined above (such as SV40 and CMV);
(ii) housekeeping host promoters (albumin); and
(iii) tissue specific promoters (such as α-antitrypsin for liver). The most preferable promoter in accordance with the invention is a CMV promoter (while the transcription activator protein expressed by the immortalized cell is not stimulating said promoter).

In accordance with the invention the vector may carry additional viral promoters which are stimulated by said viral transcription activator proteins, but which are not functionally linked to the blood clotting factor. Such viral promoters are selected from promoters derived from adenovirus, rous sarcoma virus and cytomegalovirus. The vector may further comprise one or more of the following functional sequences: selection markers, regulatory sequences (e.g. PRE), etc.

The human blood clotting factor according to embodiment (1) of the invention includes, but is not limited to, factor IX, factor VIII, factor VII, factor V, von Willebrand factor (vWF) and the like.

In preferred embodiment (2) of the invention, the vector comprises a DNA sequence coding for factor VIII or a mutein thereof. Whereas recombinant factor IX is in general structurally identical to the wild type protein isolated from blood plasma, several modified factor VIII expression constructs have been designed for recombinant expression. Considering the domain structure of the functional factor VIII polypeptide important interaction sites with vWF are located in the A3-domain (amino acid 1680-1689) and in the C2-domain (Kaufman & Pipe, *Haemophilia* (1998) 4, 370-379). Cleavage after 1689 was proposed to liberate factor VIII from vWF and permit factor VIII to interact with charged phospholipids. Recombinant factor VIII constructs lacking the vWF-binding site were shown to be extremely prone to proteolytic digestion when injected into factor VIII-deficient mice. Recombinant expression of truncated factor VIII constructs in mammalian cell cultures demonstrated that the complete deletion of the B-domain did not alter the biological activity of the corresponding factor VIII-like protein (Eaton et. al., *Biochemistry* (1986) 25, 8343-8347). In addition the observed expression rates of B-domain deleted constructs were significantly higher compared to wild-type factor VIII due to an increased mRNA-level in the cells (Pittman et al., *Blood* (1993) 81, 2925-2935). Four recombinant factor VIII products (Recombinate® Baxter HealthCare; Kogenate® and Kogenate FS® Bayer Corporation and Refacto® Wyeth, Genetics Institute) are currently on the market.

In preferred embodiment (3) of the invention the factor VIII mutein has at least one of the following mutations (a) to (d):

(a) Val at position 162 has been replaced by another neutral amino acid residue;

(b) Ser at position 2011 has been replaced by another hydrophilic amino acid residue;

(c) Val at position 2223 has been replaced by an acidic amino acid residue; and (d) the B-domain between positions Arg740 and Glu1649 has been replaced by an Arg-rich linker peptide comprising 10 to 25, preferably 14 to 20 amino acid residues, wherein said factor VIII numbering is relative to the amino acid sequence of wild-type factor VIII shown in SEQ ID NO: 2 (being the amino acid sequence of the mature peptide not including the 19 amino acid signal peptide, but including the entire B-domain (WO 99/29848)).

"Another neutral amino acid residue" in accordance with the present invention includes Gay, Ala, Leu, Ile, Met and Pro and preferably is Ala. The "another hydrophilic amino acid" includes Asn, Thr and Gln and preferably is Asn. The acidic amino acid residue is selected from Glu and Asp and preferably is Glu.

Among the factor VIII muteins of embodiment (3) it is preferred that the factor VIII mutein has at least one of the mutations (a), (b) and (c), more preferably at least one of the mutations (a) and (b), and most preferably all three mutations (a) to (c) as defined above. It is particularly preferred that the mutein comprises all three of the mutations V162A, S2011N and V2223E.

On the same token, the DNA sequence comprised by the vector of embodiment (3) of the invention has the mutations T485C, G6032A and T6668A relative to the DNA sequence of the mature wild-type factor VIII shown in SEQ ID NO: 1. In a preferred embodiment the DNA sequence also contains the quiet (i.e., silent) mutation T6816C (again said numbering being relative to the DNA sequence of the mature wild-type factor VIII).

Among the factor VIII muteins of embodiment (3) it is alternatively preferred that the factor VIII mutein has mutation (d) as defined above.

Figure 5:
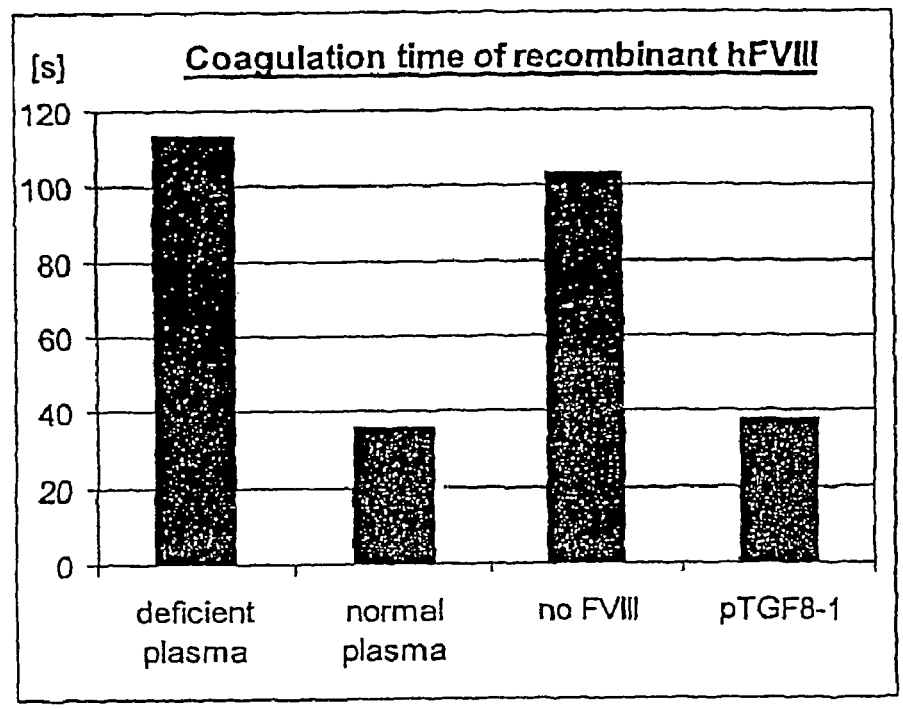
FIG. 5A depicts a preferred linker sequence of the present invention (SEQ ID NO: 9).
FIG. 5B shows the coagulation time of recombinant hFVIII as determined in Example 6.

A preferred expression system of the invention utilizes a unique factor VIII mutein which—besides the point mutation (a) to (c) as defined herein before—partially or entirely lacks its B-domain, preferably a mutein where the B-domain between position R740 and E1649 is replaced by a characteristic Arg-rich amino acid spacer as defined in (d) above. "Arg-rich" in accordance with the present invention means that said spacer comprises at least 3, preferably at least 4 Arg residues. In a most preferred embodiment said spacer consists of eight amino acids of the wilde type B-domain followed by eight amino acids of a variable domain (see FIG. 5A, SEQ ID NO: 9). In such construct having the B-domain modifications discussed herein before the proposed vWF-binding site remains unchanged to prevent an immediate proteolytic digestion of secreted factor VIII in the cell culture medium or later on in the blood of the treated patients. Only after specific activation by thrombin cleavage factor VIII will be released from vWF. The cDNA for the preferred factor VIII was constructed by assembling four DNA-fragments, e.g., as described in Example 1.

The protein of embodiment (3) of the invention may comprise additional N- or C-terminal sequences including, but not limited to, the natural export signal peptide (corresponding to amino acid residues −19 to −1 of the proteins shown in SEQ ID NOs 4, 13 and 15) or a fragment or analogue thereof, artificial peptides (e.g. oligo-His-tags for high-affinity purification) and the like.

Figure 2:
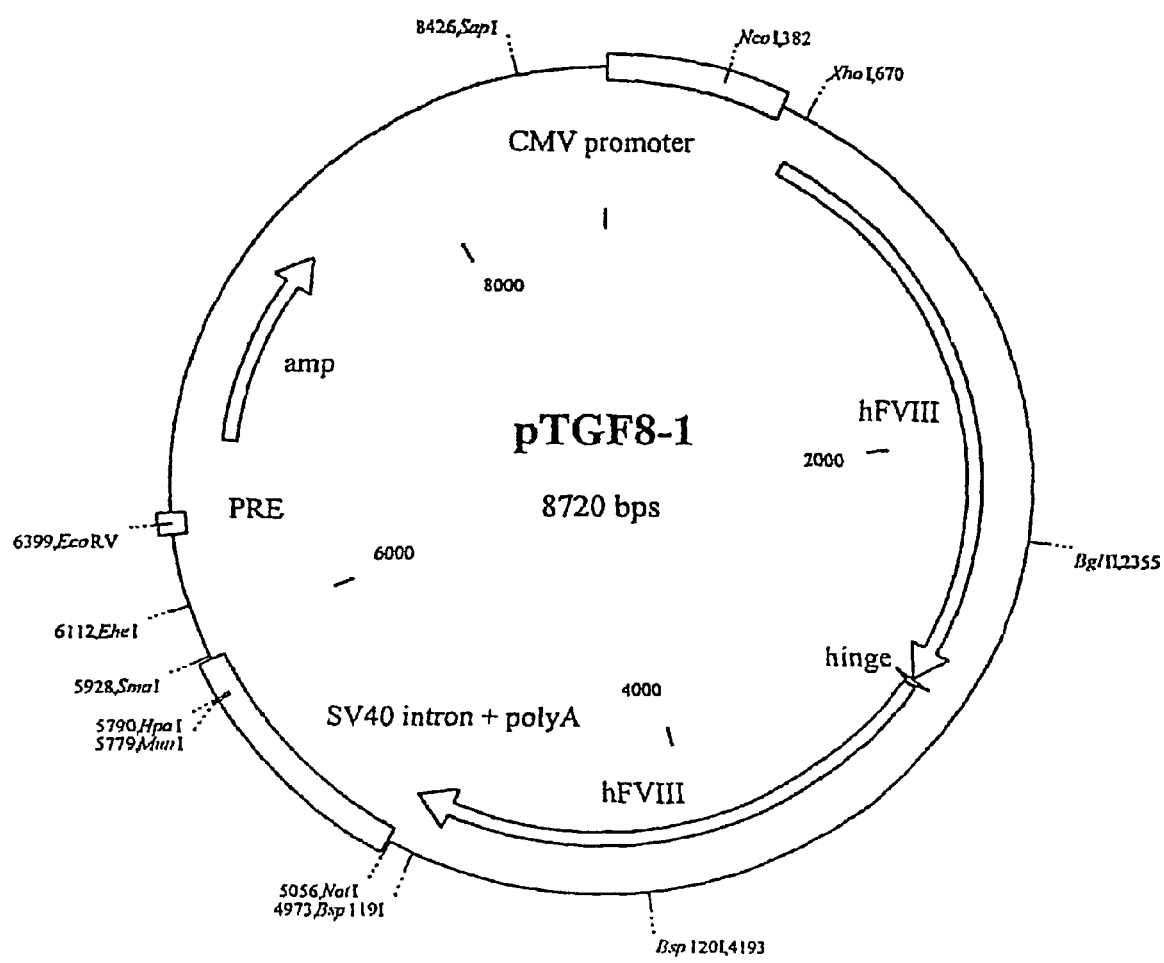
FIG. 2 shows the vector pTGF8-1, 8720 bps circular DNA, the exact DNA sequence thereof is given in SEQ ID NO: 3 (for the factor VIII protein encoded by said DNA sequence see SEQ ID NO: 4).

The most preferred vector for the expression of factor VIII is vector pTGF8-1 shown in FIG. 2. The DNA sequence of said vector is shown in SEQ ID NO: 3, and it encompasses all five mutations addressed previously, including the muteins T485C, G6032A, T6668A and T6816C of the wild type sequence (SEQ ID NO: 1), which correspond to muteins ( T1217C, G4088A, T4724A and T4872C of SEQ ID NO: 3. The vector also encompasses a DNA sequence coding for the B-domain linker of SEQ ID NO: 9. Vector pTGF8-1 encodes the factor VIII mutein depicted in SEQ ID NO: 4.

Figure 6:
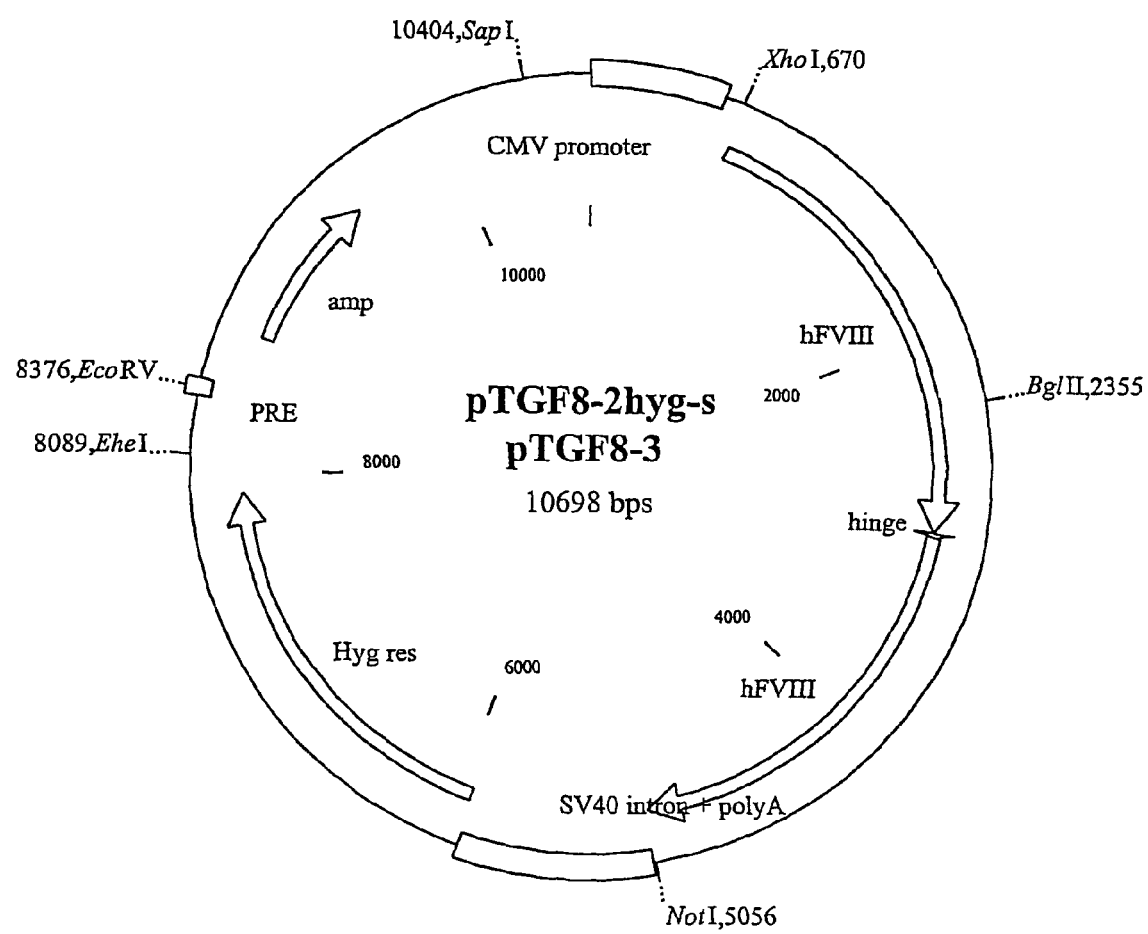
FIG. 6 shows the common molecular structure of pTGF8-2hyg-s and pTGF8-3, 10698 bps circular DNA, the exact DNA sequences thereof are given in SEQ ID NOs: 12 and 14 (for the factor VIII protein encoded by said DNA sequence see SEQ ID NO: 13 and 15).

Further most preferred vectors are pTGF8-2hyg-s and pTGF8-3, the common molecular structure of which is depicted in FIG. 6.

pTGF8-2hyg-s shown in SEQ ID NO: 12 contains the silent mutation T6816C only, resulting in a factor VIII mutein having the substitution of the B domain by the linker peptide SEQ ID NO. 9, but no further change in the primary protein structure referring to the wild type sequence SEQ ID NO. 2.

pTGF8-3 shown in SEQ ID NO: 14 contains mutations T485C, T6668A and T6816C, resulting in a factor VIII mutein showing amino acid substitutions V162A and V2223E referring to SEQ ID NO. 2 in addition to the substitution of the B domain as described above.

In the case of the production of factor VIII the culturing is performed in the presence of von Willebrand factor. The von Willebrand factor is preferably used in an amount of 10 to 100, more preferably 50 to 60 mol vWF per mol factor VIII (in the culture broth and/or in the factor VIII solution during the purification procedure (see below).

Figure 3:
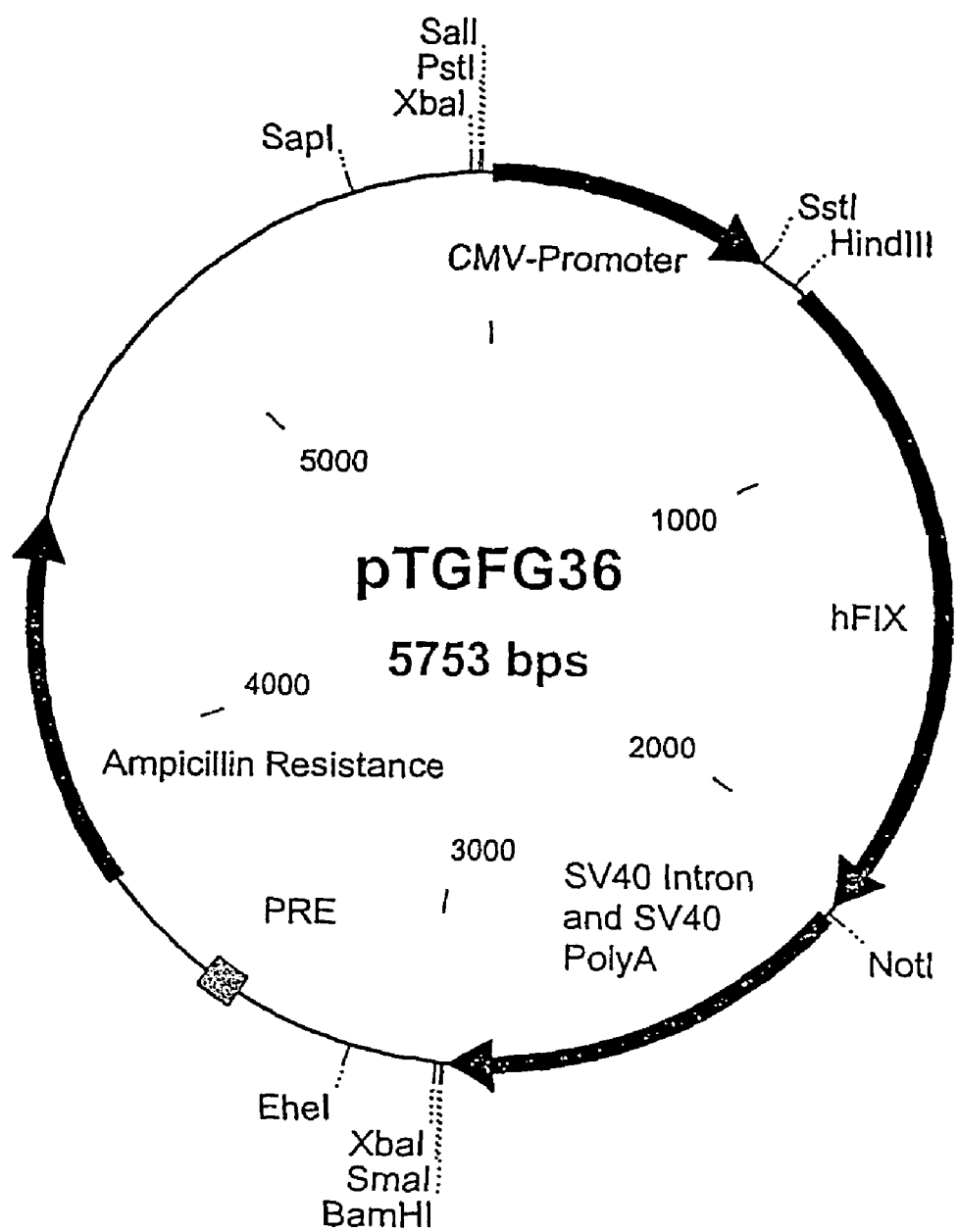
FIG. 3 shows vector pTGFG36, 5753 bps circular DNA, the exact DNA sequence thereof is given in SEQ ID NO: 6 (bases 689-2071 within SEQ ID NO: 6 coding for the factor IX protein).
Figure 4:
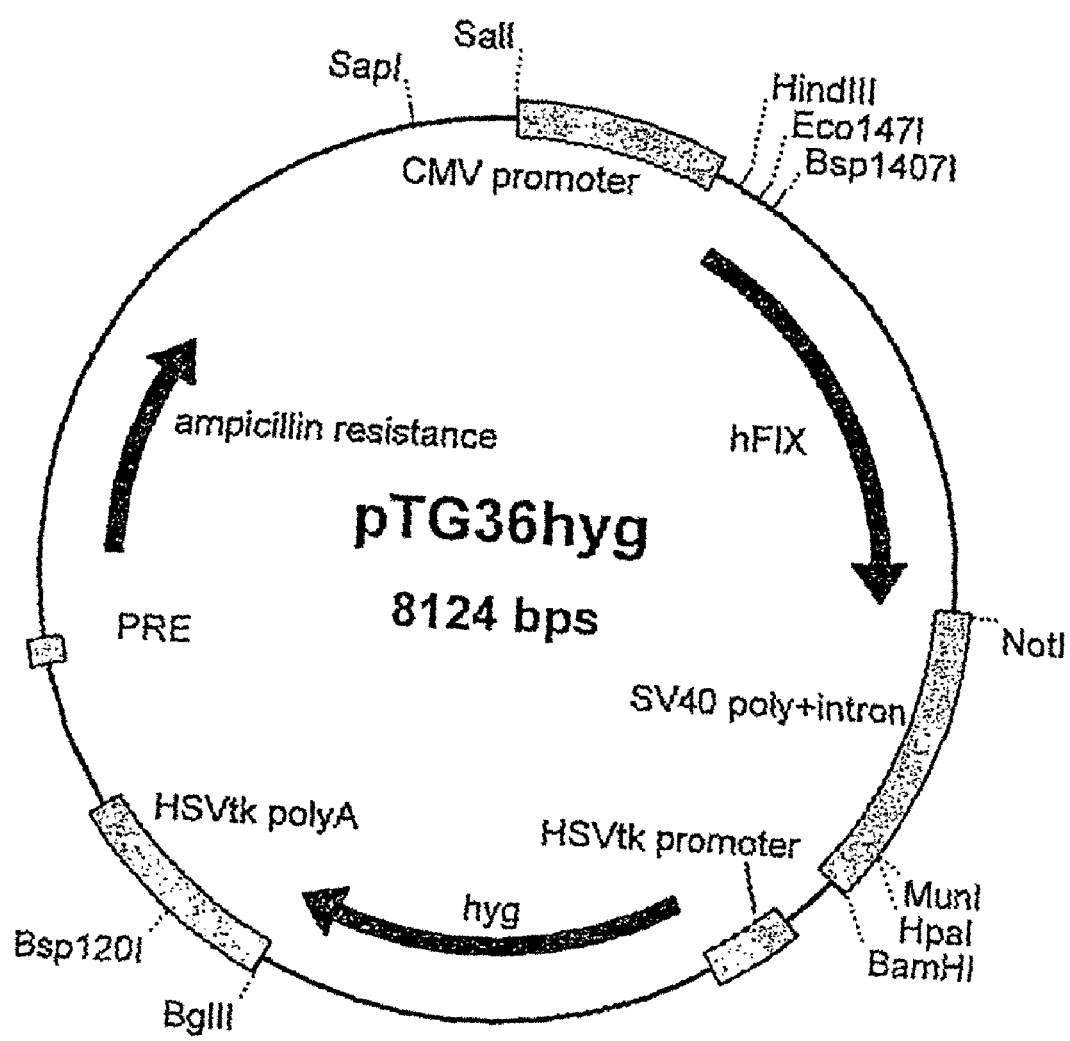
FIG. 4 shows vector pTG36hyg, 8124 bps circular DNA.

In preferred embodiment (4) of the present invention the human blood clotting factor is factor IX or a mutein thereof, preferably is wild-type factor IX shown in SEQ ID NO: 5. Suitable muteins of factor IX include point mutated and truncated forms of the factor IX. The most preferred vector for expression of factor IX are vectors pTGFG36 and pTG36hyg shown in FIGS. 3 and 4, respectively.

In case of the production of factor IX, the culturing is preferably performed in the presence of vitamin K which may be present in an amount of 0.1 to 100 µg/ml culture broth, more preferably 1 to 20 µg/ml culture broth.

The method according to embodiment (1) of the invention further comprises the steps (c) purifying the blood clotting factor isolated in step (b) and/or (d) subjecting the blood clotting factor isolated in step (b) or purified in step (c) to a virus inactivation treatment.

Suitable purification steps include methods which were known in the art to maximize the yield of a pure, stable and highly active product and are selected from immunoaffinity chromatography, anion exchange chromatography, size exclusion chromatography, etc., and combinations thereof. In particular, detailed purification protocols for coagulation factors from human blood plasma are, e.g., disclosed in WO93/15105, EP0813597, WO96/40883 and WO 96/15140/50. They can easily be adapted to the specific requirements needed to isolate recombinant factors VIII and IX. For factor IX an effective protocol has been introduced containing an ammonium sulfate precipitation step followed by DEAE and HIC tentacle chromatography as well as heparin affinity chromatography (U.S. Pat. No. 5,919,909). Quantity and activity of the purified protein during and after the purification procedure may be monitored by ELISA and coagulation assays.

To overcome the problems of possible infectious contaminations in the purified protein samples or in the product directly obtained from the cell culture supernatant containing the secreted recombinant protein of choice, the samples and/or the culture supernatant might be treated with procedures for virus inactivation including heat treatment (dry or in liquid state, with or without the addition of chemical substances including protease inhibitors). After virus inactivation a further purifying step for removing the chemical substances may be necessary. In particular, for factor VIII isolated from blood plasma the recovery of a high purity virus-inactivated protein by anion exchange chromatography was described (WO93/15105). In addition several processes for the production of high-purity, non-infectious coagulation factors from blood plasma or other biological sources have been reported. Lipid coated viruses are effectively inactivated by treating the potentially infectious material with a hydrophobic phase forming a two-phase system, from which the water-insoluble part is subsequently removed. A further advantage has been proven to complement the hydrophobic phase treatment simultaneously or sequentially with a treatment with non-ionic biocompatible detergents and dialkyl or trialkyl phosphates. (WO 9636369, EP0131740, U.S. Pat. No. 6,007,979). Non-lipid coated viruses require inactivation protocols consisting in treatment with non-ionic detergents followed by a heating step (60-65° C.) for several hours (WO94/17834).

In view of the above results it is believed that the combination of an effective protein expression system based on a human cell line together with approved methods for inactivation of potentially dangerous infectious agents serve as a safe and easy to use-system for production of recombinant clotting factors.

Moreover, in accordance with embodiment (6) of the invention it is provided a superior factor VIII mutant. Said factor VIII mutant can be part of pharmaceutical compositions, can be used for preparing medicaments for treating hemophilia and can be applied in methods for treating hemophilia (embodiments (11) to (13) of the invention). The above pharmaceutical compositions and the above medicaments may comprise the factor VIII in a therapeutically effective dose, e.g., from 50 to 500 µg (with 200 ng factor VIII corresponding to one International Unit (IU)). Depending on the type of hemophilia, a patient receives an annual dose of factor VIII of up to 200,000 IU, which is usually administered in weekly or twice weekly doses.

The pharmaceutical compositions, medicaments or preparations applied in methods for treating hemophilia of embodiments (11) to (13) contains a therapeutically effective dose of the factor VIII mutein of embodiment (6) or the gene transfer vector of embodiment (9). In case of the former, it may further comprise pharmaceutically acceptable additives including human serum albumin (HSA; preferably about 1 mg/ml solution); inorganic salts such as $CaCl_2$ (preferably 2 to 5 mM), amino acids such as glycine, lysine, and histidine (preferably 0.1 to 1 M per amino acid); disaccharides such as sucrose and/or trehalose (preferably 0.4 to 1 M); organic salts such as Na-citrate (preferably up to 50 mM); etc. The preparations may be aqueous or non-aqueous. In the latter case the major component is glycerol and/or polyethylene glycol (e.g., PEG-300). The preparation may also be in the dry form (to be dissolved in the desired solvent prior to administration).

As set forth above, the gene transfer vector in accordance with embodiment (9) of the invention can also be part of pharmaceutical compositions, can be used for preparing medicaments for treating hemophilia and can be applied in methods for treating hemophilia (embodiments (11) to (13) of the invention). Said pharmaceutical compositions and medicaments may further comprise suitable matrix formulations, e.g., lipids or hormones as discussed in WO 00/49147 (the disclosure thereof being herewith incorporated by reference). The pharmaceutical composition or medicament comprising the gene transfer vector or the gene transfer vector of the present invention may be administered orally, intravenously, intramuscularly, subcutaneously, tropically, through mucosa (including buccal, nasal spray) or by gene gun. Oral administration (e.g., in a micronized hormone dispersion) is preferred.

The factor VIII mutein of embodiment (6) of the invention is preferably as defined with reference to embodiment (3) above. Said FVIII mutein may further be prepared by standard recombinant techniques, e.g. a method comprising (a) culturing a host cell transformed with the vector of embodiment (8) and/or comprising the DNA of embodiment (7) (which also includes culturing an immortalized human cell line stably expressing at least one viral transcription activator protein and carrying a vector having a viral transcription promoter functionally linked to a DNA sequence coding for the human blood clotting factor, wherein said viral promoter is stimulated by said at least one viral transcription activator protein); and (b) isolating the blood clotting factor from the culture broth. Suitable immortalized human cell lines, transcription activator proteins and viral promoters are those mentioned herein before. The immortalized human cell line utilized in said method preferably expresses two viral transcription activator proteins, most preferably temperature sensitive SV40 T antigen and adenovirus E1A protein. The method may further comprise the purification and virus inactivation steps (c) and (d) described herein before.

The commercially available cell line 293 T (ECACC: tsa201, ref. 96121229) was deposited with the DMSZ (Deutsche Sammlung von Mikroorganismen und Zellkulturen GmbH, Mascheroder Weg 1b, 38124 Braunschweig, Germany) on Feb. 20, 2001 under the depositary no. DSM ACC2494.

The invention is further illustrated by the following examples.

EXAMPLES

Example 1

Cloning of Factor VIII

The sequence for the recombinant factor VIII was obtained by reverse transcription from a complete human hepatocellular RNA pool. Afterwards four fragments (1/2, 3/4, 5/6, 7/8) were amplified by standard PCR using primers designed to contain restriction sites. To fit together the fragments 3/4 and 5/6 the SmaI/SalI fragment from plasmid pBSFVIII3/4 was inserted blunt into the SalI site of pBSFVII5/6 to obtain pBSFVIII3/6. Next, the fragment 3/6 was obtained by digesting pBSFVIII3/6 with XhoI/BspHI and partially with Alw44I. This fragment and the PstI/Alw44I fragment from pBSFVIII1/2 were ligated in one step into the vector backbone of pBSFVIII1/2 digested with PstI and XhoI by this means obtaining pBSFVIII1/6. The fragment 7/8 was obtained by digesting pBSFVIII7/8 with SmaI and partially with Mva1269I and ligated into pBSFVIII1/6 cut with XhoI and Mva1269I giving rise to pBSFVIII1/8. Finally the SmaI/XhoI fragment from pBSFIII1/8 was inserted blunt into the SalI site of Octagene Vector pTGFG67 (the production of said vector being disclosed in PCT/EP00/01368) resulting in the eukaryotic expression vector for the human factor VIII pTGF8-1 (s. FIGS. 1 and 2). The resulting vector encodes a factor VIII mutein having the mutations V162A, S2011N and V2223E.

Example 2

Cloning of Factor IX

The vector pUC19 (MBI Fermentas) was digested with XbaI, treated with Klenow enzyme and religated. This XbaI deleted vector was then digested with EcoRI, treated with Klenow enzyme and religated in order to delete the EcoRI site. For insertion of an XbaI site into the SacI site of this vector it was digested with SacI, treated with T4-DNA-polymerase, dephosphorylated with alkaline phosphatase and ligated with the XbaI-linker CTCTAGAG (Biolabs #1032). Another XbaI-site was inserted by digesting the newly produced vector with HindIII, treating it with Klenow, dephosphorylating it with alkaline phosphatase and ligating it with the XbaI-linker CTCTAGAG (Biolabs #1032). This vector was named pUC19/X.

In order to destroy the XbaI-site present in the vector phGFP-S65T (Clontech) this vector was digested with XbaI, treated with Klenow enzyme and religated resulting in the vector pGFP/0. A 2.3 kb fragment containing the GFP-Gene was isolated after digesting pGFP/0 with MluI, treating it with Klenow enzyme and digesting it with BamHI. This fragment was inserted into the multiple cloning site of the vector pUC19/X which was digested with SalI, treated with Klenow enzyme and digested with BamHI. The resulting vector was named pTGFG1.

The oligonucleotides (Metabion) PRE-S (5'-GGG GTA CCA GCT TCG TAG CTA GM CAT CAT GTT CTG GGA TAT CAG CTT CGT AGC TAG AAC ATC ATG TTC TGG TAC CCC-3'; SEQ ID NO: 10) and PRE-AS (5'-GGG GTA CCA GAA CAT GAT GTT CTA GCT ACG MG CTG ATA TCC CAG AAC ATG ATG TTC TAG CTA CGA AGC TGG TAC CCC-3'; SEQ ID NO: 11) were hybridized and phosphorylated by kinase reaction, resulting in the insert PRE(ds).

The vector pTGFG1 was digested with EcoO109I, treated with Klenow enzyme and dephosphorylated with alkaline phosphatase. It was then ligated with the PRE(ds) insert, resulting in the vector pTGFG5. The vector pUC19 (MBI Fermentas) was digested with SalI, treated with Klenow enzyme and dephosphorylated with alkaline phosphatase. It was ligated to the NotI-linker GCGGCCGC (Biolabs #1045), resulting in the vector pUC19/N.

Factor IX cDNA was amplified from human liver cDNA (Clontech) using two primers overlapping the start and termination codon of the factor IX open reading frame resulting in a 1387 bp fragment containing the entire open reading frame. Restriction sites for EcoRI (upstream) and BamHI (downstream) were included at the end of each primer to facilitate cloning. Amplification was performed with Pwo DNA-polymerase (Boehringer Mannheim) in 50 µl reaction volume [10 mM Tris HCl pH 8.85, 25 mM KCl, 5 mM $(NH_4)_2SO_4$, 2 mM $MgSO_4$] with 30 incubation cycles at 96° C. for 1 min, 60° C. for 1 min, 72° C. for 2 min, followed by a final extension step at 72° C. for 10 min.

Reaction products were ligated into the EcoRI- and BamHI-sites of pUC19 and transformed into E. coli DH5-α. Positive clones were selected. Sequences were confirmed by cycle sequencing (Amersham) from both ends with labeled primers (IR-700) and automated analysis on the LiCor sequencing system (MWG, Biotech).

The following primers were used:

(upstream; SEQ. ID NO: 16)
GGAATTGCGCAAAGGTFATGCAGCGCGTGAACATGATCATGGC (downstream; SEQ. ID NO: 17)
CGCGGATCGATTAAGTGAGCTTTGT1TFITCCTTAATCC A 1.4 kb fragment containing the open reading frame of the human clotting factor IX, isolated from a human cDNA library, was inserted into the PstI site of the above prepared vector pUC19/N which was digested with PstI, treated with T4-polymerase and dephosphorylated with alkaline phosphatase. From the resulting vector pUC19/N-FIX a 1.4 kb fragment containing the open reading frame of the human clotting factor IX was cut out by double-digestion with Hind III and NotI. This fragment was ligated to the 4.3 kb fragment of the HindIII and NotI double-digested vector pTGFG5 resulting in the vector pTGFG36 shown in FIG. 3. This vector is a preferred one for delivery of an expression cassette encoding factor IX into the cell, and its DNA sequence is provided in SEQ ID NO: 6.

Example 3

Human Cell Line for Protein Expression

A preferred cell line is tsA201 (ECACC Ref.: 96121229) which is a transformed embryonal human kidney cell line (293, ECACC Number 85120602) stably expressing an SV40 temperature-sensitive T antigen (J. Membrane Biol. 1996; 152:39; Gene 1995; 156:235; PNAS USA 1994; 91:12785; Pflügers Arch. 1994; 427:136; J. Gen. Physiol. 1994; 104: 507; BioTechniques 1993; 15:906). Other names for this cell line include 293tsA1609neo (Mol. Cell. Biol., 1987, 7:379) and 293T. This epithelial-like cell line has been used in a variety of functional expression assays and been reported to produce high levels of recombinant proteins. They can be cultivated in DMEM supplemented with 2 mM glutamine and 10% FCS. For efficient production of factor IX, the medium can be modified by addition of up to 100 µg/ml vitamin K (U.S. Pat. No. 4,770,999).

To simplify the purification of an expressed polypetide, cells can be cultivated in serum-free or protein-free medium containing suitable supplements. For stability reasons secreted factor VIII requires the presence of vWF in the medium (U.S. Pat. No. 5,198,349). Also the addition of lipoproteins, phospholipids, polyglycols, trace metals, heparin, non-ionic surfactants or cyclodextrin has been reported (EP0254076, U.S. Pat. Nos. 5,679,549, 5,198,349, 5,250, 421, 5,576,194, EP0872487, WO94/11525, U.S. Pat. No. 5,378,612).

Example 4

Calcium Phosphate Transfection of 293T Cells for the Transient Production of Factors VIII and IX Confluent 293T cells were plated at low density in 10 cm dishes in 6 ml DMEM/10% FCS (10 µg/ml vitamin K for FIX) the day prior to transfection. Transfection was performed roughly according to Chen and Okayama (Mol. Cell Biol., 7:2745 (1987)). 12 µg of plasmid pTGF8-1 were transfected for the production of factor VIII and pTGFG36 for the production of factor IX. Six hours after transfection the medium was replaced by fresh one and the supernatant was harvested three days post transfection and either further purified or analyzed without further purification by ELISA or coagulometry (see Examples 5 and 6).

Example 5

Determination of FIX and FVIII Concentration by ELISA

Factor IX: Human recombinant factor IX levels in supernatant of transfected 293T cells were determined by ELISA using a goat polyclonal anti-human FIX (Enzyme Research Laboratories) as capture antibody. All incubations were performed for two hours in a humid chamber at 22° C. Plates (Dynex, Immulon-4) were coated with 100 µl of 8.8 µg antibody/ml coating buffer. Blocking is not required under the conditions described. Washing the plate four times (Encore 2000, Merck) with PBS-Tween® (0,1% v/v) is sufficient to block non-specific interactions.

After each further step washing was required to eliminate unbound proteins. 100 µl of supernatant treated with 10 µl 10 mM PMSF and 10 µl 0.11 M sodium citrate were added to each well. Dilutions for samples and standard (human factor IX, house standard, Octapharma) were made in dilution buffer (HBS-BSA-EDTA-Tween®) and incubated at 100 µl/well. The detecting antibody was a peroxidase labelled goat polyclonal anti-FIX (Enzyme Research Laboratories) in a concentration of 1 µg antibody/ml dilution buffer and incubated at 100 µl/well. 150 µl ABTS (Roche) was added to each well as substrate, calorimetric reaction was detected at 405 nm after 1-2 hours. Results were calculated by linear regression of standard concentration versus standard absorbance and are summarized in the following table:

| Number of cells [/ml] | Factor IX-concentration [ng/ml] | Clotting time [s] |
|---|---|---|
| $2.1 \times 10^5$ | 36 | 45 |
| $8.7 \times 10^5$ | 20 | 79 |

Normal plasma: 37-39 s
Factor IX deficient plasma: 137-140 s

Factor VIII: Human recombinant factor VIII levels in culture filtrate of transfected 293T cells were determined by ELISA using an affinity purified polyclonal sheep anti FVIII:C preparation (F8C-EIA-C, Affinity Biologicals) as capture antibody. Coating was performed for two hours in a humid chamber at 22° C. Plates (Dynex, Immulon-4) were coated with 100 µl of a 100-fold antibody dilution in coating buffer (50 mM sodium carbonate pH9.6). Washing the plate four times (Encore 2000, Merck) with PBS-Tween® (0,1% v/v) was sufficient to block non-specific interactions.

After each further step, washing was required to eliminate unbound proteins. 100 µl each of culture filtrate samples withdrawn from different 293T clones stably transfected with pTGF8-3 after 48 h incubation were added to each well. Dilutions of FVIII standard (house standard, Octapharma) were made in dilution buffer (HBS-BSA-EDTA-Tween®) and incubated at 100 µl per well. For detection, a ready-to-use dilution of peroxidase labelled polyclonal anti-FVIII (F8C-EIA-D, Affinity Biologicals) was incubated for 60 min at 100 µl per well. For colorimetric reaction, a 5 mg O-Phenylenediamine (P-6912, Sigma) tablet was dissolved in 12 ml substrate buffer shortly before use and completed with 12 µl 30% $H_2O_2$. 150 µl of this substrate solution was added to each well and colorimetric recording was done in an MRX Reader (Dynex) at 490 nm after 10 min of incubation at room temperature in the dark and stopping of reaction by addition of 50 µl 2.5 M $H_2SO_4$ to each well. Results were calculated by linear regression of standard concentrations versus standard absorbances (FIG. 7A) and are summarized in FIG. 7B.

Example 6

Detection of Human Clotting Factor VIII and Factor IX Activity

The clotting activity of human recombinant factor VIII in supernatants of cell culture 293T cells (transfected by calcium phosphate precipitation with pTGF8-1 as described in Example 4) was determined as follows:

The clotting activity was assayed based on a partial thromboplastin time assay using Cephalin (phosphatidyl ethanolamine) activation with a manual coagulation instrument (ML-2, Instrumentation Laboratories). For the study, 100 µl undiluted supernatant from transfected 293 T-cells, 100 µl deficiency plasma (Progen) and 100 µl Cephalin (Instrumentation Laboratories) were incubated for 5 minutes at 37° C. Coagulation was started by adding 100 µl $CaCl_2$. Sample coagulation time was compared to normal plasma. The results are summarized in FIG. 5B. As can be seen from FIG. 5B, cell supernatant from cells transfected with pTGF8-1 shows a coagulation activity comparable to normal plasma while non transfected cells give a value equivalent to plasma lacking factor VIII.

Figure 10:
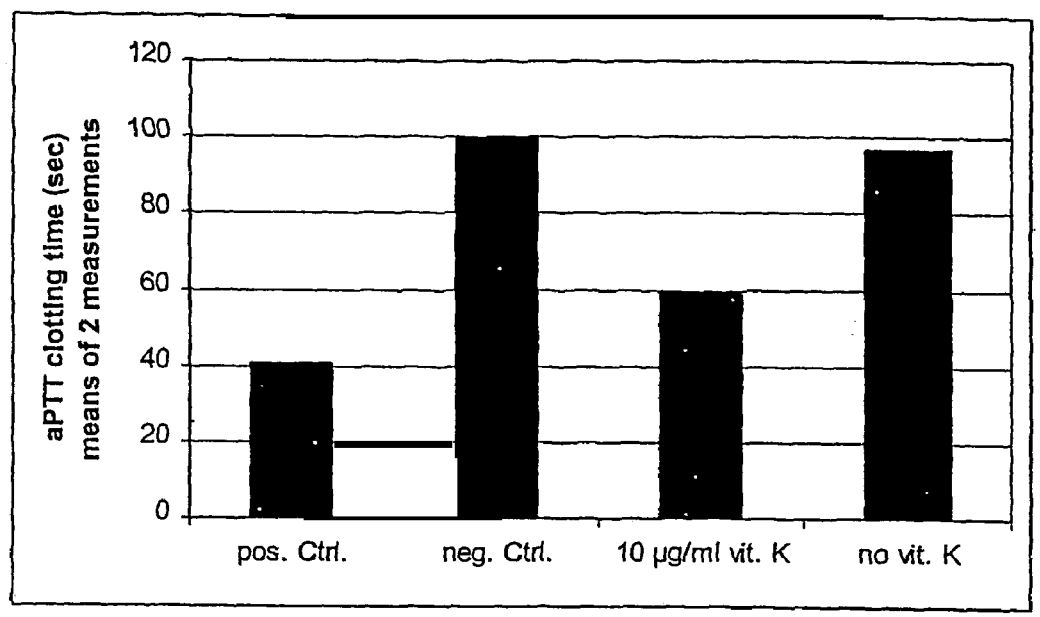
FIG. 10 shows the dependence of expression of active recombinant factor IX on the supplementation of vitamin K into culture medium.

A similar assay was performed with regard to factor IX. The results are shown in the Table of Example 5. For dependence of expression on the presence of vitamin K see FIG. 10.

Example 7

Viral Inactivation

Viral inactivation was performed in accordance with the method of U.S. Pat. No. 6,007,979. Namely, to a potentially infectious protein solution the following compounds were added subsequently, with stirring:

1. 0.2 ml of Tween® 80 and 0.06 ml of TNBP were added to 19.74 ml of the solution or
2. 0.2 ml of Triton® X-100 and 0.2 ml of TNBP were added to 19.6 ml of the solution.

1 ml of castor oil was added to preparations 1 and 2 which were then intensely extracted at room temperature for one hour.

Centrifugation was performed in each case for phase separation. For infectiousness control, samples of 1 ml each were repeatedly taken from the aqueous fraction.

Example 8

Establishment of Cell Lines Stably Expressing Factor VIII and Factor IX

The preferred vectors pTGF8-1 and pTGFG36 comprise constructs for transient expression of factor VIII and factor IX , respectively, in mammalian cells. To enable a selection method for a stably transfected cell clone, a cassette for the hygromycin-B-phosphotransferase (HindiII-Mva 1260I fragment from TK-Hyg, Clontech) was subcloned into the SmaI site being present in both vectors. The resulting constructs (pTGF8-1-hyg and pTG36hyg) then comprise in cis the expression cassettes for the human factor VIII or factor IX with a CMV-promoter and a SV40-polyadenylation signal and a hygromycin-B-phosphotransferase expression cassette with the HSV thymidine kinase promoter and HSV thymidine kinase polyadenylation signal (see FIG. 4).

The vectors pTGF8-2hyg-s and pTGF8-3 (FIG. 6, SEQ ID NOs: 12 and 14) are derivatives of pTGF8-1hyg, in that point mutations V162A, S2011N and V2223E (pTGF8-2hyg-s) and S2011N (pTGF8-3) were reverted to wildtype sequence by a PCR- dependent method using the QuikChange® protocol (Stratagene).

The coding sequence for the clotting factors can be replaced by any other gene sequence of choice. These constructs allow for the establishment of stably expressing cell lines by calcium phosphate transfection and subsequent selection for hygromycine resistance. Additionally the plasmids contain a progesterone responsive element (PRE). In transient transfection experiments with pTG36hyg the production of about 40 ng active factor IX per ml culture medium could be shown by ELISA and coagulometric assay (see Examples 5 and 6).

For the production of factor IX 293T cells were cultivated in DMEM supplemented with 10% FCS and 10 µg/ml vitamin K (U.S. Pat. No. 4,770,999; see also FIG. 10). First the critical concentration of antibiotics for an effective selection of stably transfected 293T cells had to be established. For this purpose the cells were plated at low dilution and grown in the presence of 10 to 800 µg/ml hygromycin B. After two weeks at 200 µg/ml or higher no cells were growing, so this concentration was chosen for the selection of stably transfected cells.

A typical transfection was performed in 10 cm dishes with 293T cells split the day before at a ratio of 1:15. Using the calciumphosphate precipitation method (*Biotechniques* 1988 6:7 632-638) 12 μg plasmid per dish were transfected and two days later the medium was replaced with fresh one containing 200 μg/ml hygromycin B. After 2-3 weeks of selection the medium was tested by ELISA (see Example 5) for the presence of factor VIII or IX. Positive clones were isolated and transferred to a 24-well plate.

After screening by ELISA and activity determination positive clones were subjected to two further rounds of subcloning then expanded and aliquots of them frozen for further use and characterization.

Example 9

Proof of Phenotypic Uniformity of Stably Transfected Cells by in-Situ Immunofluorescent Detection of Factor VIII Expression Each, $5 \times 10^7$ 293T cells stably transfected with pTGF8-3 (clone 49/19) and untransfected 293T cells (negative control) from adhesion cultures in DMEM+9.1% FBS were detached from the culture dishes by trypsination, washed several times and resuspended in 5 ml PBS buffer.

Figure 8:
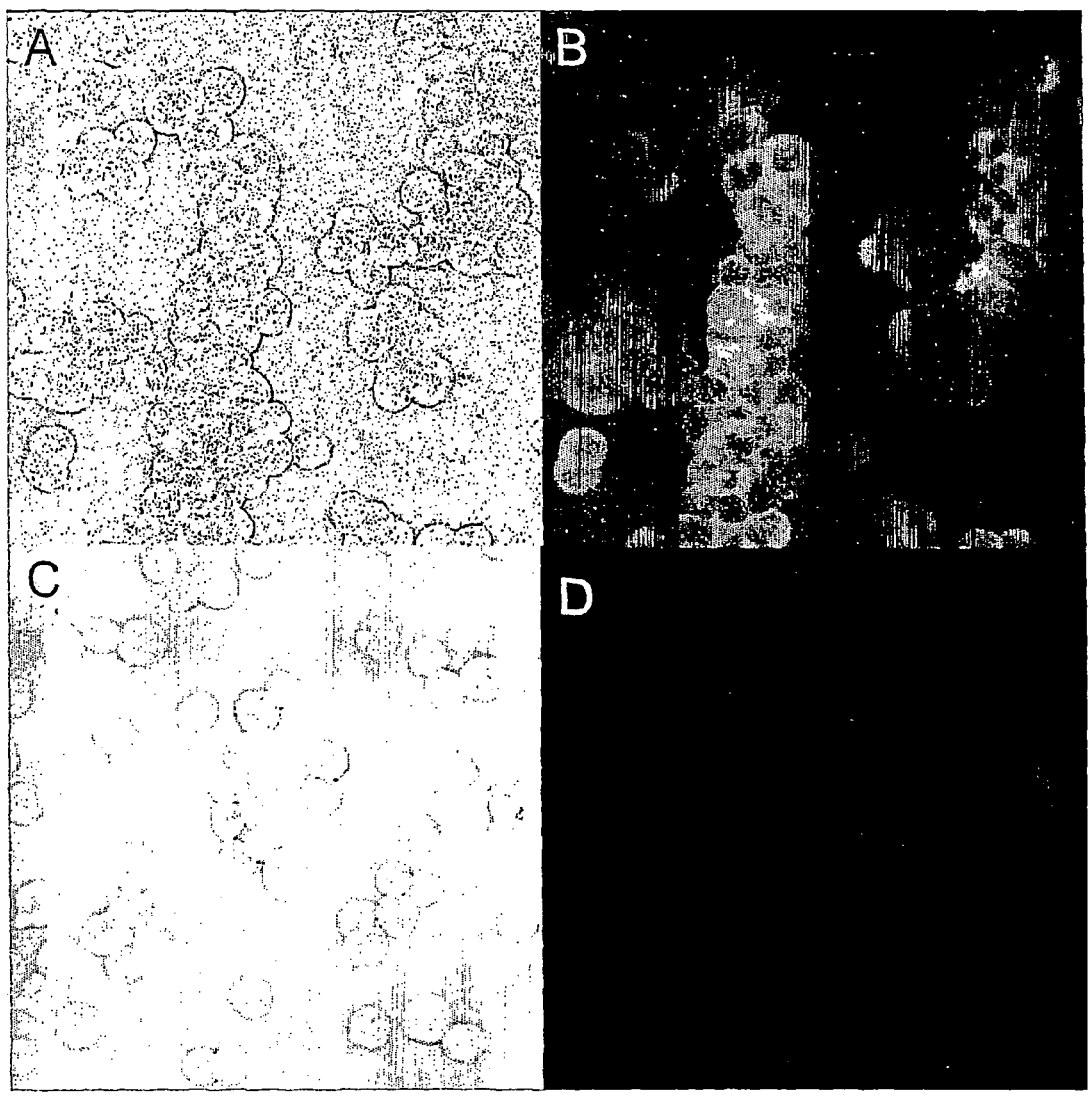
FIG. 8 shows the results of a factor VIII specific immunofluorescence assay as described in example 9. Upper row: 293T cells stably transfected with pTGF8-3, clone 49/19. Lower row: Negative control: Untransfected 293T cells. A and C: white light, no filter; B and D: Factor VIII detection by fluorescence, filter 550 nm.

2 μl of these cell suspensions were transferred to sterile microscopic glass slides and incubated at room temperature until all liquid was evaporated. Cells were fixed in 70% ethanol for 10 min and dried 5 min at room temperature. Slides were blocked against unspecific detection by incubation in a 10% dilution of FBS in PBS buffer. Primary antibody (sh antiFVIII:C F8C-EIA-C, Affinity Biologicals) was diluted 100-fold with PBS buffer containing 10% FBS and 0.1% saponine and incubated for 60 min at room temperature in a humid incubation chamber. After intense washing with PBS, a 100-fold dilution of the secondary antibody (rb anti sh CY3 conjugate 313-165-003, Jackson ImmunoResearch) was prepared and incubated in the way described above. Subsequently, the microscopic preparation was washed intensely and covered by a layer of 50% glycerol and a cover glass. Cells were visualized by white light- and by fluorescence microscopy (emission at 570 nm). Results are depicted in FIG. 8.

Example 10

Thermal Stability Test on Recombinant Factor IX in Culture Filtrate

Culture filtrate harvested from 293T cells 48 h after transient transfection with pTGFG36 in the presence of 100 μg/ml vitamin K and stored at −80° C. for 7 days was thawed quickly, distributed into 7 500 μl aliquots which then were subsequently submitted to the following thermal incubations:

| sample | temp. (° C.) | time (min) |
|---|---|---|
| 1 | 0 | 240 |
| 2 | 20 | 30 |
| 3 | 20 | 60 |
| 4 | 20 | 240 |
| 5 | 37 | 30 |
| 6 | 37 | 60 |
| 7 | 37 | 240 |

Figure 9:
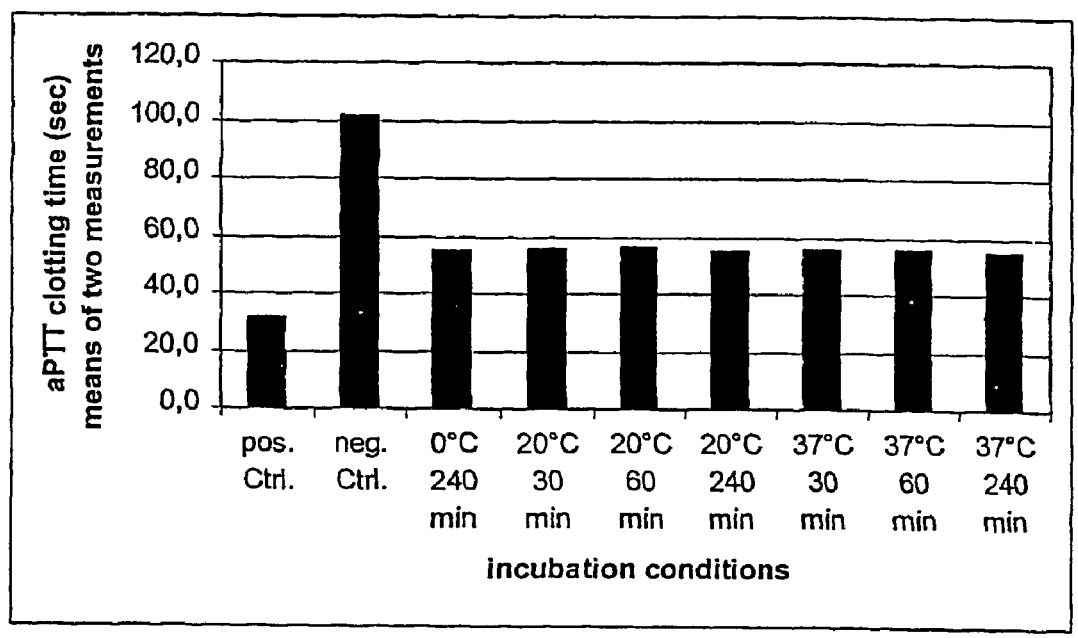
FIG. 9 shows the influence of thermal treatment on FIX activity in culture filtrate as described in example 10.

Samples were chilled on ice and FIX activity was determined as outlined in Example 6 (double determinations). Results are shown in FIG. 9. Activity remained almost stable within incubation conditions up to 240 min 37° C.

We claim:

1. A human factor VIII mutein, the sequence of which corresponds to the mature wild-type factor VIII sequence shown in SEQ ID NO:2, wherein the B-domain including residues Ser741 to Arg1648 has been deleted and replaced by an Arg-rich linker peptide consisting of the sequence of SEQ ID NO: 9, the sequence optionally consisting of up to three point mutations selected from the group consisting of:
   (a) Val at position 162 has been replaced by a neutral amino acid residue selected from Gly, Ala, Leu, Ile, Met and Pro;
   (b) Ser at position 2011 has been replaced by a hydrophilic amino acid residue selected from Asn, Thr and Gln; and
   (c) Val at position 2223 has been replaced by an acidic amino acid residue selected from Glu and Asp,
   wherein said factor VIII mutein has blood coagulation activity.

2. The factor VIII mutein of claim 1, wherein the factor VIII mutein has at least one of the mutations (a), (b) and (c), as defined in claim 1, or at least one of the mutations (a) and (b).

3. The factor VIII mutein of claim 1, wherein the factor VIII mutein has all three mutations (a), (b) and (c) as defined in claim 1.

4. The factor VIII mutein according to claim 1, wherein the factor VIII mutein has all three mutations (a), (b) and (c), and wherein in mutations (a) Val at position 162 has been replaced by Ala, in mutation (b) Ser at position 2011 has been replaced by Asn, and in mutation (c) Val at position 2223 has been replaced by Glu.

5. The factor VIII mutein according to claim 2, wherein the factor VIII mutein has at least one mutation selected from the group consisting of Val at position 162 is replaced by Ala, Ser at position 2011 is replaced by Asn, and Val at position 2223 is replaced by Glu.

6. The factor VIII mutein of claim 1, which comprises amino acids 1 to 1440 of SEQ ID NO: 4, 13 or 15.

7. A DNA sequence coding for the factor VIII mutein of claim 1.

8. A DNA sequence coding for the factor VIII mutein of claim 2.

9. A DNA sequence coding for the factor VIII mutein of claim 3.

10. A DNA sequence coding for the factor VIII mutein of claim 4.

11. A DNA sequence coding for the factor VIII mutein of claim 5.

12. A DNA sequence coding for the factor VIII mutein of claim 6.

13. A vector comprising DNA encoding the factor VIII mutein of claim 1.

14. A vector comprising DNA encoding a factor VIII mutein of claim 2.

15. A vector comprising DNA encoding a factor VIII mutein of claim 3.

16. A vector comprising DNA encoding a factor VIII mutein of claim 4.

17. A vector comprising DNA encoding a factor VIII mutein of claim 5.

18. A vector comprising DNA encoding a factor VIII mutein of claim 6.

19. The vector of claim 13 which is pTGF8-1, pTGF8-2hyg-s or pTGF8-3.

20. A gene transfer vector comprising DNA encoding the factor VIII mutein of claim 1.

21. A gene transfer vector comprising DNA encoding a factor VIII mutein of claim 2.

22. A gene transfer vector comprising DNA encoding a factor VIII mutein of claim 3.

23. A gene transfer vector comprising DNA encoding a factor VIII mutein of claim 4.

24. A gene transfer vector comprising DNA encoding a factor VIII mutein of claim 5.

25. A gene transfer vector comprising DNA encoding a factor VIII mutein of claim 6.

26. A host cell comprising the DNA sequence of claim 7.
27. A host cell comprising the DNA sequence of claim 8.
28. A host cell comprising the DNA sequence of claim 9.
29. A host cell comprising the DNA sequence of claim 10.
30. A host cell comprising the DNA sequence of claim 11.
31. A host cell comprising the DNA sequence of claim 12.

32. A method for the production of a factor VIII mutein, comprising culturing the host cell of claim 26 and isolating the factor VIII mutein from the culture broth.

33. A pharmaceutical composition comprising the factor VIII mutein of claim 1.

34. A pharmaceutical composition comprising the factor VIII mutein of claim 2.

35. A pharmaceutical composition comprising the factor VIII mutein of claim 3.

36. A pharmaceutical composition comprising the factor VIII mutein of claim 4.

37. A pharmaceutical composition comprising the factor VIII mutein of claim 5.

38. A pharmaceutical composition comprising the factor VIII mutein of claim 6.

39. A composition comprising the gene transfer vector of claim 20.

40. A composition comprising the gene transfer vector of claim 21.

41. A composition comprising the gene transfer vector of claim 22.

42. A composition comprising the gene transfer vector of claim 23.

43. A composition comprising the gene transfer vector of claim 24.

44. A composition comprising the gene transfer vector of claim 25.

* * * * *